US012226458B2

(12) United States Patent
Michelich et al.

(10) Patent No.: US 12,226,458 B2
(45) Date of Patent: Feb. 18, 2025

(54) SYSTEM FOR PROVIDING AN UP-TO-DATE AND LONG-ACTING OR ULTRA-LONG-ACTING INSULIN DOSE GUIDANCE RECOMMENDATION TO TREAT DIABETES MELLITUS

(71) Applicant: Novo Nordisk A/S, Bagsvaerd (DK)

(72) Inventors: Alan John Michelich, Seattle, WA (US); Thomas Dedenroth Miller, Seattle, WA (US); Oleksandr Shvets, Everett, WA (US); Anuar Imanbayev, Seattle, WA (US); Brad Warren Van Orden, Seattle, WA (US)

(73) Assignee: Novo Nordisk A/S, Bagsvaerd (DK)

( * ) Notice: Subject to any disclaimer, the term of this patent is extended or adjusted under 35 U.S.C. 154(b) by 1351 days.

(21) Appl. No.: 16/417,032

(22) Filed: May 20, 2019

(65) Prior Publication Data

US 2019/0388512 A1 Dec. 26, 2019

Related U.S. Application Data

(63) Continuation of application No. 16/020,478, filed on Jun. 27, 2018, now Pat. No. 10,335,464.

(60) Provisional application No. 62/690,157, filed on Jun. 26, 2018.

(51) Int. Cl.
*A61K 38/28* (2006.01)
*A61B 5/00* (2006.01)
*A61B 5/145* (2006.01)
*A61K 38/26* (2006.01)
*A61P 3/10* (2006.01)
*G16H 10/60* (2018.01)
*G16H 20/17* (2018.01)

(52) U.S. Cl.
CPC .......... *A61K 38/28* (2013.01); *A61B 5/14532* (2013.01); *A61B 5/4839* (2013.01); *A61P 3/10* (2018.01); *G16H 20/17* (2018.01); *A61K 38/26* (2013.01); *A61K 2300/00* (2013.01); *G16H 10/60* (2018.01)

(58) Field of Classification Search
None
See application file for complete search history.

(56) References Cited

U.S. PATENT DOCUMENTS

| | | |
|---|---|---|
| 3,528,960 A | 9/1970 | Haas |
| 3,868,358 A | 2/1975 | Jackson |
| 3,907,676 A | 9/1975 | Jorgensen |
| 4,476,118 A | 10/1984 | Brange et al. |
| 4,652,548 A | 3/1987 | Chance et al. |
| 4,669,430 A | 6/1987 | Reinold et al. |
| 4,764,592 A | 8/1988 | Massey et al. |
| 4,876,322 A | 10/1989 | Budde et al. |
| 4,983,658 A | 1/1991 | Kress et al. |
| 5,008,241 A | 4/1991 | Markussen et al. |
| 5,177,058 A | 1/1993 | Dorschug |
| 5,382,574 A | 1/1995 | Jorgensen |
| 5,605,884 A | 2/1997 | Lee et al. |
| 5,646,242 A | 7/1997 | Baker et al. |
| 5,750,497 A | 5/1998 | Havelund et al. |
| 5,830,999 A | 11/1998 | Dunn |
| 5,866,538 A | 2/1999 | Norup et al. |
| 5,898,067 A | 4/1999 | Balschmidt et al. |
| 5,905,140 A | 5/1999 | Hansen |
| 6,011,007 A | 1/2000 | Havelund et al. |
| 6,174,856 B1 | 1/2001 | Langballe et al. |
| 6,211,144 B1 | 4/2001 | Havelund |
| 6,221,837 B1 | 4/2001 | Ertl et al. |
| 6,251,856 B1 | 6/2001 | Markussen et al. |
| 6,335,316 B1 | 1/2002 | Hughes et al. |
| 6,451,762 B1 | 9/2002 | Havelund et al. |
| 6,451,970 B1 | 9/2002 | Schaffer et al. |
| 6,504,005 B1 | 1/2003 | Fridkin et al. |
| 6,620,780 B2 | 9/2003 | Markussen et al. |
| 6,652,886 B2 | 11/2003 | Ahn et al. |

(Continued)

FOREIGN PATENT DOCUMENTS

| | | |
|---|---|---|
| AU | 2011252127 B2 | 2/2014 |
| CN | 86101489 A | 1/1987 |

(Continued)

OTHER PUBLICATIONS

Rubin RR et al.. Factors affecting use of insulin pens by patients with type 2 diabetes. Diabetes Care. 2008 vol. 31 pp. 430-432.

Peyrot M and Rubin RR. Factors associated with persistence and resumption of insulin pen use for patients with type 2 diabetes. Diabetes Technology & Therapeutics. 2011 vol. 13 No. 43-48.

Oyer D, et al. Ease of use and preference of a new versus widely available pre-filled insulin pen assessed by people with diabetes, physicians and nurses. Expert Opinion on Drug Delivery. 2011 vol. 8, pp. 1259-1269.

(Continued)

*Primary Examiner* — G. Steven Vanni
(74) *Attorney, Agent, or Firm* — Wesley Nicolas

(57) ABSTRACT

The invention relates to a novel administration regime useful in the treatment of diseases or conditions where administration of insulin will be of benefit. In particular, the invention relates to a long-acting or ultra-long acting insulin for use in treating a disease or condition where administration of insulin will be of benefit, wherein the administration of said insulin includes or consists of one or more of the following steps: (a) obtaining a first data set of the subject, (b) obtaining a second data set of the subject, (c) obtaining a first data structure of the subject, and (d) obtaining a second data structure of the subject. When a determination is made that the at least first data structure, second data structure, first data set, and second data set collectively do contain the set of evaluation information, the device further includes providing the long-acting or ultra-long-acting insulin dose guidance recommendation.

29 Claims, 15 Drawing Sheets

(56) References Cited

U.S. PATENT DOCUMENTS

| | | |
|---|---|---|
| 6,869,930 B1 | 3/2005 | Havelund et al. |
| 7,229,964 B2 | 6/2007 | Markussen et al. |
| 7,402,565 B2 | 7/2008 | Kjeldsen et al. |
| 7,544,656 B2 | 6/2009 | Sabetsky |
| 7,615,532 B2 | 11/2009 | Jonassen et al. |
| 7,713,929 B2 | 5/2010 | Steiner et al. |
| 8,003,605 B2 | 8/2011 | Bayer et al. |
| 8,067,362 B2 | 11/2011 | Kodra et al. |
| 8,404,645 B2 | 3/2013 | Schlein |
| 8,691,759 B2 | 4/2014 | Madsen et al. |
| 8,722,620 B2 | 5/2014 | Fynbo et al. |
| 8,796,205 B2 | 8/2014 | Jonassen et al. |
| 8,828,923 B2 | 9/2014 | Jonassen et al. |
| 8,933,021 B2 | 1/2015 | Hubalek et al. |
| 8,962,794 B2 | 2/2015 | Madsen et al. |
| 9,034,818 B2 | 5/2015 | Poulsen et al. |
| 9,045,560 B2 | 6/2015 | Madsen et al. |
| 9,131,722 B2 | 9/2015 | Kim et al. |
| 9,447,163 B2 | 9/2016 | Mollerup et al. |
| 9,481,721 B2 | 11/2016 | Naver et al. |
| 9,603,904 B2 | 3/2017 | Johansen et al. |
| 9,688,737 B2 | 6/2017 | Madsen et al. |
| 9,839,579 B2 | 12/2017 | Weeks et al. |
| 9,884,094 B2 | 2/2018 | Johansen et al. |
| 10,137,172 B2 | 11/2018 | Johansen et al. |
| 10,368,745 B2 | 8/2019 | Bousamra et al. |
| 2002/0045731 A1 | 4/2002 | Schaffer et al. |
| 2002/0155994 A1 | 10/2002 | Havelund et al. |
| 2003/0004096 A1 | 1/2003 | Boderke |
| 2003/0236196 A1 | 12/2003 | Kerwin et al. |
| 2004/0006000 A1 | 1/2004 | Langkjaer |
| 2004/0037909 A1 | 2/2004 | Kim et al. |
| 2004/0116345 A1 | 6/2004 | Besman et al. |
| 2004/0138099 A1 | 7/2004 | Draeger |
| 2005/0054818 A1 | 3/2005 | Brader et al. |
| 2005/0074866 A1 | 4/2005 | Grancha et al. |
| 2005/0222006 A1 | 10/2005 | Havelund et al. |
| 2005/0232899 A1 | 10/2005 | Balwani et al. |
| 2006/0183668 A1 | 8/2006 | Jonassen et al. |
| 2008/0076705 A1 | 3/2008 | Kodra et al. |
| 2009/0074882 A1 | 3/2009 | Havelund et al. |
| 2009/0137454 A1 | 5/2009 | Fynbo et al. |
| 2009/0186807 A1 | 7/2009 | Boderke |
| 2009/0239785 A1 | 9/2009 | Hubalek et al. |
| 2009/0312236 A1 | 12/2009 | Beals et al. |
| 2010/0009899 A1 | 1/2010 | Jonassen et al. |
| 2010/0167990 A1 | 7/2010 | Poulsen et al. |
| 2011/0152185 A1 | 6/2011 | Plum et al. |
| 2011/0230402 A1 | 9/2011 | Johansen et al. |
| 2011/0301081 A1 | 12/2011 | Becker et al. |
| 2013/0261051 A1 | 10/2013 | Johansen |
| 2014/0073759 A1 | 3/2014 | Mollerup et al. |
| 2014/0328943 A1 | 11/2014 | Havelund et al. |
| 2014/0349925 A1 | 11/2014 | Jonassen et al. |
| 2015/0126439 A1 | 5/2015 | Johansen et al. |
| 2015/0250857 A1 | 9/2015 | Andresen et al. |
| 2016/0058840 A1 | 3/2016 | Johansen et al. |
| 2016/0296602 A1 | 10/2016 | Johansen |
| 2017/0165327 A1 | 6/2017 | Andresen et al. |
| 2017/0319664 A1 | 11/2017 | Johansen |
| 2018/0125946 A1 | 5/2018 | Johansen |
| 2019/0112348 A1 | 4/2019 | Madsen et al. |
| 2019/0160155 A1 | 5/2019 | Johansen |
| 2019/0194285 A1 | 6/2019 | Olsen et al. |
| 2019/0374614 A1 | 12/2019 | Skibsted et al. |
| 2021/0060132 A1 | 3/2021 | Andresen et al. |

FOREIGN PATENT DOCUMENTS

| | | |
|---|---|---|
| CN | 88102311 A | 11/1988 |
| CN | 1829738 A | 9/2006 |
| CN | 101389650 A | 12/2006 |
| CN | 101454019 A | 6/2009 |
| CN | 102202683 A | 9/2011 |
| CN | 102947833 A | 2/2013 |
| DE | 1212679 B | 3/1966 |
| EP | 214826 A2 | 3/1987 |
| EP | 315968 A1 | 5/1989 |
| EP | 375437 A2 | 6/1990 |
| EP | 383472 A2 | 8/1990 |
| EP | 420649 A2 | 4/1991 |
| EP | 818204 A2 | 1/1998 |
| EP | 0925792 A2 | 12/1998 |
| EP | 1153608 A1 | 11/2001 |
| EP | 884053 B1 | 10/2002 |
| EP | 1283051 A1 | 2/2003 |
| EP | 0894095 | 5/2003 |
| EP | 0785713 B1 | 9/2003 |
| EP | 1595544 A1 | 11/2005 |
| EP | 2107069 A2 | 10/2009 |
| EP | 1951198 B1 | 6/2010 |
| EP | 2264065 A2 | 12/2010 |
| EP | 2264066 A2 | 12/2010 |
| EP | 2275439 A2 | 1/2011 |
| EP | 2287184 A2 | 2/2011 |
| EP | 2387989 A2 | 11/2011 |
| EP | 2389945 A1 | 11/2011 |
| EP | 2505593 A1 | 10/2012 |
| GB | 1042194 A | 9/1966 |
| GB | 1492997 | 11/1977 |
| JP | B S36-11994 | 7/1961 |
| JP | 38005689 | 5/1963 |
| JP | B S38-5689 | 5/1963 |
| JP | 1254699 | 5/1979 |
| JP | 57-067548 A | 4/1982 |
| JP | 02101022 | 4/1990 |
| JP | H109502867 | 3/1997 |
| JP | H10509176 | 8/1998 |
| JP | 11-502110 | 2/1999 |
| JP | 2000-501419 A | 2/2000 |
| JP | 2000-504732 A | 4/2000 |
| JP | 2000-515542 | 11/2000 |
| JP | 2001-518915 A | 10/2001 |
| JP | 2001-518916 A | 10/2001 |
| JP | 2001-521004 A | 11/2001 |
| JP | 2001-521006 A | 11/2001 |
| JP | 2001-521904 A | 11/2001 |
| JP | 2001-526225 A | 12/2001 |
| JP | 2002-527487 A | 8/2002 |
| JP | 2002-308899 A | 10/2002 |
| JP | 2002-543092 A | 12/2002 |
| JP | 2004-523589 A | 8/2004 |
| JP | 2006-511441 A | 4/2006 |
| JP | 2006-519253 | 8/2006 |
| JP | 2007-523881 | 8/2007 |
| JP | 2009-522231 | 6/2009 |
| JP | 4808785 B2 | 11/2011 |
| JP | 4959005 B2 | 6/2012 |
| JP | 5026567 B2 | 9/2012 |
| JP | 5331071 B2 | 10/2013 |
| RU | 2160118 C2 | 12/2000 |
| RU | 2164520 C2 | 3/2001 |
| RU | 2006103280 A | 9/2007 |
| RU | 2317821 C2 | 2/2008 |
| RU | 2352581 C2 | 4/2009 |
| WO | 91/09617 A1 | 7/1991 |
| WO | 91/12817 A1 | 9/1991 |
| WO | 9307922 A1 | 4/1993 |
| WO | 93/12812 A1 | 7/1993 |
| WO | 95/07931 A1 | 3/1995 |
| WO | 95/32730 A1 | 12/1995 |
| WO | 96/10417 A1 | 4/1996 |
| WO | 96/29344 | 9/1996 |
| WO | 97/04801 A1 | 2/1997 |
| WO | 9731022 A1 | 8/1997 |
| WO | 98/02460 A1 | 1/1998 |
| WO | 98/05361 A1 | 2/1998 |
| WO | 98/42367 A1 | 10/1998 |
| WO | 98/42368 A1 | 10/1998 |
| WO | 98/47529 A1 | 10/1998 |
| WO | 99/21573 | 5/1999 |
| WO | 99/21578 | 5/1999 |
| WO | 99/21888 A1 | 5/1999 |
| WO | 99/22754 | 5/1999 |

(56) References Cited

FOREIGN PATENT DOCUMENTS

| WO | 99/24071 A1 | 5/1999 |
|---|---|---|
| WO | 99/32116 A1 | 7/1999 |
| WO | 00/23098 A1 | 4/2000 |
| WO | 00/43034 A2 | 7/2000 |
| WO | 00/64940 | 11/2000 |
| WO | 2001/49314 A2 | 7/2001 |
| WO | 02076495 A1 | 10/2002 |
| WO | 2003/002136 A2 | 1/2003 |
| WO | 03/013573 | 2/2003 |
| WO | 03030829 A2 | 4/2003 |
| WO | 03/0053339 A2 | 7/2003 |
| WO | 03/053339 A2 | 7/2003 |
| WO | 03/094951 A1 | 11/2003 |
| WO | 03/094956 A1 | 11/2003 |
| WO | 2004/039392 A2 | 5/2004 |
| WO | 2004074481 A1 | 9/2004 |
| WO | 2004/112828 A1 | 12/2004 |
| WO | 2005/005477 A2 | 1/2005 |
| WO | 2005/016365 A2 | 2/2005 |
| WO | 2005012347 A2 | 2/2005 |
| WO | 2005/021022 A2 | 3/2005 |
| WO | 2005/47508 A1 | 5/2005 |
| WO | 2005/063298 A1 | 7/2005 |
| WO | 2005/089722 A1 | 9/2005 |
| WO | 2005/117948 A1 | 12/2005 |
| WO | 2006/008238 A1 | 1/2006 |
| WO | 2006/020720 A2 | 2/2006 |
| WO | 2006/023665 A2 | 3/2006 |
| WO | 06/51103 A2 | 5/2006 |
| WO | 2006/053906 A1 | 5/2006 |
| WO | 2006/079019 A2 | 7/2006 |
| WO | 2006/082204 | 8/2006 |
| WO | 2006/082205 | 8/2006 |
| WO | 2007/041481 A1 | 4/2007 |
| WO | 2007074133 A2 | 7/2007 |
| WO | 2007096431 A1 | 8/2007 |
| WO | 2007/121256 A2 | 10/2007 |
| WO | 2007/128815 A1 | 11/2007 |
| WO | 2007/128817 A2 | 11/2007 |
| WO | 07135117 A2 | 11/2007 |
| WO | 2008/034881 A1 | 3/2008 |
| WO | 2008/152106 A1 | 12/2008 |
| WO | 2009/060071 A1 | 5/2009 |
| WO | 2009/063072 A2 | 5/2009 |
| WO | 2010049488 A1 | 5/2010 |
| WO | 2011141407 A1 | 11/2011 |
| WO | 2012055967 A2 | 5/2012 |
| WO | 2012119007 A1 | 9/2012 |
| WO | 2013037754 A2 | 3/2013 |
| WO | 2013164375 A1 | 11/2013 |
| WO | 2018001853 A1 | 1/2018 |
| WO | 2018007172 A1 | 1/2018 |
| WO | 2018037080 A1 | 3/2018 |
| WO | 2019072818 A1 | 4/2019 |

OTHER PUBLICATIONS

Bailey T, et al Usability and preference evaluation of a prefilled insulin pen with a novel injection mechanism by people with diabetes and healthcare professionals. Current Medical Research and Opinion 2011, vol. 27 pp. 2043-2052.

Nadeau DA, et al. Healthcare professional and patient assessment of a new prefilled insulin pen versus two widely available prefilled insulin pens for ease of use, teaching and learning. Current Medical Research and Opinion 2012;vol. 28.No. 1 pp. 3-13.

Lajara R, et al. Healthcare professional and patient perceptions of a new prefilled insulin pen versus vial and syringe. Expert Opinion on Drug Delivery 2012, vol. 9, pp. 1181-1196.

Bailey T, et al. FlexTouch® for the delivery of insulin: technical attributes and perception among patients and healthcare professionals. Expert Review of Medical Devices 2012, vol. 9, pp. 209-217.

Anthony H. Barnett, Diabetic Medicine, a Review of Basal Insulins, 2003, vol. 20, No. 11, pp. 873-885.

Heise, T. et al., Diabetes, Obesity and Metabolism, Towards Peakless, Reproducible and Long-Acting Insulins. an Assessment of the Basal Analogues Based on Isoglycaemic Clamp Studies, 2007, vol. 9, No. 5, pp. 648-659.

IDF Clinical Guidelines Task Force, Brussels: International Diabetes Federation 2005, Global Guideline for Type 2 Diabetes, 2005.

IDF Clinical Guidelines Task Force, Brussels: International Diabetes Federation 2007, Guideline for Management of Postmeal Glucose, 2007.

Nathan, D. M. et al., Diabetes Care, Management of Hyperglycemia in Type 2 Diabetes: A Consensus Algorithm for the Initiation and Adjustment of Therapy, 2008, vol. 31, No. 1, pp. 173-175.

Talboys Catalog, 2008 Laboratory Equipment Catalog, Talboys by Troemner, 122 pages (2008).

Heise et al "Lower Within-Subject Variability of Insulin Detemir in Comparison to NPH Insulin an Insulin Glargine in People with Type 1 Diabetes" Diabetes, 2004, vol. 53, pp. 1614-1620.

Novo Nordisk, Levemir Product Information, Jun. 16, 2005. 42 pages.

"America Pink", http://america.pink/insulin-degludec_2091149.html, downloaded Aug. 24, 2016.

L. Heinemann and J. H. Anderson Jr. Diabetes Technol Ther 6 (5):698-728, 2004.

Living with Diabetes, available at http://www.diabetes.org/living-with-diabetes/treatment-and-care/medication/?loc=lwd-slabnav, accessed on Jan. 5, 2017.

WebMD "What is a unit of insulin," available at http://answers.webmd.com/answers/1196453/what-is-a-unit-of-insulin, accessed Nov. 8, 2018.

Heise et al., "Insulin Degludec 200 U/mL is Ultra-Long Acting and Has a Flat and Stable Glucose-Lowering Effect," Canadian Journal of Diabetes, 2012, vol. 36, No. 6, p. S13.

Springer et al., "Management of Type 2 Diabetes Mellitus in Children and Adolescents", Pediatrics, 2013, vol. 131, No. 2, pp. e648-e664.

Heise et al., "Ultra-Long-Acting Insulin Degludec has a Flat and Stable Glucose-Lowering Effect in Type 2 Diabetes," Diabetes, Obesity and Metabolism, 2012, vol. 14, pp. 944-950.

Heller et al., "Insulin Degludec, an Ultra-Longacting Basal Insulin, Versus Insulin Glargine . . . : a Phase 3, Randomized, Open-Label, Treat-to-Target Non-Inferiority Trial," The Lancet, 2012, vol. 379, pp. 1489-1497.

Tambascia et al., "Degludec: the new ultra-long insulin analogue," Diabetology Metabol. Synd., 2015, vol. 7, pp. 1-7.

Lane W. S. et al., High-dose insulin therapy: is it time for U-500 insulin?, Endocrine Practice, 2009, vol. 15, No. 1, pp. 71-79.

Segal A. R. et al., Use of concentrated insulin human regular (U-500) for patients with diabetes, American Journal of Health-System Pharmacy, 2010, vol. 67, No. 18, pp. 1526-1535.

Valentine V., Don't Resist Using U-500 Insulin and Pramlintide for Severe Insulin Resistance, Clinical Diabetes, 2012, vol. 30, No. 2, pp. 80-84.

Obesity Society: Your weight and diabetes—http://www.obesity.org/resources-for/your-weight-and-diabetes.htm, (accessed Jul. 21, 2015).

Inzucchi S. E. et al., Management of hyperglycaemia in type 2 diabetes: a patient-centered approach. Position statement of the American Diabetes Association (ADA) and the European Association for the Study of Diabetes (EASD), Diabetologia, 2012, vol. 55, No. 6, pp. 1577-1596.

Crasto W et al., Insulin U-500 in severe insulin resistance in type 2 diabetes mellitus, Postgraduate Medical Journal, 2009, vol. 85, No. 1002, pp. 219-222.

Heise T et al., Insulin Degludec Has a Two-Fold Longer Half-Life and a More Consistent Pharmacokinetic Profile Than Insulin Glargine, Diabetes, 2011, vol. 60(Suppl 1), LB11, (Abstract 37-LB).

Nosek L. et al., Ultra-Long-Acting Insulin Degludec Has a Flat and Stable Glucose-Lowering Effect, Diabetes 2011, 60(Suppl 1), LB14 (Abstract 49-LB).

Korsatko S. et al., Ultra-Long-Acting Insulin Degludec: Two Different Formulations (U100 and U200) Are Bioequivalent and Show Similar Pharmacodynamics, Diabetes 2011, 60(Suppl 1), A624 (Abstract 2349-PO).

(56) References Cited

OTHER PUBLICATIONS

Zinman B. et al., Insulin degludec, an ultra-long-acting basal insulin, once a day or three times a week versus insulin glargine once a day in patients with type 2 diabetes: a 16-week, randomized, open-label, phase 2 trial. The Lancet, 2011, vol. 377, 924-931.
Heller S. et al., Insulin degludec, an ultra-longacting basal insulin, versus insulin glargine in basal-bolus treatment with mealtime insulin aspart in type 1 diabetes (Begin Basal-Bolus Type 1): a phase 3, randomised, open-label, treat-to-target non-inferiority trial, The Lancet 2012, vol. 379, pp. 1489-1497.
Garber A. J. et al., Insulin degludec, an ultra-longacting basal insulin, versus insulin glargine in basal-bolus treatment with mealtime insulin aspart in type 2 diabetes (Begin Basal-Bolus Type 2): a phase 3, randomised, open-label, treat-to-target non-inferiority trial, The Lancet, 2012, vol. 379, pp. 1498-1507.
Declaration of Helsinki, Ethical principles for medical research involving human subjects., Journal of Indian Medical Association, 2009, vol. 107, No. 6, pp. 403-405.
Defining and Reporting Hypoglycemia in Diabetes: A report from the American Diabetes Association Workgroup on Hypoglycemia, Diabetes Care, 2005, vol. 28, No. 5, pp. 1245-1249.
Humulin® R Regular U-500 (Concentrated), Insulin Human Injection, USP (rDNA Origin), Eli Lilly and Company, Lilly USA, LLC, Indianapolis, IN 46285, USA, 1996.
Thornton S. et al., Intravenous overdose of insulin glargine without prolonged hypoglycemic effects, The Journal of Emergency Medicine, 2012, vol. 43, No. 3, pp. 435-437, XP002711646.
Zinman B. et al., Insulin degludec versus insulin glargine in insulin-naive patients with type 2 diabetes: a 1-year, randomized, treat-to-target trial (Begin Once long), Diabetes Care, 2012, vol. 35, No. 12, pp. 2464-2471, XP9172018.
Rodbard H et al., Reduced risk of hypoglycaemia with insulin degludec vs insulin glargine in patients with type 2 diabetes requiring high doses of basal insulin: meta-analysis of five randomized trials. Presented as an oral at the AACE 21st Annual Scientific and Clinical Congress, Philadelphia, PA, 2012, (Abstract 241).
ICH Harmonised Tripartite Guideline: Guideline for Good Clinical Practice, Journal of postgraduate medicine, 2001, vol. 47, No. 3, pp. 199-203.
Marcus A., Diabetes care—insulin delivery in a changing world, The Medscape Journal of Medicine, 2008, vol. 10, No. 5, 120.
Hoevelmann U. et al., Insulin degludec 200 U/ml is ultra-langacting and has a flat and stable glucose-lowering effect, Diabetologia, 2012, vol. 55, No. Suppl. 1, pp. S374-S375, XP002723769 & 48th Annual Meeting of the European-Association-For-The-Study-Of-Diabetes; Berlin, Germany; Oct. 1-5, 2012.
Wang F. et al., Insulin degludec as an ultralong-acting basal insulin once a day: a systematic review, Diabetes, Metabolic Syndrome and Obesity : Targets and Therapy, 2012, vol. 5, pp. 191-204, XP002723770.
Korsatko S. et al., Ultra-long-acting insulin degludec: bioequivalence and similar pharmacodynamics shown for two different formulations (U100 and U200), Diabetologia, 2011, vol. 54, No. Suppl. 1, XP002723771, p. S427, & 47th Annual Meeting of the European-Association-For-The-Study-Of-Diabetes (EASD); Lisbon, Portugal; Sep. 12-16, 2011.
Havelund, S. et al., "The Mechanism of Protraction of Insulin Detemir, a Long-Acting, Acylated Analog of Human Insulin", Pharmaceutical Research, 2004, vol. 21, No. 8, pp. 1498-1504.
Barnett, A.H., "A Review of Basal Insulins," Diabet Med, 2003, vol. 20, No. 11, pp. 873-885.
Brussels: International Diabetes Federation, IDF Clinical Guidelines Task Force, Guideline for Management of Postmeal Glucose, 2007, pp. 1-32, http://www.idf.org/webdata/docs/Guideline_PMG_final.pdf.
Brussels: International Diabetes Federation, IDF Clinical Guidelines Task Force, Global Guideline for Type 2 Diabetes, 2005, pp. 1-82, http://www.idf.org/webdata/docs/IDF%20GGT2D.pdf.
Definition of Moiety From http://dictionary.reference.com/browse/moiety, 2010, pp. 1-3.

Irie et al., "Pharmacokinetics and Pharmacodynamics of Single Dose Insulin Detemir, Long-Acting Soluble Insulin Analogue Compared to NPH Insulin in Patients With Type 1 Diabetes Mellitus", J Clin Ther Med, 2007, vol. 23, No. 5, pp. 349-356.
Schlichtkrull, J., "Insulin Crystals", Acta Chemica Scandinavica, 1956, vol. 10, No. 9, pp. 1455-1458.
Vajo et al., "Genetically Engineered Insulin Analogs: Diabetes in the New Millennium," Pharma Rev, 2000, vol. 52, No. 1, pp. 1-9.
Whittingham, J.L. et al., "Crystallographic and Solution Studies of N-Lithocholyl Insulin: A New Generation of prolonged-Acting Human Insulins", Biochemistry, 2004, vol. 42, pp. 5987-5995.
Brange, J et al Diabetic Medicine Neutral Insulin Solutions Physically Stabilized by Addition of ZN2+, 1986, vol. 3, No. 6, pp. 532-536.
Jonassen, I. et al., Pharmaceutical Research 2006, vol. 23, No. 1, pp. 49-55.
Annual Review Endocrine Metabolism 2000, pp. 46-53.
Nathan, D. M. et al., "Management of Hyperglycemia in Type 2 Diabetes: a Consensus Algorithm for the Initiation and Adjustment of Therapy," Diabetes Care, 2008, vol. 31, No. 1, pp. 173-175.
Heise, T. et al., "Towards Peakless, Reproducible and Long-Acting Insulins. An Assessment of the Basal Analogues Based on Isoglycaemic Clamp Studies," Diabetes Obes Metab, 2007, vol. 9, No. 5, pp. 648-659.
Hinds et al., "PEGylated insulin in PLGA microparticles. In vivo and in vitro analysis," Journal of Controlled Release, 2005, vol. 104, No. 3, pp. 447-460.
Heller. S R, Current Medical Research and Opinion, "Insulin Analogues", 2002, vol. 18, No. 1, pp. 40-47.
I. Jonassen et al., Diabetologia, "Insulin Degludec: Multi-Hexamer Formation is the Underlying Basis for This New Generation Ultra-Long Acting Basal Insulin", 2010, vol. 53, No. 1, pp. S388.
R. Cuddihy et al., Diabetologia, "Once-Daily Use of a New Generation Ultra-Long Acting Basal Insulin With a Bolus Boost in Insulin-Naïve People With Type 2 Diabetes: Comparison With Insulin Glargine", 2010, vol. 53, No. 1, pp. S389.
Samuel et al. "Studies on the immunogenicity of protamines in humans and experimental animals by means of a micro-complement fixation test." Clin. Exp. Immunol. vol. 33: pp. 252-260. 1978.
Kurtz et al. "Circulating IgG antibody to protamine in patients treated with protamine-insulins." Diabetologica. vol. 25: pp. 322-324. 1983.
Definition of Moiety From http://dictionary.reference.com/browse/moiety, Aug. 26, 2010, pp. 1-3.
R. Cuddihy et al., "Once-Daily Use of a New Generation Ultra-Long Acting Basal Insulin With a Bolus Boost in Insulin-Naïve People With Type 2 Diabetes: Comparison With Insulin Glargine", Diabetologia, 2010, vol. 53, No. 1, pp. S389.
I. Jonassen et al., "Insulin Degludec: Multi-Hexamer Formation is the Underlying Basis for This New Generation Ultra-Long Acting Basal Insulin", Diabetologia, 2010, vol. 53, No. 1, pp. S388.
I. Jonassen et al., "Insulin Degludec: Multi-Hexamer Formation is the Underlying Basis for This New Generation Ultra-Long Acting Basal Insulin", Diabetologia, Sep. 2010, vol. 53, No. 1, pp. S388.
R. Cuddihy et al., "Once-Daily Use of a New Generation Ultra-Long Acting Basal Insulin With a Bolus Boost in Insulin-Naïve People With Type 2 Diabetes: Comparison With Insulin Glargine" Diabetologia, Sep. 2010, vol. 53, No. 1, pp. S389.
American Diabetes Association, Standards of Medical Care in Diabetes 2012, Diabetes Care 2012, vol. 35(Suppl 1), pp. S11-S63.
American Diabetes Association. Insulin administration. Diabetes Care. 2012 vol. 35, No. 1, pp. S1-S2.
American Diabetes Association. Standards of Medical Care in Diabetes—2014. Diabetes Care. 2014, vol. 37 Suppl 1, pp. S14-S80.
Anderson RM et al. Patient empowerment: results of a randomized controlled trial. Diabetes Care. 1995, vol. 18, No. 7 pp. 943-949.
Barnett et al: Dosing of insulin glargine in the treatment of type 2 diabetes , Clinical Therapeutics, 2007 vol. 29, No. 6,, pp. 987-999.
Benjamin EM. Self-monitoring of blood glucose: the basics. Clinical Diabetes. 2002, vol. 20, No. 1, pp. 45-47.
Canadian Diabetes Association Clinical Practice Guidelines Expert Committee. Canadian Diabetes Association. Canadian Journal of Diabetes. 2008, vol. 32(Suppl 1)pp. S1-S201.

(56) References Cited

OTHER PUBLICATIONS

Davies M, et al.. Improvement of glycemic control in subjects with poorly controlled type 2 diabetes. Diabetes Care. 2005, vol. 28, No. 6, pp. 1282-1288.
Deutsch T et al, Utopia: a Consultation System for Visit-By-Visit Diabetes Management, Medical Informatica. Taylor and Francis.; Basingstoke. GB, 1996, vol. 21, No. 4, pp. 345-358.
Duckworth W. et al. Glucose Control and Vascular Complications in Veterans with Type 2 Diabetes, The new england journal of medicine, 2009, vol. 360, pp. 129-139.
Gerstein H C et al. A randomized trial of adding insulin glargine vs.avoidance of insulin in people with Type 2 diabetes on either no oral glucose-lowering agents or submaximal doses of metformin and/or sulphonylureas. The Canadian INSIGHT (Implementing New Strategies with Insulin Glargine for Hyperglycaemia treatment) Study, Diabetic Medicines, 2006, vol. 23, No. 7, pp. 736-742.
Holman RR et al., 10-Year Follow-up of Intensive Glucose Control in Type 2 Diabetes, The New England Journal of Medicine, 2008, vol. 359, pp. 1577-1589.
Holman RR et al. A practical guide to Basal and Prandial Insulin therapy, Diabetic Medicine, 1985, vol. 2, pp. 45-53.
International Diabetes Federation Clinical Guidelines Task Force. Global Guideline for Type 2 Diabetes. 2005. Available at: http://www.idf.org/webdata/docs/IDF%20GGT2D.pdf. Accessed Dec. 19, 2012.
Inzucchi SE et al. Management of Hyperglycemia in Type 2 Diabetes: A Patient-Centered Approach: Position Statement of the American Diabetes Association (ADA) and the European Association for the Study of Diabetes (EASD), Diabetes care, 2012, vol. 35, pp. 1364-1379.
Wamoto Yasuhi Ko et al: Insulin degludec in Japanese patients with type 1 diabetes mellitus: A randomized controlled trial, Journal of Diabetes Investigation,2013, vol. 4, No. 1, pp. 62-68.
Janka Hans U et al, Combination of oral antidiabetic agents with basal insulin; versus premixed insulin alone in randomized elderly patients with type 2 diabetes mellitus, Journal of the American Geriatrics Society, 2007, vol. 55, No. 2, pp. 182-188.
Kulzer B, et al. Effects of self-management training in type 2 diabetes: a randomized, prospective trial. Diabetic Medicine. 2007, vol. 24, No. 4, pp. 415-423.
Lantus® (insulin glargine [rDNA origin] injection). sanofi-aventis U.S. LLC, Bridgewater, NJ, USA; 2007. Health Care Professional. Dosing & Titration. Available at: http://www.lantus.com/hcp/titration.aspx. Accessed Nov. 13, 2012.
Liebl A, et al. Direct costs and health-related resource utilisation in the 6 months after insulin initiation in German patients with type 2 diabetes mellitus in 2006: Instigate study. Current Medical Research Opinion 2008, vol. 24, No. 3, pp. 2349-2358.
Meneghini L et al., The usage of a simplified self-titration dosing guideline (303 Algorithm) for insulin detemir in patients with type 2 diabetes-results of the randomized, controlled Predictive TM 303 study. Diabetes Obesity and Metabolism. 2007, vol. 9, pp. 902-913.
Nathan DM et al, Intensive Diabetes Treatment and Cardiovascular Disease in Patients with Type 1 Diabetes, The new england journal of medicine, 2005, vol. 353, No. 25, pp. 2643-2653.
Nathan DM et al. Management of Hyperglycemia in Type 2 Diabetes: A Consensus Algorithm for the Initiation and Adjustment of Therapy: Update regarding thiazolidinediones: a consensus statement from the American Diabetes Association and the European Association for the Study of Diabetes. Diabetes Care, 2008, vol. 31, No. 1, pp. 173-175.
Nathan DM et al. The Effect of Intensive Treatment of Diabetes on the Development and Progression of Long-Term Complications in Insulin-Dependent Diabetes Mellitus, the Diabetes Control and Complications Trial Research Group, The New England Journal of medicine, 1993, vol. 329, No. 14, pp. 977-986.
Norris SL, et al. Self-management education for adults with type 2 diabetes: a meta-analysis on the effect of glycemic control. Diabetes Care, 2002, vol. 25, No. 7, pp. 1159-1171.

Ohkubo Y et al. Intensive insulin therapy prevents the progression of diabetic microvascular complications in Japanese patients with non-insulin-dependent diabetes mellitus: a randomized prospective 6-year study, Diabetes Research and Clinical Practice, 1995, vol. 28, No. 2 pp. 103-117.
Peyrot M, et al. Factors associated with injection omission/non-adherence in the Global Attitudes of Patients and Physicians in Insulin Therapy Study. Diabetes Obesity and Metabolism. 2012, vol. 14, pp. 1081-1087.
Peyrot M, et al.. Insulin adherence behaviours and barriers in the multinational Global Attitudes of Patients and Physicians in insulin therapy study. Diabetic Medcine. 2012, vol. 29, No. 5, pp. 682-689.
Philis-Tsimikas A et al.: Insulin degludec once-daily in type 2 diabetes:; Simple or step-wise titration (Begin: Once Simple Use), Advances in Therapy, 2013, vol. 30, No. 6, pp. 607-622.
Sakharova O V et al. Effects on post-prandial glucose and Age precursors from two initial insulin strategies in patients with Type 2 diabetes uncontrolled by oral agents, Journal of Diabetes and Its Complications, 2012, vol. 26, No. 4, pp. 333-338.
Schnell O, et al. Consensus statement on self-monitoring of blood glucose in diabetes. Diabetes, Stoffwechsel und Herz. 2009, vol. 4, pp. 285-289.
Selvin E et al., Meta-Analysis: Glycosylated Hemoglobin and Cardiovascular Disease in; Diabetes Mellitus, Annals of Internal medicine, 2004, vol. 141, pp. 421-431.
The Advance Collaborative Group, Patel A et al. Intensive Blood Glucose Control and Vascular Outcomes in Patients with Type 2 Diabetes, The new England Journal of Medicine, 2008, vol. 358, pp. 2560-2572.
UK Prospective Diabetes Study (UKPDS) Group, Intensive blood-glucose control with sulphonylureas or insulin compared with conventional treatment and risk of complications in patients with type 2 diabetes (UKPDS 33)., Lancet, 1998, vol. 352 (9131), pp. 837-853.
Yeaw J, et al. Cost of self-monitoring of blood glucose in Canada among patients on an insulin regimen for diabetes. Diabetes Therapeutics . Epub ,2012 vol. 3, No. 7, pp. 1-17 doi: 10.1007/s13300-012-0007-6.
Yeaw J, et al. Self-monitoring blood glucose test strip utilization in Canada. Diabetes. 2012; vol. 61(Suppl 1)p. A35.
Yeaw J, et al.. Cost of self-monitoring of blood glucose in the United States among patients on an insulin regimen for diabetes. Journal of Managed Care Pharmacy 2012, vol. 18, No. 1, pp. 21-32.
American Diabetes Association. Insulin administration. Diabetes Care. 2002 vol. 25: pp. S112-S115.
Heise T, et al.. Insulin degludec: four times lower pharmacodynamic variability than insulin glargine under steady-state conditions in type 1 diabetes. Diabetes Obesity and Metabolism , 2012, vol. 14, pp. 859-864.
Heise T, et al. Insulin degludec 200 U/mL is ultra-long-acting and has a flat and stable glucose-lowering effect. Diabetes.2012;, vol. 61(Suppl. 1) p. A91.
Korsatko S, et al. Ultra-long-acting insulin degludec: bio-equivalence and similar pharmacodynamics shown for two different formulations (U100 and U200). Diabetologia. 2011 , vol. 54(Suppl. 1) p. S427.
World Medical Association. World Medical Association Declaration of Helsinki: Ethical principles for medical research involving human subjects—Last amended by the 59th WMA General Assembly, Seoul. 2008. Available at: http://www.wma.net/en/30publications/10policies/b3/17c.pdf. Accessed Sep. 14, 2015.
International Conference on Harmonisation. ICH Harmonised Tripartite Guideline:Guideline for Good Clinical Practice. E6 (R1), Step 4. 1996. Available at: http://www.ich.org/fileadmin/Public_Web_Site/ICH_Products/Guidelines/Efficacy/E6_R1/Step4/E6_R1_Guideline.pdf. Accessed Sep. 14, 2015.
Niskanen L, et al. Randomized, multinational, open-label, 2-period, crossover comparison of biphasic insulin aspart 30 and biphasic insulin lispro 25 and pen devices in adult patients with type 2 diabetes mellitus. Clinical Therapeutics 2004, vol. 26 pp. 531-540.
Garg S, et al. Preference for a new prefilled insulin pen compared with the original pen. Current Medical Research & Opinion. 2011 vol. 27 pp. 2323-2333.

(56) References Cited

OTHER PUBLICATIONS

Garber AJ, et al; on behalf of the NN1250-3582 Begintm BB T2D trial investigators. Insulin degludec, an ultra-long acting basal insulin, versus insulin glargine in basal-bolus treatment with mealtime insulin aspart in type 2 diabetes (Begintm Basal-Bolus Type 2): a phase 3, randomised, open-label, treat-to-target non-inferiority trial. Lancet.2012, vol. 379, pp. 1498-1507.

Zinman B, et al; on behalf of the NN1250-3579 Begin tm Once Long trial investigators. Insulin degludec versus insulin glargine in insulin-naïve patients with type 2 diabetes: a 1-year, randomized, treat-to-target trial (Begin tm Once Long). Diabetes Care. 2012 vol. 35 pp. 2464-2471.

Bergenstal R, Bhargava A, Jain RK, et al; on behalf of the NN1250-3672 Begin TM Low Volume trial investigators. 200 U/ml insulin degludec improves glycemic control similar to insulin glargine with a low risk of hypoglycemia in insulin-naïve people with type 2 diabetes. Abstract 207. http://am.aace.com/2012/sites/all/files/abstract-061812.pdf. Accessed Jan. 19, 2013.

Onishi Y, et al. Superior glycaemic control with once daily insulin degludec/ insulin aspart versus insulin glargine in Japanese adults with type 2 diabetes inadequately controlled on oral drugs: a randomized, controlled phase 3 trial. Diabetes Obesity and Metabolism. 2013 vol. 15, pp. 826-832.

Rakel RE. Improving patient acceptance and adherence in diabetes management: a focus on insulin therapy. Advances in Therapy. 2009, vol. 26 pp. 838-846.

Ross SA, et al. Barriers to effective insulin treatment: the persistence of poor glycemic control in type 2 diabetes. Current Medical Research and Opinion 2011, vol. 27(Suppl 3), pp. 13-20.

Reimer T, et al. Intuitiveness, instruction time, and patient acceptance of a prefilled insulin delivery device and a reusable insulin delivery device in a randomized, open-label, crossover handling study in patients with type 2 diabetes. Clinical Therapeutics. 2008, vol. 30, pp. 2252-2262.

Brange "Stability of Insulin", 1994, Kluwer Academic Publishers BV, pp. 30-31.

Birkeland et al. "Insulin degludec in type 1 diabetes: a randomized controlled trial of a new-generation ultra-long-acting insulin compared with insulin glargine." Diabetes Care, Mar. 2011, vol. 34, No. 3, p. 661-665.

Briscoe et al., "Hypoglycemia in type 1 and type 2 diabetes: physiology, pathophysiology, and management." Clinical diabetes, Jul. 2006, vol. 24, No. 3, pp. 115-121.

U.S. Appl. No. 16/463,594, filed May 23, 2019.

Le Tourneau, et al., "Dose escalation methods in phase 1 cancer clinical trials." JNCI: Journal of the National Cancer Institute, May 2009, vol. 101, No. 10, pp. 708-720.

American Diabetes Association, "Standards of Medical Care in Diabetes—2012," Diabet. Care., 2012, vol. 35(Suppl 1), pp. S11-S63.

American Diabetes Association, "Introduction," Diabetes Care, Jan. 2012, vol. 35(Suppl. 1), pp. S1-S2.

American Diabetes Association, "Standards of Medical Care in Diabetes—2014," Diabetes Care, Jan. 2014, vol. 37, Suppl. 1.

American Diabetes Association, "Insulin Administration," Diabetes Care, Jan. 2002, vol. 25(suppl 1), pp. S112-S115.

Anderson et al., "Patient empowerment: results of a randomized controlled trial," Diabetes Care, Jul. 1995, vol. 18, No. 7, pp. 943-949.

Benjamin EM, "Self-monitoring of blood glucose: the basics," Clin Diabetes, Jan. 2002, vol. 20, No. 1, pp. 45-47.

Canadian Diabetes Association Clinical Practice Guidelines Expert Committee, Canadian Diabetes Association, Can J Diabetes, Sep. 2008; vol. 32(Suppl 1), pp. S1-S201.

Davies et al., "Improvement of glycemic control in subjects with poorly controlled type 2 diabetes," Diabet. Care., Jun. 2005, vol. 28, pp. 1282-1288.

Duckworth et al., "Glucose control and vascular complications in veterans with type 2 diabetes," N Engl J Med, 2009, vol. 360, pp. 129-139.

Gerstein et al., "A randomized trial of adding insulin glargine vs. avoidance of insulin in people with Type 2 diabetes on either no oral glucose-lowering agents or submaximal doses of metformin and/or sulphonylureas. The Canadian INSIGHT (Implementing New Strategies with Insulin Glargine for Hyperglycaemia Treatment) Study," Diabet. Med., May 2006, vol. 23, No. 7, pp. 736-742.

Holman et al., "10-year follow-up of intensive glucose control in type 2 diabetes," N Engl J Med, 2008, vol. 359, pp. 1577-1589.

Holman et al., "A practical guide to basal and prandial insulin therapy," Diabet. Med., Jan. 1985, vol. 2, No. 1, pp. 45-53.

International Diabetes Federation Clinical Guidelines Task Force, "Global Guideline for Type 2 Diabetes," 2005.

Inzucchi et al., "Management of hyperglycemia in type 2 diabetes: a patient-centered approach: position statement of the American Diabetes Association (ADA) and the European Association for the Study of Diabetes (EASD)," Diabetes Care. Jun. 2012, vol. 35, pp. 1364-1379.

Kulzer et al., "Effects of self-management training in type 2 diabetes: a randomized, prospective trial," Diabet. Med., Feb. 2007, vol. 24, pp. 415-423.

Lantus® (insulin glargine [rDNA origin] injection), Sanofi-aventis U.S. LLC, Bridgewater, NJ, USA; 2007, Health Care Professional, Dosing & Titration, accessed Jan. 17, 2019.

Liebl et al., "Direct costs and health-related resource utilisation in the 6 months after insulin initiation in German patients with type 2 diabetes mellitus in 2006: Instigate study," Curr Med Res Opin, Jul. 2008, vol. 24, No. 8, pp. 2349-2358.

Meneghini et al., "The usage of a simplified self-titration dosing guideline (303 Algorithm) for insulin detemir in patients with type 2 diabetes—results of the randomized, controlled Predictivetm 303 study." Diabet. Obes. Metab., Oct. 2007, vol. 9, pp. 902-913.

Nathan et al., "'Intensive Diabetes Treatment and Cardiovascular Disease in Patients with Type 1 Diabetes,'" N Engl. J Med., Dec. 2005, vol. 353, No. 25, pp. 2643-2653.

Nathan et al., "Management of hyperglycemia in type 2 diabetes: a consensus algorithm for the initiation and adjustment of therapy: update regarding thiazolidinediones: a consensus statement from the American Diabetes Association and the European Association for the Study of Diabetes," Diabetes Care, 2008, vol. 31, No. 1, pp. 173-175.

Norris et al., "Self-management education for adults with type 2 diabetes: a meta-analysis on the effect of glycemic control," Diabetes Care, Jul. 2002, vol. 25, pp. 1159-1171.

Ohkubo et al., "Intensive insulin therapy prevents the progression of diabetic microvascular complications in Japanese patients with non-insulin-dependent diabetes mellitus: a randomized prospective 6-year study," Diabetes Res. Clin. Pract., 1995, vol. 28, pp. 103-117.

Patel et al. "Intensive blood glucose control and vascular outcomes in patients with type 2 diabetes," N Engl. J Med, 2008, vol. 358, pp. 2560-2572.

Peyrot et al., "Factors associated with injection omission/nonadherence in the Global Attitudes of Patients and Physicians in Insulin Therapy Study," Diabet. Obes. Metab., Jun. 2012, vol. 14, pp. 1081-1087.

Peyrot et al., "Insulin adherence behaviors and barriers in the multinational Global Attitudes of Patients and Physicians in insulin therapy study," Diabet. Med., Feb. 2012, vol. 29, pp. 682-690.

Philis-Tsimikas et al, Insulin Degludec Once-Daily in Type 2 Diabetes: Simple or Step-Wise Titration (Begin: Once Simple Use), Advances in Therapy, Jun. 2013, vol. 30, No. 6, pp. 607-622.

Schnell et al., "Consensus statement on self-monitoring of blood glucose in diabetes," Diabetes, Stoffwechsel und Herz, Jul. 2009, vol. 4, pp. 285-289.

Selvin et al., "'Meta-Analysis: Glycosylated Hemoglobin and Cardiovascular Disease in Diabetes Mellitus,'" Ann. Intern. Med., Sep. 2004, vol. 141, pp. 421-431.

The Diabetes Control and Complications Trial Research Group, "The effect of intensive treatment of diabetes on the development and progression of long-term complications in insulin-dependent diabetes mellitus," N Engl J Med, 1993, vol. 329, No. 14, pp. 977-986.

UK Prospective Diabetes Study (UKPDS) Group, "Intensive blood-glucose control with sulphonylureas or insulin compared with

(56) References Cited

OTHER PUBLICATIONS conventional treatment and risk of complications in patients with type 2 diabetes (UKPDS 33)," Lancet, 1998, vol. 352, pp. 837-853.
Yeaw et al., "Cost of self monitoring of blood glucose in Canada among patients on an insulin regimen for diabetes," Diabetes Ther. Epub Jun. 27, 2012, vol. 3, pp. 1-17.
Yeaw et al., "Cost of self-monitoring of blood glucose in the United States among patients on an insulin regimen for diabetes," J Manag. Care Pharm., Jan. Feb. 2012, vol. 18, pp. 21-32.
Yeaw et al., "Self-monitoring blood glucose test strip utilization in Canada," Diabetes, Jun. 2012, vol. 61(Suppl 1), p. A35.
Selvin et al., ""Meta-Analysis: Glycosylated Hemoglobin and Cardiovascular Disease in Diabetes Mellitus,"" Ann. Intern. Med., Sep. 2004, vol. 141, No. 6, pp. 421-431.

300

(302) A device for providing a long-acting or ultra-long-acting insulin dose guidance recommendation for a subject to treat diabetes mellitus. The device includes one or more processors and a memory. The memory includes instructions that, when executed by the one or more processors, perform a method responsive to receiving a dose guidance request (304) The long-acting or ultra-long-acting insulin has a structure of structure (I)

(306) The long-acting or ultra-long-acting insulin is LysB29(Nc-hexadecandioyl-y-Glu) des(B30) human insulin (insulin degludec, Tresiba®)

(308) The long-acting insulin or ultra-long-acting insulin is selected from the group consisting of a) neutral protamine hagedorn insulin (NHP insulin) (Humulin® N, Novolin® ge NPH), b) Lente Insulin (Humulin® L, Novolin® ge Lente), c) Ultralente Insulin (Humulin® U, Novolin1M ge Ultralente), d) Glargine Insulin (Lantus®), e) Detemir Insulin (Levemir®), f) Hypurin Bovine Lente, and g) Hypurin Bovine PZI (310) The long-acting or ultra-long-acting insulin for use is administered, either concurrently or consecutively, together with one or more additional drugs used in the treatment of diabetes (312) The one or more additional drug used in the treatment of diabetes is, or includes, a drug selected from the group consisting of: insulins, sensitizers (such as biguanides and thiazolidinediones), secretagogues (such as sulfonylureas and nonsulfonylurea secretagogues), alpha-glucosidase inhibitors and peptide analogs (such as injectable incretin mimetics, gastric inhibitory peptide analogs, dipeptidyl peptidase-4 inhibitors and injectable amylin analogues)

(313) The long-acting or ultra-long-acting insulin is LysB29(Nc-hexadecandioyl-y-Glu) des(B30) human insulin (insulin degludec, Tresiba®), and the long-acting or ultra-long-acting insulin is administered, concurrently or consecutively, with liraglutide (314) The diabetes mellitus is type 2 diabetes mellitus (A)

(316) The long-acting or ultra-long-acting insulin dose guidance recommendation is to achieve a specific glucose target (318) The device further comprises a wireless receiver, and wherein the first data set is obtained wirelessly from a glucose sensor affixed to the subject and/or the second data set is obtained wirelessly from the one or more insulin pens (320) Obtain a first data structure that includes at least (i) a body weight of the subject, (ii) an upper limit target glucose range of the subject, (iii) a lower limit target glucose range of the subject, and (iv) an overbasalisation limit of the subject (322) The overbasalisation limit is at least within 1.0-0.5 units/kg, 1.5-1.0 units/kg, 0.75-0.25 units/kg, 0.5-0 units/kg, or 2.0-0.75 units/kg (324) Obtain a second data structure that includes at least (i) a most recent adjustment day dose recommendation (ADDR) and/or (ii) a starting basal dose (SBD)

(326) Update the starting basal dosage at least within the immediately preceding 1 day, the immediately preceding 4 days, the immediately preceding 7 days, or the immediately preceding 10 days (328) Obtain a first data set, comprising a plurality of glucose measurements of the subject taken over a time course to establish a blood glucose history and, for each respective glucose measurement in the plurality of glucose measurements, a corresponding glucose timestamp representing when in the time course the respective glucose measurement was made (330) The time course comprises a current day and the past four days (B)

Fig. 3B (328 continued)

B (332) The time course comprises the current day and between one and ten of the immediately preceding past days (333) When the blood glucose history time course contains a gap, calculate a reconstructed blood glucose history based on the blood glucose history of each calendar day (334) Perform a quality check of the reconstructed blood glucose history data, and when the data quality check fails, the dose guidance recommendation is not updated (335) Store the updated blood glucose history in the first data structure (336) Obtain a second data set, comprising (i) a basal insulin injection history of the subject, wherein the injection history comprises a plurality of injections during all or a portion of the time course and, for each respective injection in the plurality of injections, (ii) a corresponding dose event amount and (iii) a dose event timestamp representing when in the time course the respective injection event occurred and wherein the second data set further comprises (iv) a last injection data refresh of the subject (338) Update the last injection data refresh within the immediately preceding 30 seconds or less, the immediately preceding 1 minute or less, or the immediately preceding 5 minutes or less (340) Update the last injection data refresh within the immediately preceding 30 seconds or less, the immediately preceding 1 minute or less, or the immediately preceding 5 minutes or less (342) Combine any injections in the injection history that have timestamps within a five-minute period in the time course into one injection

(344) Evaluate at least the first data structure, the second data structure, the first data set, and the second data set to determine whether they collectively contain a set of evaluation information comprising at least (i) the body weight of the subject, (ii) the plurality of glucose measurements of the subject taken over the time course, (iii) the injection history of the subject, (iv) the last adjustment day dose recommendation and/or the starting long-acting or ultra-long-acting insulin dose of the subject, (v) the overbasalisation limit of the subject, (vi) the last injection data refresh for the subject, (vii) the upper limit target glucose range of the subject, and (viii) the lower limit target glucose range of the subject (346) Provide the long-acting or ultra-long-acting insulin dose guidance recommendation when a determination is made that the at least first data structure, second data structure, first data set, and second data set collectively do contain the set of evaluation information (348) When a determination is made that the at least first data structure, second data structure, first data set, and second data set fail to collectively contain the set of evaluation information, no update to the long-acting or ultra-long-acting insulin dose guidance recommendation is made (350) Update the dose guidance recommendation for the subject, unless the injection history of the subject comprises one or more injections of the subject that have injection timestamps within the immediately preceding 4 hours or less, the immediately preceding 8 hours or less, the immediately preceding 12 hours or less, or the immediately preceding 16 hours or less (352) Update the dose guidance recommendation for the subject, unless the injection history of the subject comprises one or more injections of the subject that have injection timestamps within the current day (354) Update the dose guidance recommendation for the subject when at least one injection occurred within the current day and no injections occurred in the immediately preceding one day in the injection history time course

Fig. 3D

(356) Provide a re-recommendation of the dose guidance recommendation (358) Do not provide a re-recommendation until (i) three or more injections with an injection amount equivalent to the dose guidance baseline have occurred, (ii) three or more injections have occurred since the dose guidance baseline and when three or more injections have occurred over the current day and the past four days, and/or (iii) three or more does events with an injection amount greater than or equal to the dose guidance baseline have occurred

(360) Calculate a daily titration glucose level and an overall titration glucose level (362) The daily titration glucose level for each calendar day is calculated by selecting the lowest average of reconstructed blood glucose history data for any predetermined first time period within the injection history time course and excluding any reconstructed blood glucose history data with a timestamp older than the timestamp of the dose guidance baseline (364) When there are gaps larger than a second predetermined time period in the injection history time course, no daily titration glucose level is calculated (366) The predetermined second time period is between 10 minutes and 40 minutes (368) When there are gaps larger than a second predetermined time period in the injection history time course, no daily titration glucose level is calculated (370) The predetermined third time period is between 1 hour and 5 hours

(372) When there are gaps in the injection history time course and these gaps are at least the predetermined second time period in length and less than a predetermined third time period in length within any calendar day in the injection history time course, the daily titration glucose level averaging omits any predetermined first time period containing gaps when averaging the reconstructed blood glucose history data (374) The predetermined number of blood glucose measurements is between 20 and 100

(376) When any calendar day in the injection history time course contains gaps longer than the predetermined third time period or when more than a predetermined number of blood glucose measurements are absent no daily titration glucose level is calculated (378) The predetermined first time period is between 15 minutes and 120 minutes (380) The overall titration glucose level is calculated by taking the average of the daily titration glucose levels, and wherein when no overall titration glucose level can be determined the dose guidance recommendation is not updated

(382) Responsive to receiving a request for an updated adjustment day dose recommendation, perform a new recommendation procedure to determine the injection amount for the updated adjustment day dose recommendation wherein the updated adjustment day dose recommendation function is based upon at least a titration glucose level and a max basal limit (384) The titration glucose level comprises one of (i) the overall titration glucose level is greater than the upper limit target glucose range, (ii) the overall titration glucose level is greater than or equal to the lower target glucose range and the overall titration glucose level is less than or equal to the upper limit target glucose range, and/or (iii) the daily titration glucose level is less than the lower target glucose range (385) The upper limit target glucose range used to determine the updated adjustment day dose recommendation is within 80-180mg/dL, 90-180 mg/dL, 100-180mg/dL, 90-200mg/dL, 90-250mg/dL or 90-300mg/dL (386) The lower target glucose range used to determine the updated adjustment day dose recommendation is within 50-70mg/dL, 71-90 mg/dL, 71-100mg/dL, or 61-90mg/dL (388) The max basal limit consists of the overbasalisation limit multiplied by the body weight of the subject (390) When the overall titration glucose level is greater than the upper limit target glucose range of the subject and when the most recent adjustment day dose recommendation is less than the max basal limit of the subject, then the updated adjustment day dose recommendation is determined to be the determined dose guidance baseline plus a predetermined number of units of long-acting or ultra-long-acting insulin (391) The predetermined number of units of long-acting or ultra-long-acting insulin by which to alter the adjustment day dose recommendation is selected from the set of at least 1 unit, 2 units, 4 units, and 6 units

(392) When the overall titration glucose level is greater than the upper limit target glucose range of the subject and when the most recent adjustment day dose recommendation is greater than or equal to the max basal limit of the subject, then the updated adjustment day dose recommendation is determined to be the determined dose guidance baseline (394) When the overall titration glucose level is between the upper limit target glucose range of the subject and the lower target glucose range of the subject, then the updated adjustment day dose recommendation is determined to be the determined dose guidance baseline (396) When the daily titration glucose level is less than the lower target glucose range of the subject, then the updated adjustment day dose recommendation is determined to be the determined dose guidance baseline minus a predetermined number of units of long-acting or ultra-long-acting insulin (397) The predetermined number of units of long-acting or ultra-long-acting insulin by which to alter the adjustment day dose recommendation is selected from the set of at least 1 unit, 2 units, 4 units, and 6 units (398) Provide the updated adjustment day dose recommendation at least with the immediately preceding 1 day, the immediately preceding 4 days, the immediately preceding 7 days, or the immediately preceding 10 days

Fig. 3H

SYSTEM FOR PROVIDING AN UP-TO-DATE AND LONG-ACTING OR ULTRA-LONG-ACTING INSULIN DOSE GUIDANCE RECOMMENDATION TO TREAT DIABETES MELLITUS

CROSS-REFERENCE TO RELATED APPLICATIONS

This application is a continuation of U.S. application Ser. No. 16/020,478, filed Jun. 27, 2018, which claims priority under 35 U.S.C. § 119 of U.S. Provisional Application 62/690,157, filed Jun. 26, 2018; the contents of which are incorporated herein by reference.

TECHNICAL FIELD

The present disclosure relates generally to systems and methods for assisting patients and health care practitioners in managing insulin treatment to diabetes, in which pre-scribed basal injections are titrated based on data sets of blood glucose or continuous glucose, where a target fasting blood glucose target is adapted to estimated risk of hypo- and hyperglycemia.

BACKGROUND

Diabetes mellitus (DM) is impaired insulin secretion and variable degrees of peripheral insulin resistance leading to hyperglycemia. Type 2 diabetes mellitus is characterized by progressive disruption of normal physiologic insulin secretion. In healthy individuals, basal insulin secretion by pancreatic β cells occurs continuously to maintain steady glucose levels for extended periods between meals. Also in healthy individuals, there is prandial secretion in which insulin is rapidly released in an initial first-phase spike in response to a meal, followed by prolonged insulin secretion that returns to basal levels after 2-3 hours. Years of poorly controlled hyperglycemia can lead to multiple health complications. Diabetes mellitus is one of the major causes of premature morbidity and mortality throughout the world.

Effective control of blood/plasma glucose can prevent or delay many of these complications but may not reverse them once established. Hence, achieving good glycemic control in efforts to prevent diabetes complications is the primary goal in the treatment of type 1 and type 2 diabetes. Smart titrators with adjustable step size and physiological parameter estimation and pre-defined fasting blood glucose target values have been developed to administer insulin medicament treatment regimens.

Studies also support the role of glycated hemoglobin ($HbA_{1c}$) reduction in decreasing cardiovascular disease risk (Nathan et al. N Engl. J Med. 2005. 353:2643-2653; Selvin et al. Ann. Intern. Med. 2004. 141:421-431). The general goal of an $HbA_{1c}$ level of below 7% has been recommended by many diabetes organizations (e.g., the American Diabetes Association (ADA)). In the (UK Prospective Diabetes Study (UKPDS) Group, 50% of patients were taking insulin therapy to maintain $HbA_{1c}$ levels of below 7% within 6 years of the diagnosis of type 2 diabetes.

There are numerous non-insulin treatment options for diabetes, however, as the disease progresses, the most robust response will usually be with insulin. In particular, since diabetes is associated with progressive β-cell loss many patients, especially those with long-standing disease, will eventually need to be transitioned to insulin since the degree of hyperglycemia (e.g., $HbA_{1c} \geq 8.5\%$) makes it unlikely that another drug will be of sufficient benefit.

Most patients express reluctance to beginning injectable therapy, due to discomfort and inconvenience caused by the high demands for blood glucose testing and insulin injection. Traditionally, the use of insulin to improve glycemic control was provided by medical specialists. With the increasing number of patients under primary care for whom insulin is indicated, prescribing it in the same setting appears much more convenient for the end users. Often however, insulin is not started in time, due to psychological resistance from both doctors and patients.

A consensus statement from the American Diabetes Association (ADA) and the European Association for the Study of Diabetes (EASD) was updated in 2012, and emphasized a patient-centered approach and individualized $HbA_{1c}$ treatment targets for the management of hyperglycemia in type 2 diabetes (T2DM). It recommended that insulin could be considered as one of the options for dual combination therapy, if an individualized $HbA_{1c}$ level target was not reached after metformin therapy. This choice could be based on patient and drug characteristics, with an over-riding goal of improving glycemic control while minimizing side-effects. When three-drug combinations are considered, insulin is likely to be more effective than most other agents (e.g., sulfonylurea, thiazolidinedione, dipeptidyl peptidase 4 inhibitor, glucagon-like peptide-1 receptor agonist), especially when the $HbA_{1c}$ level is very high ($\geq 9.0\%$) (Inzucchi et al., Management of hyperglycemia in type 2 diabetes: a patient-centered approach: position statement of the American Diabetes Association (ADA) and the European Association for the Study of Diabetes (EASD). Diabetes Care 2012. 35:1364-79).

The ideal insulin regimen aims to mimic the physiological profile of insulin secretion as closely as possible. There are two major components in the insulin profile: a continuous basal secretion and prandial surge after meals. The basal secretion controls overnight and fasting glucose while the prandial surges control postprandial hyperglycemia.

Based on the time of onset and duration of their actions, injectable formulations can be broadly divided into basal (long-acting analogues [e.g., insulin detemir and insulin glargine] and ultra-long-acting analogues [e.g., insulin degludec]) and intermediate-acting insulin [e.g., isophane insulin] and prandial (rapid-acting analogues [e.g., insulin aspart, insulin glulisine and insulin lispro]). Premixed insulin formulations incorporate both basal and prandial insulin components.

There are various recommended insulin regimes, such as (1) multiple injection regimen: rapid-acting insulin before meals with long-acting insulin once or twice daily; (2) premixed analogues or human premixed insulin once or twice daily before meals; (3) intermediate- or long-acting insulin once or twice daily. However, where possible, a long-acting insulin regimen alone or in combination with oral antidiabetic drug(s) (OADs) is usually the optimal initial regimen for subjects with T2DM as this reduces the patient burden and discomfort caused by blood glucose measurement and injection of insulin.

Recent data from the United Kingdom Prospective Diabetes Study suggest the importance of stringent glycemic control (Holman et al., 10-year follow-up of intensive glucose control in type 2 diabetes. N Engl J Med 2008; 359: 1577-1589) and current treatment guidelines call for early insulin treatment in type 2 diabetes patients (Nathan et al., Management of hyperglycemia in type 2 diabetes: a consensus algorithm for the initiation and adjustment of therapy: update regarding thiazolidinediones: a consensus statement from the American Diabetes Association and the European Association for the Study of Diabetes. Diabetes Care 2008; 31: 173-175). However, optimal initiation and titration methods for the long-acting basal insulins are still being determined. Evidence suggests that many patients often do not have insulin doses titrated sufficiently to achieve target levels of glucose control (remaining on suboptimal doses and failing to reach treatment targets) (UKPDS).

What has become increasingly clear is that patient empowerment is essential for motivation to reach treatment targets. Self-titration regimens facilitate empowerment of patients, allowing them to become more involved in their treatment, which can result in improved glycemic control. Until recently, titration of insulin in type 2 diabetes clinical trials was typically left up to the investigator's discretion with a simple statement of the target ranges for glucose. In type 2 diabetes trials the average glycemic control achieved was usually less than desirable. Since then a number of trials have been conducted and reported utilizing various algorithms under various conditions.

During the last decade various insulin titration algorithms have been applied in several trials initiating long or intermediate acting insulin in type 2 diabetes patients often referred to as Treat-to-target. Several of the trials were designed for other primary purposes than algorithm development and have therefore used one specific algorithm. Interpretation of algorithm merit in those cases is somewhat difficult and has to rely on cross trial comparisons. Various factors in addition to the numbers in the algorithm apparently affect the achieved results.

The algorithms for basal insulin titration and their implementation have evolved steadily further away from complete real time health care provider control over every dose decision. Health care provides have traditionally chosen a target titration level with respect to estimated insulin sensitivity and other factors determined in the clinic. Therefore, the target is not updated between visits to the health care practitioner based upon changes in physiological parameters, unexpected responsiveness to the drug or level of adherence, even though these are factors that affect the treatment outcome. The first step towards more flexible titration approaches was the acceptance of one algorithm for all patients, which at the time was considered radical by most investigators. The second step became acceptance algorithm enforcement.

Controlled clinical trials such as the Diabetes Control and Complications Trial (The effect of intensive treatment of diabetes on the development and progression of long-term complications in insulin-dependent diabetes mellitus. The Diabetes Control and Complications Trial Research Group. N Engl J Med 1993; 329:977-86), UKPDS (Intensive blood-glucose control with sulphonylureas or insulin compared with conventional treatment and risk of complications in patients with type 2 diabetes (UKPDS 33), UK Prospective Diabetes Study (UKPDS) Group. Lancet 1998; 352:837-53), the Veterans Affairs Diabetes Trial (Duckworth W, Abraira C, Moritz T, et al. Glucose control and vascular complications in veterans with type 2 diabetes. N Engl J Med 2009; 360:129-39), the Action in Diabetes and Vascular Disease: Preterax and Diamicron Modified Release Controlled Evaluation trial (ADVANCE Collaborative Group, Patel A, MacMahon S, et al. Intensive blood glucose control and vascular outcomes in patients with type 2 diabetes. N Engl. J Med 2008; 358:2560-72), and a study on Japanese patients (Ohkubo et al., Intensive insulin therapy prevents the progression of diabetic microvascular complications in Japanese patients with non-insulin-dependent diabetes mellitus: a randomized prospective 6-year study. Diabetes Res. Clin. Pract. 1995; 28:103-17) demonstrated that intensive glycemic control could significantly reduce the risk of microvascular complications.

Common to all basal insulin titration algorithms is that dose changes are based on averages of a varying number of days' morning fasting self-monitored blood or plasma glucose. From this general theme there are many variations.

The starting dose has been 10 U, 20 U, or based on the morning fasting plasma glucose (FPG) using the formula of Holman and Turner (Holman R R, Turner R C. A practical guide to basal and prandial insulin therapy. Diabet. Med. 1985 January; 2(1): 45-53) which is (FPG (mg/dl)—50)/10, typically yielding just short of 20 U. Within these options there does not appear to be any difference in achieved glycemic control and hypoglycemia rate.

When a clinic has to titrate the insulin dose for the individual patient, there is often a natural limitation on the possible frequency of changing the titration dose. Consequently, the clinic has to be able to make substantial dose increments at high average glucose so the patient is not left for too long a time in poor glycemic control. However, the patient alone can easily titrate often, for which there is a long tradition for those with type 1 diabetes. With more frequent titration there may be a reduced need for large dose steps at high glucose levels and the algorithms can be simplified in terms of number of steps.

Earlier titration protocols typically titrated an insulin dose based on the average of a week's worth of several fasting blood/plasma measurements. Later trials are based on dose titrations based on average fasting blood/plasma measurements based of 3 measurements per week.

At the extreme is INSIGHT (Gerstein et al., A randomized trial of adding insulin glargine vs. avoidance of insulin in people with Type 2 diabetes on either no oral glucose-lowering agents or submaximal doses of metformin and/or sulphonylureas. The Canadian INSIGHT (Implementing New Strategies with Insulin Glargine for Hyperglycaemia Treatment) Study. Diabet. Med. 2006; 23(7): 736-42), which has only one step of one unit of insulin titrated every morning by the patient.

Clinic contact initially occurred every other week, but after 4 weeks the clinic contact went to every 4 weeks and after 12 weeks to 6-week intervals. Clinic oversight was thus minimally if at all intensified compared to standard clinical practice. Patients were taught to "start with an initial dose of 10 units, and advised to increase this by 1 unit each day until achieving a FPG (FPG)≤5.5 mmol/liter (99 mg/dl)" The end insulin dose was 38 U and $HbA_{1c}$ 7.0%. From an effectiveness point of view, this is an "outstanding" result. Hence, there is a trend toward increasingly high frequency of insulin dose titration in order to improve to primary aim of insulin therapy—glycemic control.

Diabetes care guidelines and product labelling for current basal insulin analogs recommend regular blood glucose self-measurement (American Diabetes Association. Standards of Medical Care in Diabetes—2012. Diabet. Care. 2012; 35(Suppl 1): S11-63; International Diabetes Federation Clinical Guidelines Task Force. Global Guideline for Type 2 Diabetes. 2005. Available on the Internet at www.id-forg/webdata/docs/IDF %20GGT2D.pdf (Accessed Dec. 19 2012); Canadian Diabetes Association Clinical Practice Guidelines Expert Committee. Canadian Diabetes Association. Can J Diabetes. 2008; 32 (Suppl 1): S1-201; Meneghini et al., The usage of a simplified self-titration dosing guideline (303 Algorithm) for insulin detemir in patients with type 2 diabetes—results of the randomized, controlled PREDICTIVE™ 303 study. Diabet. Obes. Metab. 2007; 9:902-13; Davies et al., Improvement of glycemic control in subjects with poorly controlled type 2 diabetes. Diabet. Care. 2005; 28:1282-8; and LANTUS® (insulin glargine [rDNA origin] injection). Sanofi-aventis U.S. LLC, Bridgewater, NJ, USA; 2007. Health Care Professional. Dosing & Titration. Available on the Internet at www.lantus.com/hcp/titration.aspx. (Accessed Nov. 13, 2012) in order to help people with diabetes maintain appropriate glycemic control and become more actively involved in their healthcare (Benjamin E M. Self-monitoring of blood glucose: the basics. Clin Diabetes. 2002; 20(1):45-7; Schnell et al., Consensus statement on self-monitoring of blood glucose in diabetes. Diabetes, Stoffwechsel and Herz. 2009; 4:285-9; and American Diabetes Association. Insulin administration. Diabetes Care. 2012; 35:S1). Insulin dose is also typically determined and titrated up or down as needed according to algorithms based on blood glucose results (American Diabetes Association. Standards of Medical Care in Diabetes—2014. Diabetes Care. 2014; 37 Suppl. 1). Insulin dose determination is individual for each patient. The dose steps (titration model), the glycemic target as well as the absolute insulin dose are determined in an individualized and tailored manner for each individual generally by a healthcare provider (HCP).

Challenges exist that can prevent the achievement of glycemic targets with insulin, including perceptions on the part of patients and HCPs that insulin therapy can be burdensome or too complex to manage (Peyrot et al., Factors associated with injection omission/non-adherence in the Global Attitudes of Patients and Physicians in Insulin Therapy Study. Diabet. Obes. Metab. 2012; 14:1081-7; and Peyrot et al., Insulin adherence behaviors and barriers in the multinational Global Attitudes of Patients and Physicians in insulin therapy study. Diabet. Med. 2012; 29:682-90). Patients who take an active role in the management of their diabetes and titration of their insulin may feel more empowered to take charge of their self-care and have a stronger belief that their actions can influence their disease, thus leading to better treatment outcomes (Norris et al., Self-management education for adults with type 2 diabetes: a meta-analysis on the effect of glycemic control. Diabetes Care. 2002; 25:1159-71; Kulzer et al., Effects of self-management training in type 2 diabetes: a randomized, prospective trial. Diabet. Med. 2007; 24:415-23; Anderson et al. Patient empowerment: results of a randomized controlled trial. Diabetes Care. 1995; 18:943-9). In determining how self-care can best be facilitated for patients with diabetes, the cost and burden of frequent glucose testing must be considered when designing treatment plans, as these can be significant factors when added to the health, quality of life (QoL), and financial toll of poorly controlled diabetes.

Numerous studies investigating the cost of self-measured blood glucose (SMBG) testing have found that it includes a substantial portion of diabetes-related expenditures (Liebl et al., Direct costs and health-related resource utilisation in the 6 months after insulin initiation in German patients with type 2 diabetes mellitus in 2006: INSTIGATE study. Curr Med Res Opin. 2008; 24:2349-58; Yeaw et al., Self-monitoring blood glucose test strip utilization in Canada. Diabetes. 2012; 61(Suppl 1):A35; Yeaw et al., Cost of self-monitoring of blood glucose in Canada among patients on an insulin regimen for diabetes. Diabetes Ther. Epub Jun. 27, 2012. doi: 10.1007/s13300-012-0007-6; and Yeaw et al., Cost of self-monitoring of blood glucose in the United States among patients on an insulin regimen for diabetes. J Manag. Care Pharm. 2012; 18:21-32). In a retrospective database analysis in the US that included more than 45,000 patients, testing accounted for 27% of diabetes care costs: total combined blood glucose testing and insulin-related costs were $2,850 USD/patient/year, with $772 USD/patient/year attributed to blood glucose testing alone (Yeaw et al., Cost of self-monitoring of blood glucose in the United States among patients on an insulin regimen for diabetes. J Manag. Care Pharm. 2012; 18:21-32). In other countries, testing includes an even higher percentage of diabetes care costs, e.g., 40% in Canada (Yeaw et al., Self-monitoring blood glucose test strip utilization in Canada. Diabetes. 2012; 61(Suppl 1):A35; Yeaw et al., Cost of self-monitoring of blood glucose in Canada among patients on an insulin regimen for diabetes. Diabetes Ther. Epub Jun. 27, 2012. doi: 10.1007/s13300-012-0007-6) and 42% in Germany (Liebl et al., Direct costs and health-related resource utilisation in the 6 months after insulin initiation in German patients with type 2 diabetes mellitus in 2006: INSTIGATE study. Curr Med Res Opin. 2008; 24:2349-58).

Hence, there is pressure to reduce the frequency of blood glucose measurements in order to improve patient quality of life, improve administration regime adherence (leading to improved patient outcomes) and reduce treatment costs. However, there are conflicting pressures to increase the frequency of blood glucose measurement and insulin administration in order to most effectively achieve glycemic control and thereby reduce diabetes-associated complications.

The information disclosed in this Background section is only for enhancement of understanding of the general background of the invention and should not be taken as an acknowledgment or any form of suggestion that this information forms the prior art already known to a person skilled in the art.

Given the above background, what is needed in the art are devices, systems and methods for providing improved insulin medicament dosing and administration, e.g., thereby treating type 2 diabetes.

SUMMARY

The present disclosure addresses the need in the art for devices, systems and methods for providing improved insulin medicament dosing and administration, particularly for use in between visits to a health care practitioner. In the present disclosure, a device is provided for the administration of a long-acting or ultra-long-acting insulin, e.g., thereby treating diabetes. A plurality of glucose measurements of a subject in need of treatment over a time course are recorded. For each respective glucose measurement in the plurality of glucose measurements, a corresponding timestamp—representing when in the time course the respective glucose measurement is made—is also recorded. A data structure is obtained from the subject. The device proceeds, responsive to receiving a dose guidance request, by using the glucose measurements and the data structure to provide an updated adjustment day dose recommendation of insulin to the subject.

The device, in some embodiments, may autonomously update the adjustment day dose recommendation of insulin in response to changes in the target glucose concentration and the actual glucose concentration of the subject.

Accordingly, one aspect of the present disclosure provides a device for administering a long-acting or ultra-long-acting insulin (e.g., LysB29(Nε-hexadecandioyl-γ-Glu) des(B30)

human insulin (insulin degludec) for use in treating type 2 diabetes mellitus in response to receiving a dose guidance request.

In one aspect of the present disclosure, the device includes collecting at least a first data structure, a second data structure, a first data set, and a second data set. In some embodiments, the first data structure includes at least a body weight of the subject, an upper limit target glucose range of the subject, a lower limit target glucose range of the subject, and an overbasalisation limit of the subject. In some embodiments, the second data structure includes at least the most recent adjustment day dose recommendation and a starting basal dose. In some embodiments, the first data set includes at least a plurality of glucose measurements of the subject taken over a time course to establish a blood glucose history and, for each respective glucose measurement in the plurality of glucose measurements, a corresponding glucose timestamp representing when in the time course the respective glucose measurement was made. In some embodiments the first data set includes data of historic hypoglycemic events (HYPO) and for each hypoglycemic event a corresponding event timestamp representing when in the time course the respective event occurred.

In some embodiments the second data set includes at least a basal insulin injection history of the subject—which includes a plurality of injections during all or a portion of the time course and, for each respective injection in the plurality of injections, a corresponding dose event amount and a dose event timestamp representing when in the time course the respective injection event occurred—and a last injection data refresh of the subject.

In another aspect of the present disclosure, the device collects at least a first data structure of the subject in order to obtain a variety of data. In some embodiments, the first data structure includes one or more of: a body weight of the subject, an upper limit target glucose range of the subject, a lower limit target glucose range of the subject, an overbasalisation limit of the subject, a most recent adjustment day dose recommendation and/or a starting insulin basal dose of the subject, a basal insulin injection history of the subject, and a last injection data refresh of the subject. In some embodiments, the injection history includes a plurality of injections during all or a portion of the time course. For each respective injection in the plurality of injections, a corresponding injection dose amount and an injection timestamp representing when in the time course the respective injection event occurred are recorded.

The device continues by proceeding with providing an adjusted day dose recommendation to the subject when at least the set of evaluation information (e.g., the first data set, the second data set, the first data structure, and the second data structure) is collected. Another aspect of the present disclosure provides that updating the adjusted day dose recommendation of the long-acting or ultra-long-acting insulin is repeated.

In some embodiments, the long-acting or ultra-long-acting insulin has the following structure (I). The long-acting or ultra-long-acting insulin includes a side chain attached to the α-amino group of the N-terminal amino acid residue of the B chain or to the ε-amino group of the Lys residue present in the B chain of the parent insulin, the side chain being of the general formula:

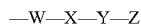

wherein W is:
(i) an α-amino acid residue having a carboxylic acid group in the side chain which residue forms, with one of its carboxylic acid groups, an amide group together with the α-amino group of the N-terminal amino acid residue of the B chain or together with the ε-amino group of a Lys residue present in the B chain of the parent insulin;
(ii) a chain composed of two, three or four α-amino acid residues linked together via amide bonds, which chain—via an amide bond—is linked to the α-amino group of the N-terminal amino acid residue of the B chain or to the ε-amino group of a Lys residue present in the B chain of the parent insulin, the amino acid residues of W being selected from the group of amino acid residues having a neutral side chain and amino acid residues having a carboxylic acid group in the side chain so that W has at least one amino acid residue which has a carboxylic acid group in the side chain; or
(iii) a covalent bond from X to the α-amino group of the N-terminal amino acid residue of the B chain or to the ε-amino group of a Lys residue present in the B chain of the parent insulin; wherein X is:

 (i)

 (ii)

 (iii)

 (iv)

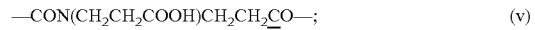 (v)

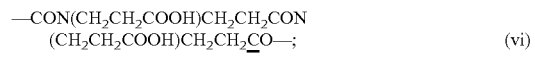 (vi)

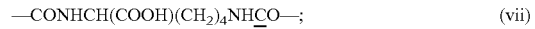 (vii)

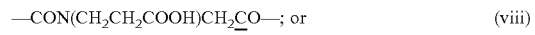 (viii)

 (ix)

provided that:
(a) when W is an amino acid residue or a chain of amino acid residues, via a bond from the underscored carbonyl carbon forms an amide bond with an amino group in W; or
(b) when W is a covalent bond, via a bond from the underscored carbonyl carbon forms an amide bond with the N-terminal α-amino group in the B chain or with the ε-amino group of a Lys residue present in the B chain of the parent insulin;

wherein Y is:
(i) a $-(CH_2)_m-$ where m is an integer in the range of 6 to 32;
(ii) a divalent hydrocarbon chain comprising 1, 2 or 3 —CH=CH— groups and a number of —CH$_2$— groups sufficient to give a total number of carbon atoms in the chain in the range of 10 to 32; or
(iii) a divalent hydrocarbon chain of the formula $-(CH_2)_v C_6H(CH_2)_w-$ wherein v and w are integers or one of them is zero so that the sum of v and w is in the range of 6 to 30;

wherein Z is:

 (i)

 (ii)

 (iii)

 (iv)

—CO-Sar; (v)

—CH(COOH)$_2$; (vi)

—N(CH$_2$COOH)$_2$; (vii)

—SO$_3$H; or (viii)

—PO$_3$H; (ix)

and any Zn$^{2+}$ complexes thereof, provided that when W is a covalent bond and X is —CO—, then Z is different from —COOH.

In some embodiments, the long-acting insulin or ultra-long-acting insulin is LysB29(Nε-hexadecandioyl-γ-Glu) des(B30) human insulin (insulin degludec). In some embodiments, the long-acting insulin or ultra-long-acting insulin is selected from the group consisting of neutral protamine hagedorn insulin, Lente Insulin, Ultralente Insulin, Glargine Insulin, Detemir Insulin, Hypurin Bovine Lente, and Hypurin Bovine PZI.

In one aspect of the present disclosure, the long-acting insulin or ultra-long-acting for use is administered, either concurrently or consecutively, together with one or more additional drugs used in the treatment of diabetes. In some embodiments, the one or more additional drug used in the treatment of diabetes is, or includes, a drug selected from the group consisting of: insulins, sensitizers (such as biguanides and thiazolidinediones), secretagogues (such as sulfonylureas and nonsulfonylurea secretagogues), alpha-glucosidase inhibitors and peptide analogs (such as injectable incretin mimetics, gastric inhibitory peptide analogs, dipeptidyl peptidase-4 inhibitors and injectable amylin analogues). In some embodiments, the long-acting or ultra-long-acting insulin is LysB29(Nε-hexadecandioyl-γ-Glu) des(B30) human insulin (insulin degludec) and is administered, concurrently or consecutively, with liraglutide.

In one aspect of the present disclosure, the device further updates the dose guidance recommendation for the subject, unless the injection history of the subject includes one or more dose events of the subject that have dose event timestamps within the current day.

In another aspect of the present disclosure, the device further calculates a reconstructed blood glucose history of the subject when the blood glucose history time course contains a gap. The reconstructed blood glucose history is calculated based on the blood glucose history of each calendar day.

In some embodiments, the device further provides a wherein the method further comprises providing a re-recommendation of the dose guidance recommendation until (i) one or more injections with an injection amount equivalent to the dose guidance baseline have occurred, (ii) one or more injections have occurred since the dose guidance baseline and when one or more injections have occurred over the current day and the past two or three or four days, and (iii) one or more does events with an injection amount greater than or equal to the dose guidance baseline have occurred.

BRIEF DESCRIPTION OF THE DRAWINGS

FIGS. 3A, 3B, 3C, 3D, 3E, 3F, 3G, and 3H collectively provide a flow chart of processes and features of a device for autonomously adjusting a long acting insulin medicament dosage in a prescribed insulin regimen in accordance with various embodiments of the present disclosure.

DETAILED DESCRIPTION

Diabetes is a growing world health epidemic. Although diabetes can be effectively managed with established titration treatment regimens and pharmaceuticals, the access to up-to-date titration recommendations remains limited. The present disclosure provides, a patient-focused titration algorithm that would encourage self-titration, enhancing patient empowerment as well as substantially reducing treatment costs by reducing the frequency of required physician consultations for dose adjustments without reducing therapeutic outcomes.

The present disclosure relies upon the acquisition of data regarding a data set(s) including information relating to a subject. The data set(s) include a body weight of the subject, an upper limit target glucose range of the subject, a lower limit target glucose range of the subject, an overbasalisation limit of the subject, a most recent adjustment day dose recommendation and/or a starting basal dose for the subject, a basal insulin injection history of the subject—where the injection history includes a plurality of injections during all or a portion of the time course and, for each respective injection in the plurality of injections, a corresponding dose event amount and a dose event timestamp representing when in the time course the respective injection event occurred—a last injection data refresh of the subject, and a plurality of glucose measurements of the subject taken over a time course to establish a blood glucose history—and for each respective glucose measurement in the plurality of glucose measurements a corresponding glucose timestamp representing when in the time course the respective glucose measurement was made.

Figure 1:
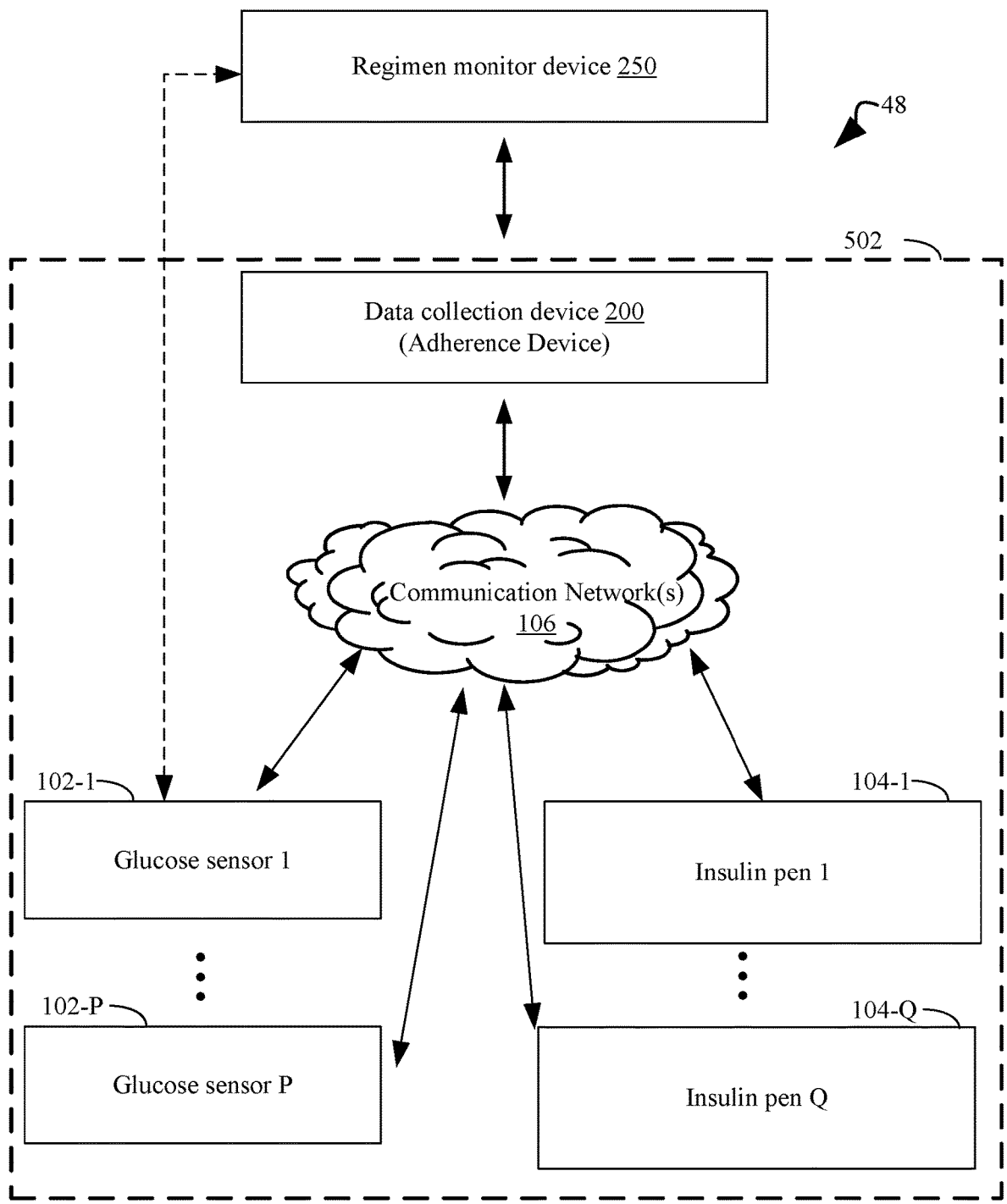
FIG. 1 illustrates an exemplary system topology that includes a regimen monitor device for autonomously adjusting a long acting insulin medicament dosage in a prescribed insulin regimen for a subject, a data collection device for collecting patient data, one or more glucose sensors that measure glucose data from the subject, and one or more insulin pens that are used by the subject to inject insulin medicaments in accordance with the prescribed insulin medicament regimen, where the above-identified components are interconnected, optionally through a communications network, in accordance with an embodiment of the present disclosure.
Figure 5:
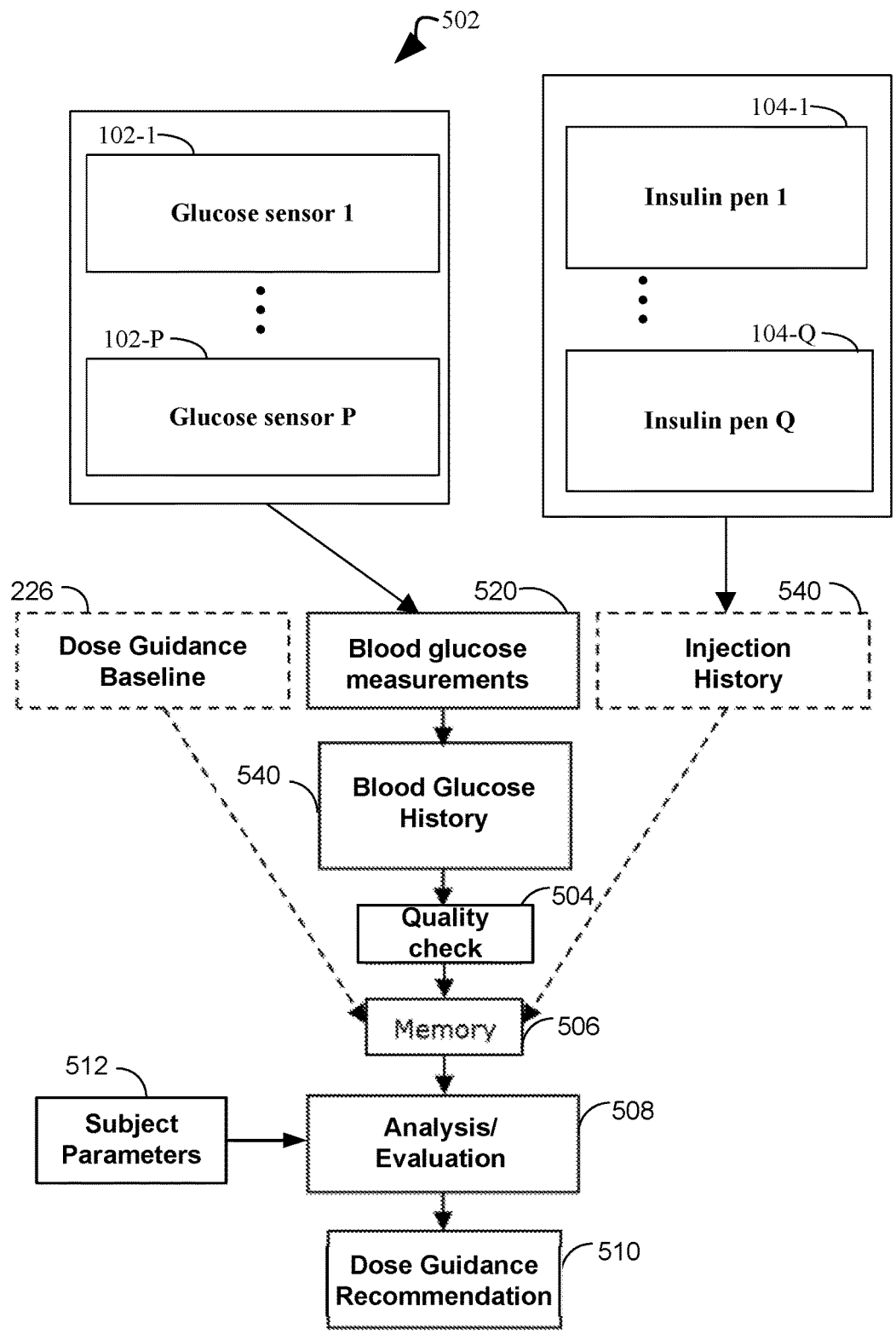
FIG. 5 illustrates an example integrated system of connected insulin pen(s), continuous glucose monitor(s), memory and a processor for autonomously adjusting a long acting insulin medicament dosage in a prescribed insulin regimen in accordance with an embodiment of the present disclosure.

FIG. 1 illustrates an example of an integrated system 502 for the acquisition of such data, and FIG. 5 provides more details of such a system 502. The integrated system 502 includes one or more connected insulin pens 104, one or more glucose monitors 102, memory 506, and a processor (not shown) for performing algorithmic categorization of autonomous glucose data of a subject. In some embodiments, a glucose monitor 102 is a continuous glucose monitor.

Reference will now be made in detail to embodiments, examples of which are illustrated in the accompanying drawings. In the following detailed description of implementations, numerous specific details are set forth in order to provide a thorough understanding of the present invention. However, it will be apparent to one of ordinary skill in the art that the present invention may be practiced without these specific details.

Definitions

It will also be understood that, although the terms first, second, etc. may be used herein to describe various elements, these elements should not be limited by these terms. These terms are only used to distinguish one element from another. For example, a first filter could be termed a second filter, and, similarly, a second filter could be termed a first filter, without departing from the scope of the present disclosure. The first filter and the second filter are both filters, but they are not the same filter. Furthermore, the terms "subject," "individual," and "user" are used interchangeably herein and refer to humans. Preferably, the individual is an adult individual.

By the term "insulin pen" is meant an injection device suitable for applying discrete doses of insulin, and wherein the injection device is adapted for logging and communicating dose related data.

The terminology used in the present disclosure is for the purpose of describing particular embodiments only and is not intended to be limiting of the invention. As used in the description of the invention and the appended embodiments, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

The term "alkyl," by itself or as part of another substituent, means, unless otherwise stated, a straight or branched chain, or cyclic hydrocarbon radical, or combination thereof, which may be fully saturated, mono- or polyunsaturated and can include di-, tri- and multivalent radicals, having the number of carbon atoms designated (e.g. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to optionally include those derivatives of alkyl defined in more detail below, such as "heteroalkyl." Alkyl groups that are limited to hydrocarbon groups are termed "homoalkyl". Exemplary alkyl groups include the monounsaturated $C_{9-10}$, oleoyl chain or the diunsaturated $C_{9-10, 12-13}$ linoeyl chain.

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The terms "cycloalkyl" and "heterocycloalkyl," by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Further exemplary cycloalkyl groups include steroids, e.g., cholesterol and its derivatives. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl substituent groups (or rings) that contain from one to four heteroatoms selected from N, O, S, Si and B, wherein the nitrogen and sulfur atoms are optionally oxidized, and the nitrogen atom(s) are optionally quaternized. An exemplary heteroaryl group is a six-membered azine, e.g., pyridinyl, diazinyl and triazinyl. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl.

Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes aryl, heteroaryl and heteroarene rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl, and "heteroaryl") are meant to optionally include both substituted and unsubstituted forms of the indicated species. Exemplary substituents for these species are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: H, substituted or unsubstituted aryl, substituted or unsubstituted heteroaryl, substituted or unsubstituted heterocycloalkyl, —OR', =O, =NR', =N—OR', —NR'R", —SR', halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", NR C(NR'R")=NR"', —S(O)R', —S(O)$_2$R', —S(O)$_2$NR'R", NRSO$_2$R', —CN and —NO$_2$ in a number ranging from zero to (2 m'+1), where m' is the total number of carbon atoms in such radical. R', R", R"' and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R"' and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O) CF$_3$, —C(O)CH$_2$OCH$_3$, and the like). These terms encompass groups considered exemplary "alkyl group substituents," which are components of exemplary "substituted alkyl" and "substituted heteroalkyl" moieties.

Similar to the substituents described for the alkyl radical, substituents for the aryl heteroaryl and heteroarene groups are generically referred to as "aryl group substituents." The substituents are selected from, for example: groups attached to the heteroaryl or heteroarene nucleus through carbon or a heteroatom (e.g., P, N, O, S, Si, or B) including, without limitation, substituted or unsubstituted alkyl, substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R"', —OC(O)R', —C(O)R', —CO$_2$R', —CONR'R", —OC(O) NR'R", —NR"C(O)R', NR' C(O)NR"R"', —NR" C(O)$_2$R', NR—C(NR'R"R"')=NR"", NR C(NR'R")=NR"', —S(O) R', —S(O)$_2$R', —S(O)$_2$NR'R", NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system. Each of the above-named groups is attached to the heteroarene or heteroaryl nucleus directly or through a heteroatom (e.g., P, N, O, S, Si, or B); and where R', R", R"' and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R"' and R"" groups when more than one of these groups is present.

As used herein, the term "heteroatom" includes oxygen (O), nitrogen (N), sulfur (S) and silicon (Si), boron (B) and phosphorous (P).

The symbol "R" is a general abbreviation that represents a substituent group that is selected from H, substituted or unsubstituted alkyl, substituted or unsubstituted heteroalkyl, substituted or unsubstituted aryl, substituted or unsubstituted heteroaryl, and substituted or unsubstituted heterocycloalkyl groups.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure or be stereoisomeric mixtures. In addition, it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

Modifications in the insulin molecule are denoted stating the chain (A or B), the position, and the one or three letter code for the amino acid residue substituting the native amino acid residue. By "desB30" or "B(1-29)" is meant a natural insulin B chain or an analogue thereof lacking the B30 amino acid and "A(1-21)" means the natural insulin A chain. Thus, e.g., A21Gly, B28Asp, desB30 human insulin is an analogue of human insulin where the amino acid in position 21 in the A chain is substituted with glycine, the amino acid in position 28 in the B chain is substituted with aspartic acid, and the amino acid in position 30 in the B chain is deleted.

Herein, the term "amino acid residue" is an amino acid from which, formally, a hydroxy group has been removed from a carboxy group and/or from which, formally, a hydrogen atom has been removed from an amino group.

Examples of insulin analogues are such wherein Pro in position 28 of the B chain is substituted with Asp, Lys, Leu, Val, or Ala and/or Lys at position B29 is substituted with Pro, Glu or Asp. Furthermore, Asn at position B3 may be substituted with Thr, Lys, Gln, Glu or Asp. The amino acid residue in position A21 may be substituted with Gly. Also one or more amino acids may be added to the C-terminal of the A-chaiand/or B-chain such as, e.g., Lys. The amino acid in position B1 may be substituted with Glu. The amino acid in position B16 may be substituted with Glu or His. Further examples of insulin analogues are the deletion analogues, e.g., analogues where the B30 amino acid in human insulin has been deleted (des(B30) human insulin), insulin analogues wherein the B1 amino acid in human insulin has been deleted (des(B1) human insulin), des(B28-B30) human insulin and des(B27) human insulin. Insulin analogues wherein the A-chain and/or the B-chain have an N-terminal extension and insulin analogues wherein the A-chain and/or the B-chain have a C-terminal extension such as with two arginine residues added to the C-terminal of the B-chain are also examples of insulin analogues. Further examples are insulin analogues comprising combinations of the mentioned mutations. Insulin analogues wherein the amino acid in position A14 is Asn, Gln, Glu, Arg, Asp, Gly or His, the amino acid in position B25 is His and which optionally further comprises one or more additional mutations are further examples of insulin analogues. Insulin analogues of human insulin wherein the amino acid residue in position A21 is Gly and wherein the insulin analogue is further extended in the C-terminal with two arginine residues are also examples of insulin analogues.

According to the present invention, the basal insulin comprises or consists of long-acting insulin and ultra-long acting insulin.

A 'long-acting insulin' includes a derivative or analogue of a naturally occurring insulin that:
(a) exhibits in physiological conditions, at least in part, the insulin receptor binding of the naturally occurring insulin, preferably, at least 0.01% of the insulin receptor binding of the naturally occurring insulin, for example, at least 0.1%, at least, 1%, at least 5%, at least 10%, at least 15%, at least 20%, at least 25% at least 50%, at least 65%, at least 75%, at least 85%, at least 95%, at least 100%, at least 110%, at least 120%, at least 130%, at least 140% or at least 150% of the insulin receptor binding of the naturally occurring insulin, and/or, at least in part, the potency of the naturally occurring insulin, preferably, at least 25% of the potency of the naturally occurring insulin, for example, at least 50%, at least 65%, at least 75%, at least 85%, at least 95%, at least 100%, at least 110%, at least 120%, at least 130%, at least 140% or at least 150% of the potency of the naturally occurring insulin; and
(b) exhibits a mean terminal half-life of at least 5 hours and less than 18 hours in physiological conditions when injected subcutaneously, for example, at least 7 hours, at least 8 hours, at least 10 hours, at least 12.5 hours, greater than 12.5 hours, at least 15 hours or at least 17.5 hours and less than 18 hours, between 5 and 17.5 hours, between 10 and 17.5 hours or between 15 and 17.5 hours.

Preferably, the 'long-acting insulin' also:
(c) induces in a subject a maximum deviation from mean insulin concentration (AUCF %) over a 24 hour period of $\leq \pm 20$, for example $\leq \pm 18$, $\leq \pm 17$, $\leq \pm 16$, $\leq \pm 15$, $\leq \pm 14$, $\leq \pm 13$, $\leq \pm 12$, $\leq \pm 11$, $\leq \pm 10$, $\leq \pm 9$, $\leq \pm 8$, $\leq \pm 7$, $\leq \pm 6$, $\leq \pm 5$, $\leq \pm 4$, $\leq \pm 3$, $\leq \pm 2$, $\leq \pm 1$, $\leq \pm 0.5$, $\leq \pm 0.1$.

An 'ultra-long-acting' insulin includes a derivative or analogue of a naturally occurring insulin that:
(a) exhibits in physiological conditions, at least in part, the insulin receptor binding of the naturally occurring insulin, preferably, at least 0.01% of the insulin receptor binding of the naturally occurring insulin, for example, at least 0.1%, at least, 1%, at least 5%, at least 10%, at least 15%, at least 20%, at least 25% at least 50%, at least 65%, at least 75%, at least 85%, at least 95%, at least 100%, at least 110%, at least 120%, at least 130%, at least 140% or at least 150% of the insulin receptor binding of the naturally occurring insulin, and/or, at least in part, the potency of the naturally occurring insulin, preferably, at least 25% of the potency of the naturally occurring insulin, for example, at least 50%, at least 65%, at least 75%, at least 85%, at least 95%, at least 100%, at least 110%, at least 120%, at least 130%, at least 140% or at least 150% of the potency of the naturally occurring insulin;
(b) exhibits a mean terminal half-life of at least 18 hours in physiological conditions when injected subcutaneously, for example, greater than 18 hours, at least 20 hours, greater than 20 hours, greater than 22 hours, at least 22.5 hours, or greater than 24 hours, at least 25 hours, at least 27.5 hours, at least 30 hours, at least 32.5, at least 35 hours, at least 37.5 hours, or at least 40 hours, or between 18 and 40 hours, between 20 and 40 hours, between 24 and 40 hours.

Preferably, the 'ultra-long acting insulin' also:
(c) induces in a subject a maximum deviation from mean insulin concentration (AUCF %) over a 24 hour period of $\leq \pm 20$, for example, $\leq \pm 18$, $\leq \pm 17$, $\leq \pm 16$, $\leq \pm 15$, $\leq \pm 14$, $\leq \pm 13$, $\leq \pm 12$, $\leq \pm 11$, $\leq \pm 10$, $\leq \pm 9$, $\leq \pm 8$, $\leq \pm 7$, $\leq \pm 6$, $\leq \pm 5$, $\leq \pm 4$, $\leq \pm 3$, $\leq \pm 2$, $\leq \pm 1$, $\leq \pm 0.5$, $\leq \pm 0.1$.

In principle, the longer the half-life of the insulin, the more stable and evenly distributed the glucose-lowering effect over a dosing interval (i.e. time interval between injections).

According to the present invention, the basal insulin comprises or consists of long-acting insulin and ultra-long acting insulin.

According to the present invention, the basal insulin is administered in an amount to achieve a beneficial glycemic control in said subject.

According to the present invention, the beneficial glycemic control in said subject is determined by at least the levels of $HbA_{1c}$ (glycosylated hemoglobin) in said subject after administration of said basal insulin.

By use of the basal insulin and its administration according to the present invention it is possible to achieve improvements in the proportion of patients in need thereof reaching $HbA_{1c}$ targets.

As used herein the term "U" refers to a unit of insulin (or an analogue or derivative thereof). The designation "U" with a number following indicates the concentration as measured by the number of units per ml of fluid volume (Joslin's Diabetes Deskbook, 2nd edition, Chapter 9 Using insulin to treat diabetes—general principles, page 268). Further information about the meaning of "U" can be found in a document from the EMA (reference EMEA/CHMP/BWP/124446/2005) entitled "Guideline on potency labelling for insulin analogue containing products with particular reference to the use of "International Units" or "Units"" (see http://www.ema.europa.eu/docs/en_GB/document_library/Scientific_guideline/2009/09/WC500 003654.pdf). "IU" refers to an international unit of human insulin as defined according to the WHO Expert Committee on Biological Standardization. IU is a standardized parameter. For commercial insulins, the labels indicate the content of 1 U (unit) of the particular insulin analogue.

As used herein the term "administration period" means the period for which the long-acting or ultra-long-acting insulin is administered in a given dose.

The term "diabetes" or "diabetes mellitus" includes type 1 diabetes mellitus, type 2 diabetes mellitus, gestational diabetes (during pregnancy) and other states that cause hyperglycemia. The term is used for a metabolic disorder in which the pancreas produces insufficient amounts of insulin, or in which the cells of the body fail to respond appropriately to insulin thus preventing cells from absorbing glucose. As a result, glucose builds up in the blood.

DESCRIPTION

Figure 2:
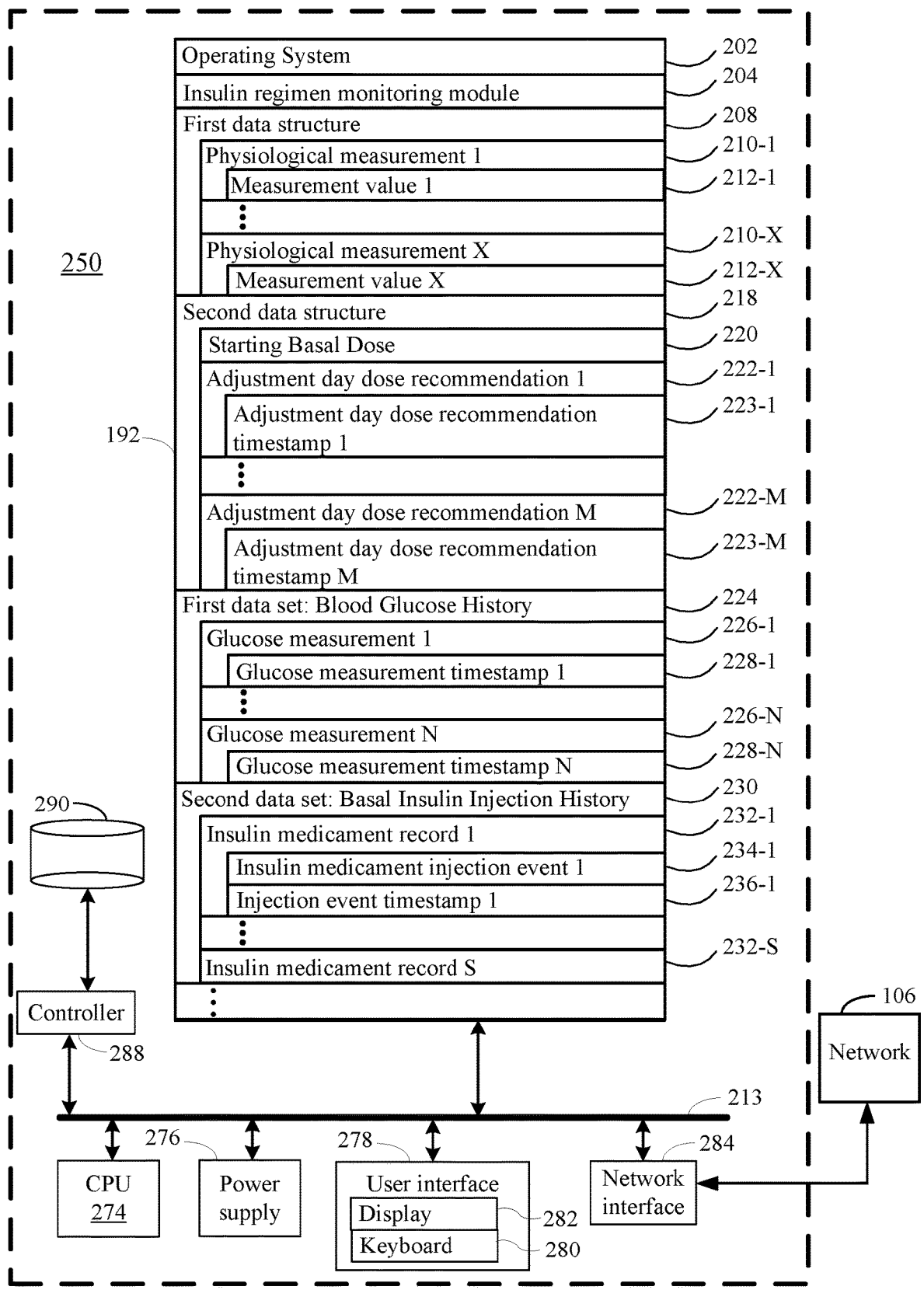
FIG. 2 illustrates a device for autonomously adjusting a long acting insulin medicament dosage in a prescribed insulin regimen in accordance with an embodiment of the present disclosure.

A detailed description of a system 48 for autonomously adjusting a long acting insulin medicament dosage in a prescribed insulin regimen for a subject in accordance with the present disclosure is described in conjunction with FIGS. 1 and 2. As such, FIGS. 1 and 2 collectively illustrate the topology of the system in accordance with the present disclosure. In the topology, there is a regimen monitoring device for autonomously adjusting a long acting insulin medicament dosage in a prescribed insulin regimen for a subject ("regimen monitor device 250") (FIGS. 1 and 2), a device for data collection ("data collection device 200"), one or more glucose sensors 102 associated with the subject (FIGS. 1 and 5), and one or more insulin pens 104 for injecting insulin medicaments into the subject (FIGS. 1 and 5). Throughout the present disclosure, the data collection device 200 and the regimen monitor device 250 will be referenced as separate devices solely for purposes of clarity. That is, the disclosed functionality of the data collection device 200 and the disclosed functionality of the regimen monitor device 250 are contained in separate devices as illustrated in FIG. 1. However, it will be appreciated that, in fact, in some embodiments, the disclosed functionality of the data collection device 200 and the disclosed functionality of the regimen monitor device 250 are contained in a single device. In some embodiments, the disclosed functionality of the data collection device 200 and/or the disclosed functionality of the regimen monitor device 250 are contained in a single device and this single device is a glucose monitor 102 or the insulin pen 104.

Referring to FIG. 1, the regimen monitor device 250 autonomously adjusts a long acting insulin medicament dosage in a prescribed insulin regimen for a subject. To do this, the data collection device 200, which is in electrical communication with the regimen monitor device 250, receives autonomous glucose measurements originating from one or more glucose sensors 102 attached to a subject on an ongoing basis. In some embodiments, the data collection device 200 also receives insulin medicament injection data from one or more insulin pens 104 used by the subject to inject insulin medicaments. In some embodiments, the data collection device 200 receives such data directly from the glucose sensor(s) 102 and insulin pens 104 used by the subject. For instance, in some embodiments the data collection device 200 receives this data wirelessly through radio-frequency signals. In some embodiments such signals are in accordance with an 802.11 (WiFi), Bluetooth, or ZigBee standard. In some embodiments, the data collection device 200 receives such data directly, analyzes the data, and passes the analyzed data to the regimen monitor device 250. In some embodiments, a glucose sensor 102 and/or insulin pen 104 includes an RFID tag and communicates to the data collection device 200 and/or the regimen monitor device 250 using RFID communication. In some embodiments, the data collection device 200 also obtains or receives physiological measurements 210 of the subject (e.g., from wearable physiological measurement devices, from measurement devices within the data collection device 200 such as a magnetometer or thermostat, etc.). For some embodiments of the present invention, said insulin pen device is FlexPen® or FlexTouch®. FlexPen® and or Flex-Touch® are trademarks of Novo Nordisk A/S.

In some embodiments, the data collection device 200 and/or the regimen monitor device 250 is not proximate to the subject and/or does not have wireless capabilities or such wireless capabilities are not used for the purpose of acquiring glucose data, insulin medicament injection data, and/or physiological measurement data. In such embodiments, a communication network 106 may be used to communicate glucose measurements from the glucose sensor 102 to the data collection device 200 and/or the regimen monitor device 250, insulin medicament injection data from the one or more insulin pens 104 to the data collection device 200 and/or the regimen monitor device 250, and/or physiological measurement data from one or more physiological measurement devices (not shown) to the data collection device 200 and/or the regimen monitor device 250.

Examples of networks 106 include, but are not limited to, the World Wide Web (WWW), an intranet and/or a wireless network, such as a cellular telephone network, a wireless local area network (LAN) and/or a metropolitan area network (MAN), and other devices by wireless communication. The wireless communication optionally uses any of a plurality of communications standards, protocols and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11ac, IEEE 802.11ax, IEEE 802.11b, IEEE 802.11g and/or IEEE 802.11n), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of the present disclosure.

In some embodiments, there is a single glucose sensor 102 attached to the subject and the data collection device 200 and/or the regimen monitor device 250 is part of the glucose sensor 102. That is, in some embodiments, the data collection device 200 and/or the regimen monitor device 250 and the glucose sensor 102 are a single device.

In some embodiments, the data collection device 200 and/or the regimen monitor device 250 is part of an insulin pen. That is, in some embodiments, the data collection device 200 and/or the regimen monitor device 250 and an insulin pen 104 are a single device.

Of course, other topologies of the system 48 are possible. For instance, rather than relying on a communications network 106, the one or more glucose sensors 102 and the one or more insulin pens 104 may wirelessly transmit information directly to the data collection device 200 and/or regimen monitor device 250. Further, the data collection device 200 and/or the regimen monitor device 250 may constitute a portable electronic device, a server computer, or in fact constitute several computers that are linked together in a network or be a virtual machine in a cloud computing context. As such, the exemplary topology shown in FIG. 1 merely serves to describe the features of an embodiment of the present disclosure in a manner that will be readily understood to one of skill in the art.

While the system 48 disclosed in FIG. 1 can work standalone, in some embodiments it can also be linked with electronic medical records to exchange information in any way.

Referring to FIG. 2, in typical embodiments, the regimen monitor device 250 comprises one or more computers. For purposes of illustration in FIG. 2, the regimen monitor device 250 is represented as a single computer that includes all of the functionality for evaluating historical adherence to a prescribed insulin medicament dosage regimen for a subject. However, the disclosure is not so limited. In some embodiments, the functionality for autonomously adjusting a long acting insulin medicament dosage in a prescribed insulin regimen for a subject is spread across any number of networked computers and/or resides on each of several networked computers and/or is hosted on one or more virtual machines at a remote location accessible across the communications network 106. One of skill in the art will appreciate that any of a wide array of different computer topologies are used for the application and all such topologies are within the scope of the present disclosure.

In some embodiments, an exemplary regimen monitor device 250 for autonomously adjusting a long acting insulin medicament dosage in a prescribed insulin regimen for a subject comprises one or more processing units (CPU's) 274, a network or other communications interface 284, a memory 192 (e.g., random access memory), one or more magnetic disk storage and/or persistent devices 290 optionally accessed by one or more controllers 288, one or more communication busses 213 for interconnecting the aforementioned components, and a power supply 276 for powering the aforementioned components. In some embodiments, data in memory 192 is seamlessly shared with non-volatile memory 290 using known computing techniques such as caching. In some embodiments, memory 192 and/or memory 290 includes mass storage that is remotely located with respect to the central processing unit(s) 274. In other words, some data stored in memory 192 and/or memory 290 may in fact be hosted on computers that are external to the regimen monitor device 250 but that can be electronically accessed by the regimen monitor device 250 over an Internet, intranet, or other form of network or electronic cable (illustrated as element 106 in FIG. 2) using network interface 284.

In some embodiments, the memory 192 of the regimen monitor device 250 for autonomously adjusting a long acting insulin medicament dosage in a prescribed insulin regimen for a subject stores:

an operating system 202 that includes procedures for handling various basic system services;
an insulin regimen monitoring module 204;
a first data structure 208, the first data structure comprising physiological measurements of the subject 210 (e.g., 210-1, 210-2, and 210-X);
a second data structure 218, the second data structure representing a Starting Basal Dose 220 of the subject, a plurality of adjustment day dose recommendations 222 for the subject and for each respective adjustment day dose recommendation 222 in the plurality of adjustment day dose recommendations (e.g., 222-1, 222-2, and 222-M) a timestamp 223 representing when the respective adjustment day dose recommendation was made;
a first data set 224 (e.g., a blood glucose history), the first data set comprising a plurality of glucose measurements of the subject over the time course, and for each respective glucose measurement 226 in the plurality of glucose measurements (e.g., 226-1, 226-2, and 226-N), a timestamp 228 representing when the respective glucose measurement was made;
a second data set 230 (e.g., a basal insulin injection history), the second data set comprising a plurality of insulin medicament records, where each respective insulin medicament record 232 in the plurality of insulin medicament records (e.g., 232-1, 232-2, 232-S) comprises a respective insulin medicament injection event 234 associated with the one or more insulin pens 104 in which an insulin medicament was injected into the subject and an injection event time stamp 236 that indicates when the respective medicament injection event 232 occurred.

In some embodiments, the insulin regimen monitoring module 204 is accessible within any browser (smart phone, tablet computer, laptop/desktop computer). In some embodiments the insulin regimen monitoring module 204 runs on native device frameworks, and is available for download onto the regimen monitor device 250 running an operating system 202 such as Android or iOS.

In some implementations, one or more of the above identified data elements or modules of the regimen monitor device 250 for autonomously adjusting a long acting insulin medicament dosage in a prescribed insulin regimen for a subject are stored in one or more of the previously described memory devices, and correspond to a set of instructions for performing a function described above. The above-identified data, modules or programs (e.g., sets of instructions) need not be implemented as separate software programs, procedures or modules, and thus various subsets of these modules may be combined or otherwise re-arranged in various implementations. In some implementations, the memory 192 and/or 290 optionally stores a subset of the modules and data structures identified above. Furthermore, in some embodiments the memory 192 and/or 290 stores additional modules and data structures not described above.

In some embodiments, a regimen monitor device 250 for autonomously adjusting a long acting insulin medicament dosage 216 in a prescribed insulin regimen 212 for a subject is a smart phone (e.g., an iPhone®), laptop computer, tablet computer, desktop computer, or other form of electronic device (e.g., a gaming console). In some embodiments, the regimen monitor device 250 is not mobile. In some embodiments, the regimen monitor device 250 is mobile.

In some embodiments the regimen monitor device 250 is a smart phone. In other embodiments, the regimen monitor device 250 is not a smart phone but rather is a tablet computer, desktop computer, emergency vehicle computer, or other form or wired or wireless networked device. In some embodiments, the regimen monitor device 250 has any or all of the circuitry, hardware components, and software components found in the regimen monitor device 250 depicted in FIG. 2. In the interest of brevity and clarity, only a few of the possible components of the regimen monitor device 250 are shown in order to better emphasize the additional software modules that are installed on the regimen monitor device 250.

The regimen monitor device 250 accesses and/or stores a first data structure 210 that includes a prescribed insulin regimen 212 for the subject that is used to match as closely as possible normal physiologic insulin secretion to control fasting and postprandial plasma glucose. In the present disclosure, the prescribed insulin regimen 212 comprises a basal insulin medicament dosage regimen 214 that specifies the long acting insulin medicament dosage 216. The first data structure 210 further specifies an original target fasting blood glucose level 226 used as a basis to compute the long acting insulin medicament dosage.

In some embodiments, the glucose measurements 226 are autonomously measured. The FREESTYLE LIBRE CGM by ABBOTT ("LIBRE") is an example of a glucose sensor that may be used as a glucose sensor 102 in order to make autonomous glucose measurements of a subject. The LIBRE allows calibration-free glucose measurements with an on-skin coin-sized sensor, which can send up to eight hours of data to a reader device (e.g., the data collection device 200 and/or the regimen monitor device 250) via near field communications, when brought close together. The LIBRE can be worn for fourteen days in all daily life activities.

In some embodiments, the long acting insulin medicament specified by the basal insulin medicament dosage regimen 214 consists of a single insulin medicament having a duration of action that is between 12 and 24 hours or a mixture of insulin medicaments that collectively have a duration of action that is between 12 and 24 hours. Examples of such long acting insulin medicaments include, but are not limited to insulin degludec (developed by NOVO NORDISK under the brand name Tresiba®), NPH (Schmid, 2007, "New options in insulin therapy. J Pediatria (Rio J). 83(Suppl 5):S146-S155), Glargine (LANTUS, Mar. 2, 2007, insulin glargine [rDNA origin] injection, [prescribing information], Bridgewater, New Jersey: Sanofi-Aventis), and detemir (Plank et al., 2005, "A double-blind, randomized, dose-response study investigating the pharmacodynamic and pharmacokinetic properties of the long-acting insulin analog detemir," Diabetes Care 28:1107-1112).

In some embodiments, the plurality of glucose levels in the first data set 228 (e.g., the value P) is limited to glucose levels measured from the subject in the past four hours, the past twelve hours, the past 24 hours, the past two days, the past week, or the past two weeks. In other words, in some embodiments, the first data set 228 only has glucose measurements for the subject from the past four hours, the past twelve hours, the past 24 hours, the past two days, the past week, or the past two weeks.

Now that details of a system 48 and device 250 for autonomously adjusting a long acting insulin medicament dosage in a prescribed insulin regimen for a subject have been disclosed, details regarding a flow chart of processes and features of the system, in accordance with an embodiment of the present disclosure, are disclosed with reference to FIGS. 3A through 3H. In some embodiments, such processes and features of the system are carried out by the insulin regimen monitoring module 204 illustrated in FIG. 2.

With reference to block 302 in FIG. 3A, a goal of the present disclosure is to provide a long-acting or ultra-long-acting insulin dose guidance recommendation for a subject to treat diabetes mellitus, using a device such as the data collection device 200 and a regimen monitoring device 250. As illustrated in FIG. 2, the device includes one or more processors 274 and a memory 192/290. The memory includes instructions that, when executed by the one or more processors, perform a method responsive to receiving a dose guidance request. For some embodiments of the present invention, the present invention is used to treat a subject that is at least 20 years. For some embodiments, the present invention is used to treat a subject whose body mass index is no greater than 35 kg/m². For some embodiments, the present invention is used to treat a subject whose body mass index is about 25 kg/m². For some embodiments, the present invention is used to treat a subject that has been suffering from diabetes for at least 1 year, such as at least 5 years, such as at least 10 years. For some embodiments, the present invention is capable of achieving a baseline $HbA_{1c}$ level for the subject being no more than 7 after 26 weeks of treatment. For some embodiments, the long-acting or ultra-long-acting insulin for use according to the present invention is delivered by injection, such as by use of an insulin pen device.

Referring to block 304, in some embodiments the long-acting or ultra-long-acting insulin has a structure of structure (I). The long-acting or ultra-long-acting insulin includes a side chain attached to the α-amino group of the N-terminal amino acid residue of the B chain or to the ε-amino group of the Lys residue present in the B chain of the parent insulin, the side chain being of the general formula:

—W—X—Y—Z wherein W is:
(i) an α-amino acid residue having a carboxylic acid group in the side chain which residue forms, with one of its carboxylic acid groups, an amide group together with the α-amino group of the N-terminal amino acid residue of the B chain or together with the ε-amino group of a Lys residue present in the B chain of the parent insulin;
(ii) a chain composed of two, three or four α-amino acid residues linked together via amide bonds, which chain—via an amide bond—is linked to the α-amino group of the N-terminal amino acid residue of the B chain or to the ε-amino group of a Lys residue present in the B chain of the parent insulin, the amino acid residues of W being selected from the group of amino acid residues having a neutral side chain and amino acid residues having a carboxylic acid group in the side chain so that W has at least one amino acid residue which has a carboxylic acid group in the side chain; or
(iii) a covalent bond from X to the α-amino group of the N-terminal amino acid residue of the B chain or to the ε-amino group of a Lys residue present in the B chain of the parent insulin; wherein X is:

—C̲O—;  (i)

—COCH(COOH)C̲O—;  (ii)

—CON(CH₂COOH)CH₂C̲O—;  (iii)

—CON(CH₂COOH)CH₂CON(CH₂COOH)CH₂C̲O—;  (iv)

—CON(CH₂CH₂COOH)CH₂CH₂C̲O—;  (v)

—CON(CH₂CH₂COOH)CH₂CH₂CON(CH₂CH₂COOH)CH₂CH₂C̲O—;  (vi)

—CONHCH(COOH)(CH₂)₄NHC̲O—;  (vii)

—CON(CH₂CH₂COOH)CH₂C̲O—; or  (viii)

—CON(CH₂COOH)CH₂CH₂C̲O—  (ix)

provided that:
(a) when W is an amino acid residue or a chain of amino acid residues, via a bond from the underscored carbonyl carbon forms an amide bond with an amino group in W; or
(b) when W is a covalent bond, via a bond from the underscored carbonyl carbon forms an amide bond with the N-terminal α-amino group in the B chain or with the ε-amino group of a Lys residue present in the B chain of the parent insulin;

wherein Y is:
(i) a —$(CH_2)_m$— where m is an integer in the range of 6 to 32;
(ii) a divalent hydrocarbon chain comprising 1, 2 or 3 —CH=CH— groups and a number of —$CH_2$— groups sufficient to give a total number of carbon atoms in the chain in the range of 10 to 32; or
(iii) a divalent hydrocarbon chain of the formula —$(CH_2)_vC_6H(CH_2)_w$— wherein v and w are integers or one of them is zero so that the sum of v and w is in the range of 6 to 30;

wherein Z is:

—COOH;   (i)

—CO-Asp;   (ii)

—CO-Glu;   (iii)

—CO-Gly;   (iv)

—CO-Sar;   (v)

—$CH(COOH)_2$;   (vi)

—$N(CH_2COOH)_2$;   (vii)

—$SO_3H$; or   (viii)

—$PO_3H$;   (ix)

and any $Zn^{2+}$ complexes thereof, provided that when W is a covalent bond and X is —CO—, then Z is different from —COOH.

In an alternative or additional embodiment, the side chain —W—X—Y—Z is attached to the α-amino group of the N-terminal amino acid residue of the B chain of the parent insulin.

In an alternative or additional embodiment, the side chain —W—X—Y—Z is attached to the ε-amino group of a Lys residue present in the B chain of the parent insulin.

In an alternative or additional embodiment, the side chain —W—X—Y—Z is attached to the ε-amino group of a Lys residue present in position 28 of the B chain.

In an alternative or additional embodiment, the side chain —W—X—Y—Z is attached to the ε-amino group of a Lys residue present in position 29 of the B chain.

In an alternative or additional embodiment, the side chain —W—X—Y—Z is attached to the ε-amino group of a Lys residue present in position 30 of the B chain.

The substructure W of the side chain —W—X—Y—Z can be a covalent bond. Alternatively, W can be a residue of an α-amino acid having a carboxylic acid group in the side chain and comprising a total of from 4 to 10 carbon atoms. Specifically, W can be the residue of an α-amino acid, that can be coded for by the genetic code. Thus, W can, for example, be selected from the group consisting of α-Asp, β-Asp, α-Glu, and γ-Glu. Further options for W are for example α-hGlu and δ-hGlu.

In an alternative or additional embodiment, W is a chain composed of two α-amino acid residues of which one has from 4 to 10 carbon atoms and a carboxylic acid group in the side chain while the other has from 2 to 11 carbon atoms but no free carboxylic acid group. The α-amino acid residue with no free carboxylic acid group can be a neutral, codable α-amino acid residue. Examples of W according to this embodiment are: α-Asp-Gly; Gly-α-Asp; β-Asp-Gly; Gly-β-Asp; α-Glu-Gly; Gly-α-Glu; γ-Glu-Gly; Gly-γ-Glu; α-hGlu-Gly; Gly-α-hGlu; δ-hGlu-Gly; and Gly-δ-hGlu.

In an alternative or additional embodiment, W is a chain composed of two α-amino acid residues, independently having from 4 to 10 carbon atoms, and both having a carboxylic acid group in the side chain. One of these α-amino acid residues or both of them can be codable α-amino acid residues. Examples of W according to this embodiment are: α-Asp-α-Asp; α-Asp-α-Glu; α-Asp-α-hGlu; α-Asp-β-Asp; α-Asp-γ-Glu; α-Asp-δ-hGlu; β-Asp-α-Asp; β-Asp-α-Glu; β-Asp-α-hGlu; β-Asp-β-Asp; β-Asp-γ-Glu; β-Asp-δ-hGlu; α-Glu-α-Asp; α-Glu-α-Glu; α-Glu-α-hGlu; α-Glu-β-Asp; α-Glu-γ-Glu; α-Glu-δ-hGlu; γ-Glu-α-Asp; γ-Glu-α-Glu; γ-Glu-α-hGlu; γ-Glu-β-Asp; γ-Glu-γ-Glu; γ-Glu-δ-hGlu; α-hGlu-α-Asp; α-hGlu-α-Glu; α-hGlu-α-hGlu; α-hGlu-β-Asp; α-hGlu-γ-Glu; α-hGlu-δ-hGlu; δ-hGlu-α-Asp; δ-hGlu-α-Glu; δ-hGlu-α-hGlu; δ-hGlu-β-Asp; δ-hGlu-γ-Glu; and δ-hGlu-δ-hGlu.

In an alternative or additional embodiment, W is a chain composed of three α-amino acid residues, independently having from 4 to 10 carbon atoms, the amino acid residues of the chain being selected from the group of residues having a neutral side chain and residues having a carboxylic acid group in the side chain so that the chain has at least one residue which has a carboxylic acid group in the side chain. In one embodiment, the amino acid residues are codable residues.

In an alternative or additional embodiment, W is a chain composed of four α-amino acid residues, independently having from 4 to 10 carbon atoms, the amino acid residues of the chain being selected from the group having a neutral side chain and residues having a carboxylic acid group in the side chain so that the chain has at least one residue which has a carboxylic acid group in the side chain. In one embodiment, the amino acid residues are codable residues.

In an alternative or additional embodiment, W can be connected to the ε-amino group of the Lys residue in the B-chain via an urea derivative.

The substructure X of the side chain —W—X—Y—Z can be a group of the formula —$\underline{C}O$— that, via a bond from the underscored carbonyl carbon, forms an amide bond with an amino group in W or, when W is a covalent bond, with the N-terminal α-amino group in the B chain or with the ε-amino group of a Lys residue present in the B chain of the parent insulin.

In an alternative or additional embodiment, the substructure X of the side chain can be a group of the formula —$COCH(COOH)\underline{C}O$— that, via a bond from the underscored carbonyl carbon, forms an amide bond with an amino group in W or, when W is a covalent bond, with the N-terminal α-amino group in the B chain or with the ε-amino group of a Lys residue present in the B chain of the parent insulin.

In an alternative or additional embodiment, the substructure X of the side chain can be a group of the formula —$CON(CH_2COOH)CH_2\underline{C}O$— that, via a bond from the underscored carbonyl carbon, forms an amide bond with an amino group in W or, when W is a covalent bond, with the N-terminal α-amino group in the B chain or with the ε-amino group of a Lys residue present in the B chain of the parent insulin.

In an alternative or additional embodiment, the substructure X of the side chain can be a group of the formula —$CON(CH_2CH_2COOH)CH_2\underline{C}O$— that, via a bond from the underscored carbonyl carbon, forms an amide bond with an amino group in W or, when W is a covalent bond, with the N-terminal α-amino group in the B chain or with the ε-amino group of a Lys residue present in the B chain of the parent insulin.

In an alternative or additional embodiment of the invention the long-acting insulin, the substructure X of the side chain can be a group of the formula —CON(CH$_2$COOH)CH$_2$CH$_2$$\underline{C}$O— that, via a bond from the underscored carbonyl carbon, forms an amide bond with an amino group in W or, when W is a covalent bond, with the N-terminal α-amino group in the B chain or with the ε-amino group of a Lys residue present in the B chain of the parent insulin.

In an alternative or additional embodiment, the substructure X of the side chain can be a group of the formula —CON(CH$_2$COOH)CH$_2$CON(CH$_2$COOH)CH$_2$$\underline{C}$O— that, via a bond from the underscored carbonyl carbon, forms an amide bond with an amino group in W or, when W is a covalent bond, with the N-terminal α-amino group in the B chain or with the ε-amino group of a Lys residue present in the B chain of the parent insulin.

In an alternative or additional embodiment, the substructure X of the side chain can be a group of the formula —CON(CH$_2$CH$_2$COOH)CH$_2$CH$_2$$\underline{C}$O— that, via a bond from the underscored carbonyl carbon, forms an amide bond with an amino group in W or, when W is a covalent bond, with the N-terminal α-amino group in the B chain or with the ε-amino group of a Lys residue present in the B chain of the parent insulin.

In an alternative or additional embodiment, the substructure X of the side chain can be a group of the formula —CON(CH$_2$CH$_2$COOH)CH$_2$CH$_2$CON(CH$_2$CH$_2$COOH)CH$_2$CH$_2$$\underline{C}$O— that, via a bond from the underscored carbonyl carbon, forms an amide bond with an amino group in W or, when W is a covalent bond, with the N-terminal α-amino group in the B chain or with the ε-amino group of a Lys residue present in the B chain of the parent insulin. The substructure Y of the side chain —W—X—Y—Z can be a group of the formula —(CH$_2$)$_m$— where m is an integer in the range of from 6 to 32, from 8 to 20, from 12 to 20, or from 12-16.

In an alternative or additional embodiment, Y is a divalent hydrocarbon chain comprising 1, 2 or 3 —CH=CH— groups and a number of —CH$_2$— groups sufficient to give a total number of carbon atoms in the chain in the range of from 6 to 32, from 10 to 32, from 12 to 20, or from 12-16.

In an alternative or additional embodiment, Y is a divalent hydrocarbon chain of the formula —(CH$_2$)$_v$C$_6$H$_4$(CH$_2$)$_w$— wherein v and w are integers or one of them is zero so that the sum of v and w is in the range of from 6 to 30, from 10 to 20, or from 12-16.

In an alternative or additional embodiment, the substructure Z of the side chain —W—X—Y—Z is —COOH provided that when W is a covalent bond and X is —CO—, then Z is different from —COOH. In one embodiment Z is —COOH. In another embodiment, Z is —CO-Asp. In another embodiment, Z is —CO-Glu. In another embodiment, Z is —CO-Gly. In another embodiment, Z is —CO-Sar. In another embodiment, Z is —CH(COOH)$_2$. In another embodiment, Z is —N(CH$_2$COOH)$_2$. In another embodiment, Z is —SO$_3$H. In another embodiment, Z is —PO$_3$H.

In an alternative or additional embodiment, W is selected from the group consisting of α-Asp, β-Asp, α-Glu, and γ-Glu; X is —CO— or —COCH(COOH)CO; Y is —(CH$_2$)$_m$—where m is an integer in the range of 12-18 and Z is —COOH or —CH(COOH)$_2$.

In an alternative, the long-acting or ultra-long-acting insulin, preferably the ultra-long acting insulin, wherein said derivative has a side chain attached to the α-amino group of the N-terminal amino acid residue of the B chain or to the ε-amino group of a Lys residue present in the B chain of the parent insulin, the side chain being of the general formula:

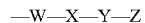

wherein W is:
an α-amino acid residue having a carboxylic acid group in the side chain which residue forms, with one of its carboxylic acid groups, an amide group together with the α-amino group of the N-terminal amino acid residue of the B chain or together with the ε-amino group of a Lys residue present in the B chain of the parent insulin wherein the α-amino acid residue is selected from the group consisting of α-Asp, β-Asp, α-Glu, γ-Glu, α-hGlu and δ-hGlu;
X is: —CO—;
Y is: —(CH$_2$)$_m$— where m is an integer in the range of 6 to 32;
Z is: —COOH;
and any Zn$^{2+}$ complexes thereof.

The insulin moiety—in the present text also referred to as the parent insulin—of an insulin derivative can be a naturally occurring insulin such as human insulin or porcine insulin. Alternatively, the parent insulin can be an insulin analogue. In one group of parent insulin analogues, the amino acid residue at position A21 is Asn. In another group of parent insulin analogues, the amino acid residue at position A21 is Gly. Specific examples from this group of analogues are Gly$^{A21}$ human insulin, Gly$^{A21}$ des(B30) human insulin; and Gly$^{A21}$Arg$^{B31}$Arg$^{B32}$ human insulin.

In another group of parent insulin analogues, the amino acid residue at position B1 has been deleted. A specific example from this group of parent insulin analogues is des(B1) human insulin.

In another group of parent insulin analogues, the amino acid residue at position B30 has been deleted. A specific example from this group of parent insulin analogues is des(B30) human insulin.

In another group of parent insulin analogues, the amino acid residue at position B28 is Asp. A specific example from this group of parent insulin analogues is Asp$^{B28}$ human insulin.

In another group of parent insulin analogues, the amino acid residue at position B28 is Lys and the amino acid residue at position B29 is Pro. A specific example from this group of parent insulin analogues is Lys$^{B28}$Pro$^{B29}$ human insulin.

In another group of parent insulin analogues the amino acid residue in position B30 is Lys and the amino acid residue in position B29 is any codable amino acid except Cys, Met, Arg and Lys. An example is an insulin analogue where the amino acid residue at position B29 is Thr and the amino acid residue at position B30 is Lys. A specific example from this group of parent insulin analogues is Thr$^{B29}$Lys$^{B30}$ human insulin.

In another group of parent insulin analogues, the amino acid residue at position B3 is Lys and the amino acid residue at position B29 is Glu. A specific example from this group of parent insulin analogues is Lys$^{B3}$Glu$^{B29}$ human insulin.

In one embodiment the parent insulin is selected from the group consisting of human insulin; des(B1) human insulin; des(B30) human insulin; GlyA21 human insulin; GlyA21 des(B30)human insulin; AspB28 human insulin; porcine insulin; LysB28ProB29 human insulin; GlyA21ArgB31ArgB32 human insulin; and LysB3GluB29 human insulin.

Examples of '347 derivatives useful in the invention are the following compounds:

$N^{\varepsilon B29}$—($N^{\alpha}$—(HOOC(CH$_2$)$_{14}$CO)-γ-Glu) des(B30) human insulin;
$N^{\varepsilon B29}$—($N^{\alpha}$—(HOOC(CH$_2$)$_{15}$CO)-γ-Glu) des(B30) human insulin;
$N^{\varepsilon B29}$—($N^{\alpha}$—(HOOC(CH$_2$)$_{16}$CO)-γ-Glu) des(B30) human insulin;
$N^{\varepsilon B29}$—($N^{\alpha}$—(HOOC(CH$_2$)$_{17}$CO)-γ-Glu) des(B30) human insulin;
$N^{\varepsilon B29}$—($N^{\alpha}$—(HOOC(CH$_2$)$_{18}$CO)-γ-Glu) des(B30) human insulin;
$N^{\varepsilon B29}$—($N^{\alpha}$—(HOOC(CH$_2$)$_{16}$CO)-γ-Glu-N-(γ-Glu)) des(B30) human insulin;
$N^{\varepsilon B29}$—($N^{\alpha}$-(Asp-OC(CH$_2$)$_{16}$CO)-γ-Glu) des(B30) human insulin;
$N^{\varepsilon B29}$—($N^{\alpha}$-(Glu-OC(CH$_2$)$_{14}$CO)-γ-Glu) des(B30) human insulin;
$N^{\varepsilon B29}$—($N^{\alpha}$-(Glu-OC(CH$_2$)$_{14}$CO—) des(B30) human insulin;
$N^{\varepsilon B29}$—($N^{\alpha}$-(Asp-OC(CH$_2$)$_{16}$CO—) des(B30) human insulin;
$N^{\varepsilon B29}$—($N^{\alpha}$—(HOOC(CH$_2$)$_{16}$CO)-α-Glu-N-(β-Asp)) des(B30) human insulin;
$N^{\varepsilon B29}$—($N^{\alpha}$-(Gly-OC(CH$_2$)$_{13}$CO)-γ-Glu) des(B30) human insulin;
$N^{\varepsilon B29}$—($N^{\alpha}$-(Sar-OC(CH$_2$)$_{13}$CO)-γ-Glu) des(B30) human insulin;
$N^{\varepsilon B29}$—($N^{\alpha}$—(HOOC(CH$_2$)$_{13}$CO)-γ-Glu) des(B30) human insulin;
($N^{\varepsilon B29}$—($N^{\alpha}$—(HOOC(CH$_2$)$_{13}$CO)-β-Asp) des(B30) human insulin;
$N^{\varepsilon B29}$—($N^{\alpha}$—(HOOC(CH$_2$)$_{13}$CO)-α-Glu) des(B30) human insulin;
$N^{\varepsilon B29}$—($N^{\alpha}$—(HOOC(CH$_2$)$_{16}$CO)-γ-D-Glu) des(B30) human insulin;
$N^{\varepsilon B29}$—($N^{\alpha}$—(HOOC(CH$_2$)$_{14}$CO)-β-D-Asp) des(B30) human insulin;
$N^{\varepsilon B29}$—(N—HOOC(CH$_2$)$_{16}$CO-β-D-Asp) des(B30) human insulin;
$N^{\varepsilon B29}$—(N—HOOC(CH$_2$)$_{14}$CO-IDA) des(B30) human insulin;
$N^{\varepsilon B29}$—[N—(HOOC(CH$_2$)$_{16}$CO)—N-(carboxyethyl)-Gly] des(B30) human insulin;
$N^{\varepsilon B29}$—[N—(HOOC(CH$_2$)$_{14}$CO)—N-(carboxyethyl)-Gly] des(B30) human insulin; and
$N^{\varepsilon B29}$—[N—(HOOC(CH$_2$)$_{14}$CO)—N-(carboxymethyl)-β-Ala] des(B30) human insulin.

In an alternative or additional embodiment of the invention the insulin is $N^{\varepsilon B29}$—($N^{\alpha}$—(HOOC(CH$_2$)$_{14}$CO)-γ-Glu) des(B30) human insulin. In an alternative or additional embodiment of the invention the insulin is $N^{\varepsilon B29}$—($N^{\alpha}$—(HOOC(CH$_2$)$_{15}$CO)-γ-Glu) des(B30) human insulin. In an alternative or additional embodiment of the invention the insulin is $N^{\varepsilon B29}$—($N^{\alpha}$—(HOOC(CH$_2$)$_{16}$CO)-γ-Glu) des(B30) human insulin. In one embodiment the insulin is $N^{\varepsilon B29}$—($N^{\alpha}$—(HOOC(CH$_2$)$_{17}$CO)-γ-Glu) des(B30) human insulin. In an alternative or additional embodiment of the invention the insulin $N^{\varepsilon B29}$—($N^{\alpha}$—(HOOC(CH$_2$)$_{18}$CO)-γ-Glu) des(B30) human insulin. In an alternative or additional embodiment of the invention the insulin is $N^{\varepsilon B29}$—($N^{\alpha}$—(HOOC(CH$_2$)$_{16}$CO)-γ-Glu-N-(γ-Glu)) des(B30) human insulin. In an alternative or additional embodiment of the invention the insulin is $N^{\varepsilon B29}$—($N^{\alpha}$-(Asp-OC(CH$_2$)$_{16}$CO)-γ-Glu) des(B30) human insulin. In an alternative or additional embodiment of the invention the insulin is $N^{\varepsilon B29}$—($N^{\alpha}$-(Glu-OC(CH$_2$)$_{14}$CO)-γ-Glu) des(B30) human insulin. In an alternative or additional embodiment of the invention the insulin is $N^{\varepsilon B29}$—($N^{\alpha}$-(Glu-OC(CH$_2$)$_{14}$CO—) des(B30) human insulin. In an alternative or additional embodiment of the invention the insulin is $N^{\varepsilon B29}$—($N^{\alpha}$-(Asp-OC(CH$_2$)$_{16}$CO—) des(B30) human insulin. In an alternative or additional embodiment of the invention the insulin is $N^{\varepsilon B29}$—($N^{\alpha}$—(HOOC(CH$_2$)$_{16}$CO)-α-Glu-N-(β-Asp)) des(B30) human insulin. In an alternative or additional embodiment of the invention the insulin is $N^{\varepsilon B29}$—($N^{\alpha}$-(Gly-OC(CH$_2$)$_{13}$CO)-γ-Glu) des(B30) human insulin. In an alternative or additional embodiment of the invention the insulin is $N^{\varepsilon B29}$—($N^{\alpha}$-(Sar-OC(CH$_2$)$_{13}$CO)-γ-Glu) des(B30) human insulin. In an alternative or additional embodiment of the invention the insulin is $N^{\varepsilon B29}$—($N^{\alpha}$—(HOOC(CH$_2$)$_{13}$CO)-γ-Glu) des(B30) human insulin. In an alternative or additional embodiment of the invention the insulin is ($N^{\varepsilon B29}$—($N^{\alpha}$—(HOOC(CH$_2$)$_{13}$CO)-β-Asp) des(B30) human insulin. In an alternative or additional embodiment of the invention the insulin is $N^{\varepsilon B29}$—($N^{\alpha}$—(HOOC(CH$_2$)$_{13}$CO)-α-Glu) des(B30) human insulin. In an alternative or additional embodiment of the invention the insulin is $N^{\varepsilon B29}$—($N^{\alpha}$—(HOOC(CH$_2$)$_{16}$CO)-γ-D-Glu) des(B30) human insulin. In an alternative or additional embodiment of the invention the insulin is $N^{\varepsilon B29}$—($N^{\alpha}$—(HOOC(CH$_2$)$_{14}$CO)-β-D-Asp) des(B30) human insulin. In an alternative or additional embodiment of the invention the insulin is $N^{\varepsilon B29}$—($N^{\alpha}$—(HOOC(CH$_2$)$_{14}$CO)-β-D-Asp) des(B30) human insulin. In an alternative or additional embodiment of the invention the insulin is $N^{\varepsilon B29}$—(N—HOOC(CH$_2$)$_{16}$CO)-β-D-Asp) des(B30) human insulin. In an alternative or additional embodiment of the invention the insulin is $N^{\varepsilon B29}$—(N—HOOC(CH$_2$)$_{14}$CO-IDA) des(B30) human insulin. In an alternative or additional embodiment of the invention the insulin is $N^{\varepsilon B29}$—[N—(HOOC(CH$_2$)$_{16}$CO)—N-(carboxyethyl)-Gly] des(B30) human insulin. In an alternative or additional embodiment of the invention the insulin is $N^{\varepsilon B29}$—[N—(HOOC(CH$_2$)$_{14}$CO)—N-(carboxyethyl)-Gly] des(B30) human insulin. In an alternative or additional embodiment of the invention the insulin is $N^{\varepsilon B29}$—[N—(HOOC(CH$_2$)$_{14}$CO)—N-(carboxymethyl)-β-Ala] des(B30) human insulin.

In an alternative or additional embodiment of the invention the insulinis provided in the form of essentially zinc free compounds or in the form of zinc complexes. When zinc complexes of a hexameric insulin or insulin derivative are provided, two Zn$^{2+}$ ions, three Zn$^{2+}$ ions or four Zn$^{2+}$ ions may be bound to each insulin hexamer. In an alternative or additional embodiment of the invention the insulin is a hexameric insulin or insulin derivative in the form of a zinc complex, wherein each insulin hexamer binds two zinc ions, three zinc ions, four zinc ions, five zinc ions, six zinc ions, seven zinc ions, eight zinc ions, nine zinc ions or ten zinc ions. Solutions of zinc complexes of the insulin derivatives will contain mixtures of such species.

Details pertaining to the preparation, formulation, pharmacology and other characteristics of relevance for the '347 derivatives are set forth in WO 2005/012347, which is hereby incorporated by reference herein.

For some embodiments, the long-acting or ultra-long-acting insulin compound has an overall hydrophobicity which is essentially similar to that of human insulin.

For some embodiments, the long-acting or ultra-long-acting insulin compound has a hydrophobic index, $k'_{rel}$, which is in the range from about 0.02 to about 10, from about 0.1 to about 5; from about 0.5 to about 5; or from about 0.5 to about 2.

For some embodiments, the long-acting or ultra-long-acting insulin compound is soluble at physiological pH values, such as pH values in the interval from about 6.5 to about 8.5.

When an insulin-like compound according to the invention is stated to be "soluble at physiological pH values" it means that the insulin derivative can be used for preparing injectable insulin compositions that are fully dissolved at physiological pH values. Such favourable solubility may either be due to the inherent properties of the insulin-like compound alone or a result of a favourable interaction between the insulin derivative and one or more ingredients contained in the vehicle.

Referring to block 306, in some embodiments the long-acting or ultra-long-acting insulin is LysB29(Nε-hexadecandioyl-γ-Glu) des(B30) human insulin (insulin degludec, Tresiba®).

Referring to block 308, in some embodiments the long-acting insulin or ultra-long-acting insulin is selected from the group consisting of a) neutral protamine hagedorn insulin (NHP insulin) (Humulin® N, Novolin® ge NPH), b) Lente Insulin (Humulin® L, Novolin® ge Lente), c) Ultralente Insulin (Humulin® U, Novolin1M ge Ultralente), d) Glargine Insulin (Lantus®), e) Detemir Insulin (Levemir®), f) Hypurin Bovine Lente, and g) Hypurin Bovine PZI. In an alternative or additional embodiment of the invention the long-acting or ultra-long acting insulin, preferably the ultra-long acting insulin, is any one or more of the compounds disclosed in WO 2005/012347, which are incorporated herein by reference. In some instances, these compounds are referred as being "the '347 derivatives".

Referring to block 310, in some embodiments the long-acting or ultra-long-acting insulin for use is administered, either concurrently or consecutively, together with one or more additional drugs used in the treatment of diabetes.

Referring to block 312, in some embodiments the one or more additional drugs used in the treatment of diabetes is, or includes, a drug selected from the group consisting of: insulins, sensitizers (such as biguanides and thiazolidinediones), secretagogues (such as sulfonylureas and non-sulfonylurea secretagogues), alpha-glucosidase inhibitors and peptide analogs (such as injectable incretin mimetics, gastric inhibitory peptide analogs, dipeptidyl peptidase-4 inhibitors and injectable amylin analogues). In an alternative or additional embodiment of the invention, the one or more additional drug used in the treatment of diabetes is, or includes, liraglutide.

Referring to block 313, in some embodiments the long-acting or ultra-long-acting insulin is LysB29(Nε-hexadecandioyl-γ-Glu) des(B30) human insulin (insulin degludec, Tresiba®), and the long-acting or ultra-long-acting insulin is administered, concurrently or consecutively, with liraglutide. In some embodiments, the long-acting or ultra-long-acting insulin and the one or more additional drug used in the treatment of diabetes may be administered concurrently in the same formulation.

Referring to block 314, in some embodiments the diabetes mellitus is type 2 diabetes mellitus. In an alternative or additional embodiment of the invention, a disease or condition where administration of insulin will be of benefit is selected from the group consisting of diabetes mellitus, such as type 1 diabetes mellitus or type 2 diabetes mellitus, other conditions characterised by hyperglycaemia (such as pre-diabetes, impaired glucose tolerance, metabolic syndrome, obesity, cachexia, in vivo beta-cell loss/death, excessive appetite and inflammation.

Referring to block 316 in FIG. 3B, in some embodiments the long-acting or ultra-long-acting insulin dose guidance recommendation is to achieve a specific glucose target. For some embodiments, the present invention is used to treat a subject whose baseline $HbA_{1c}$ level before treatment is greater than 7%, such as about 8% or 9%.

Referring to block 318 in FIG. 3B, in some embodiments the device further comprises a wireless receiver, and wherein the first data set is obtained wirelessly from a glucose sensor affixed to the subject and/or the second data set is obtained wirelessly from the one or more insulin pens.

Referring to block 320, in some embodiments the device proceeds by obtaining a first data structure that includes at least (i) a body weight of the subject, (ii) an upper limit target glucose range of the subject, (iii) a lower limit target glucose range of the subject, and (iv) an overbasalisation limit of the subject.

Referring to block 322, in some embodiments the overbasalisation limit is at least within 1.0-0.5 units/kg, 1.5-1.0 units/kg, 0.75-0.25 units/kg, 0.5-0 units/kg, or 2.0-0.75 units/kg.

Referring to block 324, in some embodiments the device proceeds by obtaining a first data structure that includes at least (i) a body weight of the subject, (ii) an upper limit target glucose range of the subject, (iii) a lower limit target glucose range of the subject, and (iv) an overbasalisation limit of the subject.

Referring to block 326, in some embodiments the starting basal dosage is updated at least within the immediately preceding 1 day, the immediately preceding 4 days, the immediately preceding 7 days, or the immediately preceding 10 days.

Referring to block 328, in some embodiments the device proceeds by obtaining a first data set, comprising a plurality of glucose measurements of the subject taken over a time course to establish a blood glucose history and, for each respective glucose measurement in the plurality of glucose measurements, a corresponding glucose timestamp representing when in the time course the respective glucose measurement was made.

Referring to block 330, in some embodiments the time course comprises a current day and the past four days.

Referring to block 332 in FIG. 3C, in some embodiments the time course comprises the current day and between one and ten of the immediately preceding past days.

Referring to block 333, in some embodiments when the blood glucose history time course contains a gap, calculate a reconstructed blood glucose history based on the blood glucose history of each calendar day.

Referring to block 334, in some embodiments the device performs a quality check of the reconstructed blood glucose history data, and when the data quality check fails, the dose guidance recommendation is not updated.

Referring to block 335, in some embodiments the device stores the updated blood glucose history in the first data structure.

Referring to block 336, in some embodiments the device proceeds by obtaining a second data set, comprising (i) a basal insulin injection history of the subject, wherein the injection history comprises a plurality of injections during all or a portion of the time course and, for each respective injection in the plurality of injections, (ii) a corresponding dose event amount and (iii) a dose event timestamp representing when in the time course the respective injection event occurred and wherein the second data set further comprises (iv) a last injection data refresh of the subject.

Referring to block 338, in some embodiments the device updates the last injection data refresh within the immediately preceding 30 seconds or less, the immediately preceding 1 minute or less, or the immediately preceding 5 minutes or less.

Referring to block 340, in some embodiments the device updates the last injection data refresh within the immediately preceding 30 seconds or less, the immediately preceding 1 minute or less, or the immediately preceding 5 minutes or less.

Referring to block 342, in some embodiments the device combines any injections in the injection history that have timestamps within a five-minute period in the time course into one injection. However, the device may also combine any injections in the injection history that have timestamps within a within 60-minute or even 120-minute period in the time course into one injection.

Referring to block 344 in FIG. 3D, in some embodiments the device proceeds by evaluating at least the first data structure, the second data structure, the first data set, and the second data set to determine whether they collectively contain a set of evaluation information comprising at least (i) the body weight of the subject, (ii) the plurality of glucose measurements of the subject taken over the time course, (iii) the injection history of the subject, (iv) the last adjustment day dose recommendation and/or the starting long-acting or ultra-long-acting insulin dose of the subject, (v) the over-basalisation limit of the subject, (vi) the last injection data refresh for the subject, (vii) the upper limit target glucose range of the subject, and (viii) the lower limit target glucose range of the subject.

Referring to block 346, in some embodiments the device provides the long-acting or ultra-long-acting insulin dose guidance recommendation when a determination is made that the at least first data structure, second data structure, first data set, and second data set collectively do contain the set of evaluation information.

Referring to block 348, in some embodiments when a determination is made that the at least first data structure, second data structure, first data set, and second data set fail to collectively contain the set of evaluation information, no update to the long-acting or ultra-long-acting insulin dose guidance recommendation is made.

Referring to block 350, in some embodiments the device updates the dose guidance recommendation for the subject, unless the injection history of the subject comprises one or more injections of the subject that have injection timestamps within the immediately preceding 4 hours or less, the immediately preceding 8 hours or less, the immediately preceding 12 hours or less, or the immediately preceding 16 hours or less.

Referring to block 352, in some embodiments the device updates the dose guidance recommendation for the subject, unless the injection history of the subject comprises one or more injections of the subject that have injection timestamps within the current day.

Referring to block 354, in some embodiments the device updates the dose guidance recommendation for the subject when at least one injection occurred within the current day and no injections occurred in the immediately preceding one day in the injection history time course.

Referring to block 356 in FIG. 3E, in some embodiments the device provides a re-recommendation of the dose guidance recommendation.

Referring to block 358, in some embodiments the device does not provide a wherein the method further comprises providing a re-recommendation of the dose guidance recommendation until: (i) one or more injections with an injection amount equivalent to the dose guidance baseline have occurred, (ii) one or more injections have occurred since the dose guidance baseline and when one or more injections have occurred over the current day and the past two or three or four days, and/or (iii) one or more does events with an injection amount greater than or equal to the dose guidance baseline have occurred.

Referring to block 360, in some embodiments the device calculates a daily titration glucose level and an overall titration glucose level.

Referring to block 362, in some embodiments the daily titration glucose level for each calendar day is calculated by selecting the lowest average of reconstructed blood glucose history data for any predetermined first time period within the injection history time course and excluding any reconstructed blood glucose history data with a timestamp older than the timestamp of the dose guidance baseline.

Referring to block 364, in some embodiments when there are gaps larger than a second predetermined time period in the injection history time course, no daily titration glucose level is calculated.

Referring to block 366, in some embodiments the predetermined second time period is between 10 minutes and 40 minutes.

Referring to block 368, in some embodiments when there are gaps larger than a second predetermined time period in the injection history time course, no daily titration glucose level is calculated.

Referring to block 370, in some embodiments the predetermined third time period is between 1 hour and 5 hours or even between 1 hour and 15 hours.

Referring to block 372 in FIG. 3F, in some embodiments when there are gaps in the injection history time course and these gaps are at least the predetermined second time period in length and less than a predetermined third time period in length within any calendar day in the injection history time course, the daily titration glucose level averaging omits any predetermined first time period containing gaps when averaging the reconstructed blood glucose history data.

Referring to block 374, in some embodiments the predetermined number of blood glucose measurements is between 20 and 100.

Referring to block 376, in some embodiments when any calendar day in the injection history time course contains gaps longer than the predetermined third time period or when more than a predetermined number of blood glucose measurements are absent no daily titration glucose level is calculated.

Referring to block 378, in some embodiments the predetermined first time period is between 15 minutes and 120 minutes.

Referring to block 380, in some embodiments the overall titration glucose level is calculated by taking the average of the daily titration glucose levels, and wherein when no overall titration glucose level can be determined the dose guidance recommendation is not updated.

Referring to block 382 in FIG. 3G, in some embodiments, responsive to receiving a request for an updated adjustment day dose recommendation, the device performs a new recommendation procedure to determine the injection amount for the updated adjustment day dose recommendation wherein the updated adjustment day dose recommendation function is based upon at least a titration glucose level and a max basal limit.

Referring to block 384, in some embodiments the titration glucose level comprises one of (i) the overall titration glucose level is greater than the upper limit target glucose range, (ii) the overall titration glucose level is greater than or equal to the lower target glucose range and the overall titration glucose level is less than or equal to the upper limit target glucose range, and/or (iii) the daily titration glucose level is less than the lower target glucose range.

Referring to block 385, in some embodiments the upper limit target glucose range used to determine the updated adjustment day dose recommendation is within 80-180 mg/dL, 90-180 mg/dL, 100-180 mg/dL, 90-200 mg/dL, 90-250 mg/dL or 90-300 mg/dL.

Referring to block 386, in some embodiments the lower target glucose range used to determine the updated adjustment day dose recommendation is within 50-70 mg/dL, 71-90 mg/dL, 71-100 mg/dL, or 61-90 mg/dL.

Referring to block 388, in some embodiments the max basal limit consists of the overbasalisation limit multiplied by the body weight of the subject, Referring to block 390, in some embodiments when the overall titration glucose level is greater than the upper limit target glucose range of the subject and when the most recent adjustment day dose recommendation is less than the max basal limit of the subject, then the updated adjustment day dose recommendation is determined to be the determined dose guidance baseline plus a predetermined number of units of long-acting or ultra-long-acting insulin.

Referring to block 391, in some embodiments the predetermined number of units of long-acting or ultra-long-acting insulin by which to alter the adjustment day dose recommendation is selected from the set of at least 1 unit, 2 units, 4 units, 6 units and 8 units.

Referring to block 392 in FIG. 3H, in some embodiments when the overall titration glucose level is greater than the upper limit target glucose range of the subject and when the most recent adjustment day dose recommendation is greater than or equal to the max basal limit of the subject, then the updated adjustment day dose recommendation is determined to be the determined dose guidance baseline.

Referring to block 394, in some embodiments when the overall titration glucose level is between the upper limit target glucose range of the subject and the lower target glucose range of the subject, then the updated adjustment day dose recommendation is determined to be the determined dose guidance baseline.

Referring to block 396, in some embodiments when the daily titration glucose level is less than the lower target glucose range of the subject, then the updated adjustment day dose recommendation is determined to be the determined dose guidance baseline minus a predetermined number of units of long-acting or ultra-long-acting insulin.

Referring to block 397, in some embodiments the predetermined number of units of long-acting or ultra-long-acting insulin by which to alter the adjustment day dose recommendation is selected from the set of at least 1 unit, 2 units, 4 units, 6 units and 8 units.

Referring to block 398, in some embodiments the device provides the updated adjustment day dose recommendation at least with the immediately preceding 1 day, the immediately preceding 4 days, the immediately preceding 7 days, or the immediately preceding 10 days.

FIGS. 4A-D illustrate an example method 400 (e.g. performed at an electronic device) for providing an adjusted day dose recommendation to the subject. In some embodiments, the method of FIGS. 4A-D is performed when the subject has not previously been provided with an adjusted day dose recommendation. In some embodiments, the method of FIG. 4 is performed to provide a re-recommendation of a previously provided adjusted day dose recommendation. In some embodiments, the method of FIGS. 4A-D is performed to provide an updated adjusted day dose recommendation, subsequent to providing one or more previous adjusted day dose recommendations.

Figure 4A:
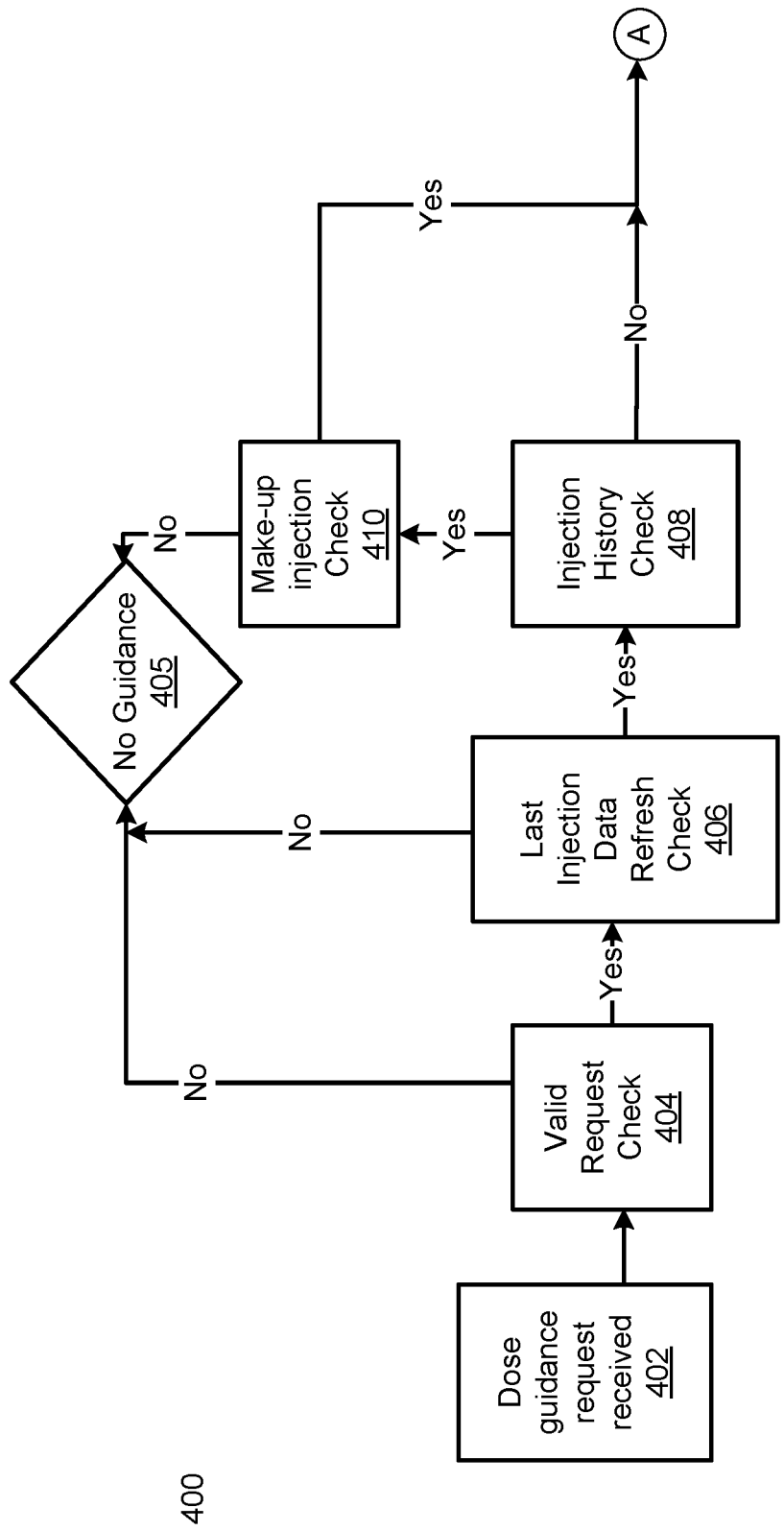
FIGS. 4A, 4B, 4C, and 4D collectively illustrate a dose guidance request for a subject, in accordance with an embodiment of the present disclosure.
Figure 4B:
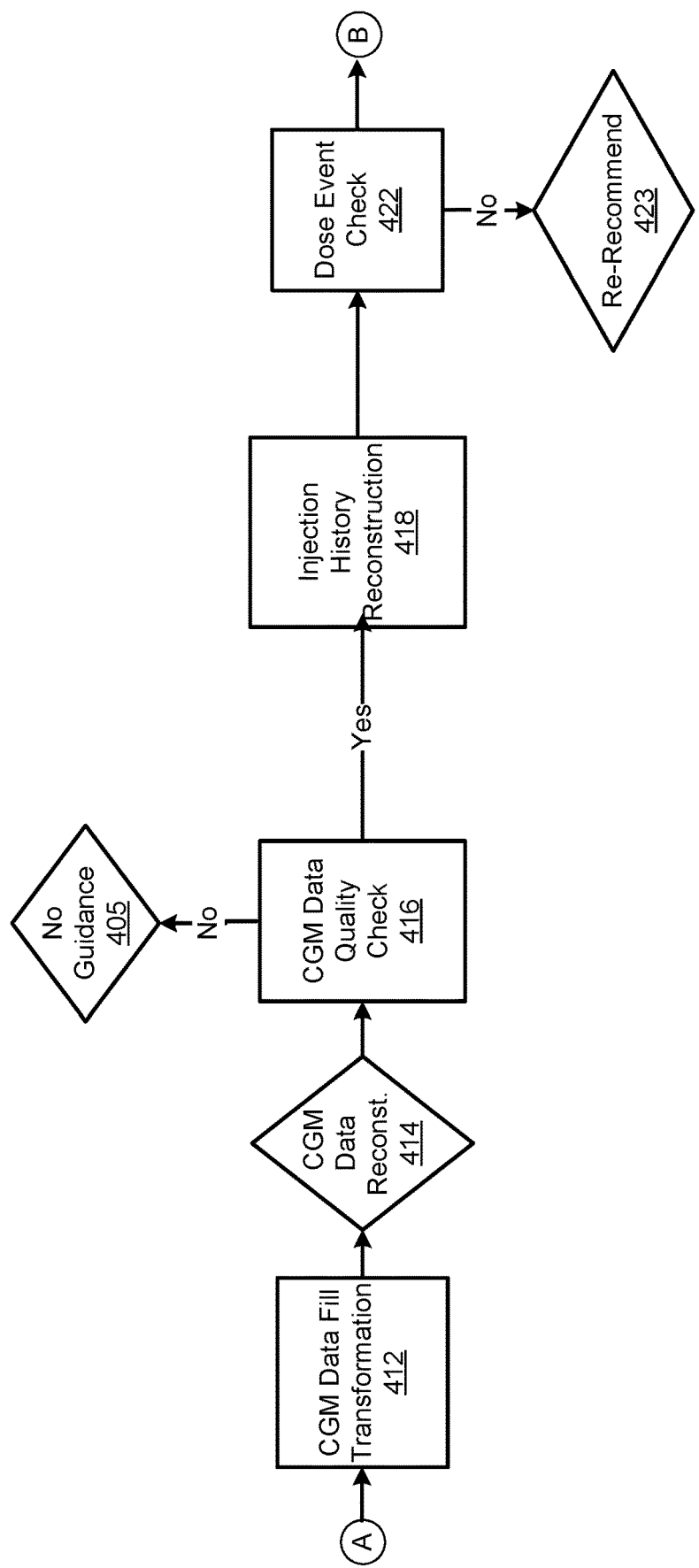
Figure 4C:
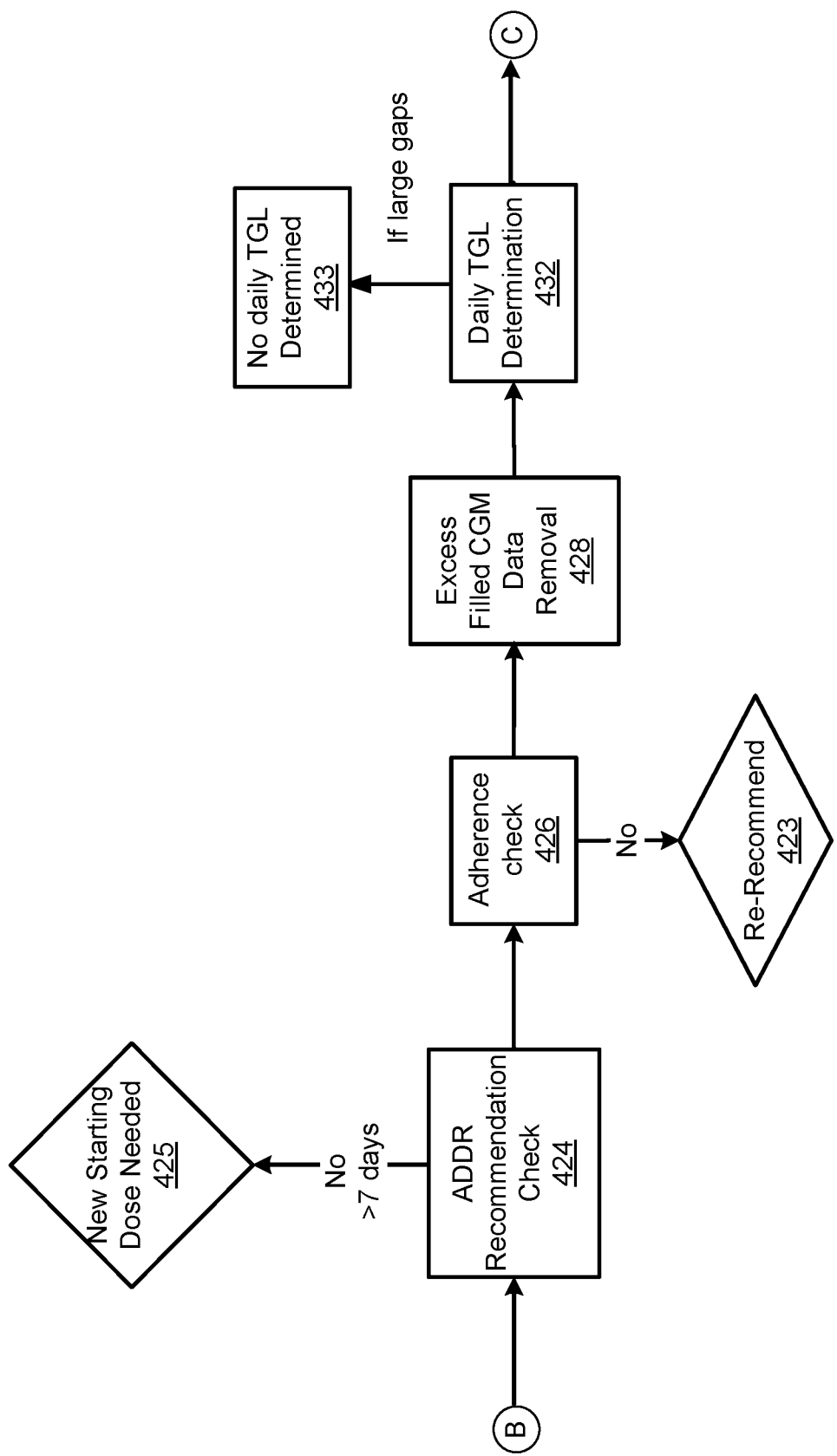
Figure 4D:
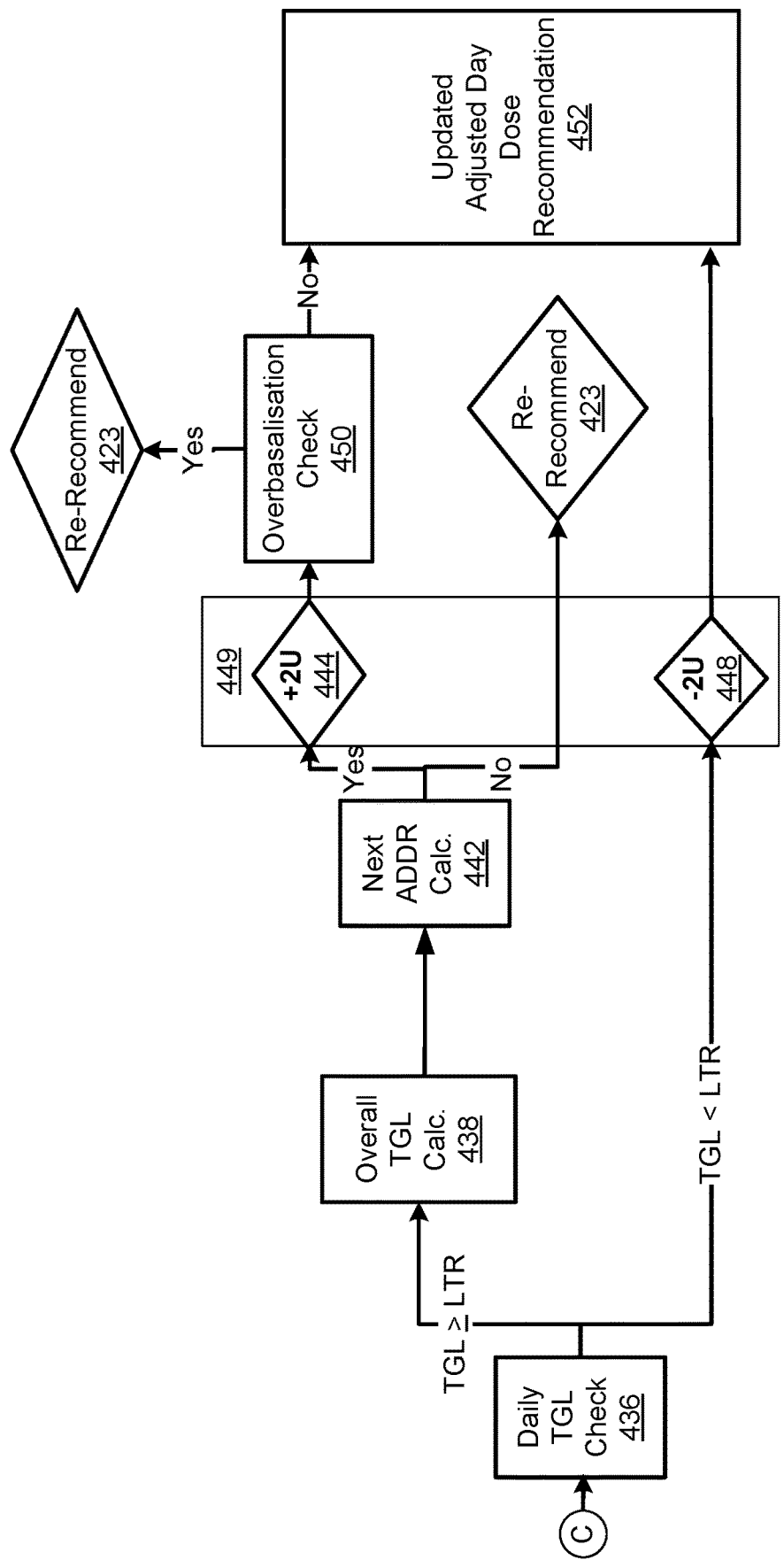

Referring to FIG. 4A, the device receives a dose guidance request 402. In some embodiments, the dose guidance request is automatically generated. In some embodiments, the user makes a specific request for dose guidance. The device proceeds and checks 404 that the request is valid (e.g. the device confirms that the requisite or required data is included in the request—e.g. one or more of a body weight of the subject, an upper target glucose range of the subject, a lower limit target glucose range of the subject, an overbasilisation of the subject, a previous adjustment day dose and/or a starting basal insulin dose, a blood glucose history of the subject, a basal insulin injection history of the subject and an injection data refresh of the subject). If the dose guidance request does not contain the necessary data, the device ends the process 405, provides no guidance, and optionally advises the user to return later with the proper data. In some embodiments, the device advises the user what data is missing or suggests the user seek assistance with their medical devices. If the dose guidance request contains the appropriate information, the device checks 406 the timestamp of the last injection data refresh. In some embodiments, the device provides no guidance if the last injection data refresh occurred more than 30 seconds previously, or more than 1 minute previously, or more than 5 minutes previously. If the check 406 indicates that the injection data refresh occurred within an appropriate time period, the process continues.

The device proceeds and performs a check 408 of the injection history of the subject. In some embodiments, if the injection history of the subject includes one or more injections with injection timestamps within the immediately preceding 4 hours or less, the immediately preceding 8 hours or less, the immediately preceding 12 hours or less, or the immediately preceding 16 hours or less, the device checks 410 whether the dose guidance request is for a make-up injection. If the previous calendar day in the injection history is lacking an injection timestamp, the device proceeds with the process. If the previous calendar day in the injection history contains an injection timestamp, the device ends the process 405, provides no guidance, and optionally advises the user to return later. If the most recent injection timestamp in the injection history occurred more than 4 hours ago, or more than 8 hours ago, or more than 12 hours ago, or more than 16 hours ago, the device proceeds.

The device performs 412 a transformation of blood glucose history data. In some embodiments, this reconstruction of blood glucose history data is to fill in gaps of missing data (e.g. if the blood glucose measurements have not been updated or recorded in full). The device proceeds with the reconstructed blood glucose measurements 414 (in some embodiments, the blood glucose measurements consist of continuous glucose monitoring data) and performs a quality check 416 of the data. If the quality check fails (e.g. if the blood glucose measurements and/or the reconstructed blood glucose measurements are deemed insufficient), the device end the process 405, provides no guidance, and optionally advises the user that their blood glucose monitoring equipment may be encountering difficulties or need adjustment. In some embodiments, the quality check assesses whether there is sufficient blood glucose or reconstructed blood glucose data to determine total daily glucose levels. If the quality check approves the blood glucose data and/or the reconstructed blood glucose data, the device proceeds.

The device performs an injection history reconstruction 418. In some embodiments, the reconstruction consists of combining the injection amounts of all injection events that occur within 5 minutes of each other, or that occur within 10 minutes of each other, or that occur within 15 minutes of each other into one injection event (e.g. to ensure that priming injections are not recorded as separate amounts for future calculations). The device proceeds.

The device performs an injection event check 422. In some embodiments, the injection event check consists of determining if three or more injection events have occurred since the previous dose guidance recommendation has been provided to the subject. In some embodiments, the injection event check consists of determining if three or more injection events have occurred in the current calendar day and the immediately preceding 4 calendar days (e.g. to ensure adherence of the subject to the previous dose guidance recommendation). In some embodiments, the injection event check consists of determining if three or more injection events with injection amounts greater than or equal to the dose guidance baseline have been administered. In some embodiments, the injection event check consists of any or all features of any of the other embodiments combined. If the device determines that the subject fails the injection event check, the device ends the process 423 and provides a re-recommendation of the previous dose guidance recommendation. If the device determines that the subject has complied with the injection event check, the device proceeds.

The device performs an adjusted day dose recommendation check 424. In some embodiments, the adjusted day dose recommendation check consists of determining whether the most recent adjustment day dose recommendation was made within the immediately preceding 3 calendar days, within the immediately preceding 5 calendar days, within the immediately preceding 7 calendar days, within the immediately preceding 10 calendar days, or within the immediately preceding 14 calendar days. If the device determines that the subject fails the adjustment day dose recommendation check, the device end the process 425 and determines a new starting dose for the dose guidance recommendation. If the device determines that the subject has complied with the adjustment day dose recommendation check, the device proceeds.

The device performs an adherence check 426. In some embodiments, the adherence check consists of determining whether the subject has adhered to the adjusted day dose recommendation (e.g. by administering three or more injection events that at least have the same injection amount as the most recent adjusted day dose recommendation). If the device determines that the subject fails the adherence check, the device ends the process 423 and provides a re-recommendation of the previous dose guidance recommendation. If the device determines that the subject has complied with the adjustment day dose recommendation check, the device proceeds.

The device performs a removal of excess reconstructed blood glucose history data 428. In some embodiments, the excess blood glucose history removal consists of removing data from one or more previous days from consideration (e.g. any data that is older than the most recent adjustment day dose recommendation).

The device determines 432 a titration glucose level for every calendar day included in the altered reconstructed blood glucose history data. In some embodiments the daily titration glucose level is calculated by selecting the lowest average of reconstructed blood glucose history data for any predetermined first time period within the injection history time course and excluding any reconstructed blood glucose history data with a timestamp older than the timestamp of the dose guidance baseline. In some embodiments, when there are gaps in the reconstructed blood glucose data that are larger than a second predetermined time period in the injection history time course, the device does not calculate a daily titration glucose level 433. In some embodiments, when there are gaps in the injection history time course and these gaps are at least the predetermined second time period in length and less than a predetermined third time period in length within any calendar day in the injection history time course, the daily titration glucose level averaging omits any predetermined first time period containing gaps when averaging the reconstructed blood glucose history data. In some embodiments, when any calendar day in the injection history time course contains gaps longer than the predetermined third time period or when more than a predetermined number of blood glucose measurements are absent, the device does not calculate a daily titration glucose level. In some embodiments, the predetermined first time period is between 15 minutes and 120 minutes. In some embodiments, the predetermined second time period is between 10 minutes and 40 minutes. In some embodiments, the predetermined third time period is between 1 hour and 15 hours. In some embodiments, the predetermined number of blood glucose measurements is between 20 and 100.

The device performs a daily titration glucose check 436. In some embodiments, the daily titration glucose check consists of comparing the daily titration glucose levels with the lower target glucose range of the subject. In some embodiments, if any daily titration glucose level from the injection history is less than the lower target glucose range of the subject, the device proceeds and provides an updated adjusted day dose recommendation 452 by subtracting a predetermined number of units of basal insulin 448 from the most recent adjusted day dose recommendation. In some embodiments, if the daily titration glucose levels are all greater than or equal to the lower target glucose range of the subject, the device proceeds and performs an overall titration glucose level calculation 438. In some embodiments, the overall titration glucose level calculation, consists of taking the average of all the daily titration glucose levels.

The device performs the next adjusted day dose recommendation calculation 442. In some embodiments, the next adjusted day dose recommendation consists of comparing the overall daily titration glucose level to the upper target glucose range. In some embodiments, if the overall daily titration glucose level is greater than the upper target glucose range, the device proceeds and calculates an updated adjusted day dose recommendation 449 by adding a predetermined number of units of basal insulin 444 to the most recent adjusted day dose recommendation. The device proceeds and performs an overbasalisation check 450. If the device determines that the most recent adjusted day dose recommendation is greater than or equal to the max basal limit of the subject, the device ends the process and provides a re-recommendation 423 of the most recent adjusted day dose recommendation. If the device determines that the most recent adjusted day dose recommendation is less than the max basal limit of the subject, the device provides 452 the calculated adjusted day dose recommendation 444 as the updated adjusted day dose recommendation. In some embodiments, if the overall daily titration glucose level is less than or equal to the upper target glucose range, the device proceeds provides a re-recommendation of the most recent adjusted day dose recommendation 423. In some embodiments, the predetermined number of units of insulin by which to alter the adjustment day dose recommendation is selected from the set of at least 1 unit, 2 units, 4 units, and 6 units.

Referring to FIG. 5, with the integrated system 502, autonomous timestamped insulin injection and blood glucose measurements of the subject are obtained 520. Also, in some embodiments, data from the one or more insulin pens 104 used to apply a prescribed insulin regimen to the subject is obtained 540 as a plurality of records. Each record comprises a timestamped event specifying an amount of injected long-acting or ultra-long-acting insulin medicament that the subject received as part of the prescribed insulin medicament dosage regimen. The glucose measurements (e.g., the blood glucose history) are quality assessed 504, and a reconstructed blood glucose history is calculated when necessary. The blood glucose history or the reconstructed blood glucose history is stored in non-transitory memory 506. The memory 506 includes instructions that, when executed by the one or more processors, perform a method responsive to receiving a dose guidance request. In this way, the glucose data is analyzed 508 along with further data regarding the subject (e.g., subject parameters 512), and a dose guidance recommendation (DGR) is provided 510 (e.g., to adjust the long acting insulin medicament dosage) in accordance with the methods of the present disclosure.

In some embodiments, the dose guidance request includes obtaining a first data structure (e.g., subject parameters) 512 that contains at least (i) a body weight (BW) of the subject, (ii) an upper limit target glucose range (UTR) of the subject, (iii) a lower limit target glucose range (LTR) of the subject, and (iv) an overbasalisation limit (OBL) of the subject. In some embodiments, the dose guidance request also includes obtaining a second data structure 226 (the dose guidance baseline) that contains at least (i) a most recent adjustment day dose recommendation (ADDR) and/or (ii) a starting basal dose (SBD). In some embodiments, the dose guidance request also includes obtaining a first data set 520 that includes a plurality of glucose measurements of the subject taken over a time course to establish a blood glucose history (BGH) and, for each respective glucose measurement in the plurality of glucose measurements, a corresponding glucose timestamp representing when in the time course the respective glucose measurement was made. In some embodiments, the dose guidance request also includes obtaining a second data set 540 comprising (i) a basal insulin injection history (IH) of the subject, wherein the injection history comprises a plurality of injections during all or a portion of the time course and, for each respective injection in the plurality of injections, (ii) a corresponding dose event amount (IU) and (iii) a dose event timestamp (UTC) representing when in the time course the respective injection event occurred and where the second data set further comprises (iv) a last injection data refresh (IDR) of the subject.

In some embodiments, the dose guidance request also includes evaluating at least the first data structure, the second data structure, the first data set, and the second data set to determine whether they collectively contain a set of evaluation information comprising at least (i) the body weight of the subject, (ii) the plurality of glucose measurements of the subject taken over the time course, (iii) the injection history of the subject, (iv) the last adjustment day dose recommendation and/or the starting long-acting or ultra-long-acting insulin dose of the subject, (v) the overbasalisation limit of the subject, (vi) the last injection data refresh for the subject, (vii) the upper limit target glucose range of the subject, and (viii) the lower limit target glucose range of the subject. When a determination is made that the at least first data structure, second data structure, first data set, and second data set fail to collectively contain the set of evaluation information, no update to the long-acting or ultra-long-acting insulin dose guidance recommendation is made. When a determination is made that the at least first data structure, second data structure, first data set, and second data set collectively do contain the set of evaluation information, the method further comprises providing the long-acting or ultra-long-acting insulin dose guidance recommendation 510.

In some embodiments, the administration of the long-acting or ultra-long-acting insulin includes one data structure includes (a) recording (520) a plurality of glucose measurements of a subject in need of treatment taken over a time course and, for each respective glucose measurement in the plurality of glucose measurements, a corresponding glucose timestamp representing when in the time course the respective glucose measurement was made. The administration continues with (b) obtaining (512) in a data structure the (i) a body weight of the subject, (ii) an upper limit target glucose range of the subject, (iii) a lower limit target glucose range of the subject, (iv) an overbasalisation limit of the subject, (v) a most recent adjustment day dose recommendation and/or a starting insulin basal dose of the subject, (vi) a basal insulin injection history of the subject, wherein the injection history comprises a plurality of injections during all or a portion of the time course and, for each respective injection in the plurality of injections, a corresponding injection amount and an injection timestamp representing when in the time course the respective injection occurred, and (vii) a last injection data refresh of the subject. The administration continues (c) with using (508) the blood glucose measurements (e.g., the blood glucose history or the reconstructed blood glucose history) and the above data structure to (d) provide an updated adjustment day dose recommendation (510) of the long-acting or ultra-long-acting insulin injection amount to the subject.

In some embodiments, the provision of an updated adjustment day dose recommendation of the administration of the long-acting or ultra-long-acting insulin is performed for an administration period of, or at least of, 1 day; for example, of, or at least of, 2 days; of, or at least of, 3 days; of, or at least of, 4 days; of, or at least of, 5 days; of, or at least of, 6 days; of, or at least of, 7 days; of, or at least of, 8 days; of, or at least of, 9 days; of, or at least of, 10 days; of, or at least of, 11 days; of, or at least of, 12 days; of, or at least of, 13 days; of, or at least of, 14 days; or at least of, 15 days; or for an administration period of between 1 and 15 days, for example, between 1 and 13 days; between 2 and 12 days; between 3 and 11 days; between 4 and 10 days; between 5 and 9 days; or for an administration period of between 6 and 8 days.

Insulin dose may be determined through a variety of methods, for example, may be calculated based on weight (and/or height), fasting blood glucose and gender (thereafter adjusted empirically according to fast blood glucose and/or $HbA_{1c}$ level outcome). It is increasingly common to use a titration method wherein, after administering an initial dose standard or empirically-determined dose, further doses are adjusted by pre-determined increments (e.g. titration algorithm), as necessary, based on blood glucose/plasma measurements in order to reach and maintain a target blood glucose/plasma and/or $HbA_{1c}$ level. Such titration models are however always given as guidance only and individual adjustments are applicable on a case by case basis.

Specific Embodiments

In one aspect, the disclosure provides a device for providing a long-acting or ultra-long-acting insulin dose guidance recommendation for a subject to treat diabetes mellitus, wherein the device comprises one or more processors and a memory, the memory comprising: instructions that, when executed by the one or more processors, perform a method responsive to receiving a dose guidance request (DGR) comprising: obtaining a first data structure that comprises at least (i) a body weight (BW) of the subject, (ii) an upper limit target glucose range (UTR) of the subject, (iii) a lower limit target glucose range (LTR) of the subject, and (iv) an overbasalisation limit (OBL) of the subject; obtaining a second data structure that comprises at least (i) a most recent adjustment day dose recommendation (ADDR) and/or (ii) a starting basal dose (SBD); obtaining a first data set, comprising a plurality of glucose measurements of the subject taken over a time course to establish a blood glucose history (BGH) and, for each respective glucose measurement in the plurality of glucose measurements, a corresponding glucose timestamp representing when in the time course the respective glucose measurement was made, obtaining a second data set, comprising (i) a basal insulin injection history (IH) of the subject, wherein the injection history comprises a plurality of injections during all or a portion of the time course and, for each respective injection in the plurality of injections, (ii) a corresponding injection amount (IU) and (iii) an injection timestamp (UTC) representing when in the time course the respective injection occurred and wherein the second data set further comprises (iv) a last injection data refresh (IDR) of the subject; and evaluating at least the first data structure, the second data structure, the first data set, and the second data set to determine whether they collectively contain a set of evaluation information comprising at least (i) the body weight of the subject, (ii) the plurality of glucose measurements of the subject taken over the time course, (iii) the injection history of the subject, (iv) the last adjustment day dose recommendation and/or the starting long-acting or ultra-long-acting insulin dose of the subject, (v) the overbasalisation limit of the subject, (vi) the last injection data refresh for the subject, (vii) the upper limit target glucose range of the subject, and (viii) the lower limit target glucose range of the subject, wherein when a determination is made that the at least first data structure, second data structure, first data set, and second data set fail to collectively contain the set of evaluation information, no update to the long-acting or ultra-long-acting insulin dose guidance recommendation is made, and when a determination is made that the at least first data structure, second data structure, first data set, and second data set collectively do contain the set of evaluation information, the method further comprises providing the long-acting or ultra-long-acting insulin dose guidance recommendation.

In one aspect, the disclosure provides a long-acting or ultra-long-acting insulin for use in treating diabetes mellitus, wherein the administration of the long-acting or ultra-long-acting insulin comprises or consists of the following steps: (a) recording a plurality of glucose measurements of a subject in need of treatment taken over a time course and, for each respective glucose measurement in the plurality of glucose measurements, a corresponding glucose timestamp representing when in the time course the respective glucose measurement was made; (b) obtaining a data structure that comprises at least: (i) a body weight (BW) of the subject, (ii) an upper limit target glucose range (UTR) of the subject, (iii) a lower limit target glucose range (LTR) of the subject, (iv) an overbasalisation limit (OBL) of the subject, (v) a most recent adjustment day dose recommendation (ADDR) and/or a starting insulin basal dose (SBD) of the subject, (vi) a basal insulin injection history (IH) of the subject, wherein the injection history comprises a plurality of injections during all or a portion of the time course and, for each respective injection in the plurality of injections, a corresponding injection amount (IU) and an injection timestamp (UTC) representing when in the time course the respective injection occurred, and (vii) a last injection data refresh (IDR) of the subject; (c) using the glucose measurements and said data structure and (d) providing an updated adjustment day dose recommendation of the long-acting or ultra-long-acting insulin injection amount to the subject.

In one aspect, the disclosure provides wherein step (d) is performed for an administration period of, or at least of, 1 day; for example, of, or at least of, 2 days; of, or at least of, 3 days; of, or at least of, 4 days; of, or at least of, 5 days; of, or at least of, 6 days; of, or at least of, 7 days; of, or at least of, 8 days; of, or at least of, 9 days; of, or at least of, 10 days; of, or at least of, 11 days; of, or at least of, 12 days; of, or at least of, 13 days; of, or at least of, 14 days; of, or at least of, 15 days; or for an administration period of between 1 and 15 days, for example, between 1 and 13 days; between 2 and 12 days; between 3 and 11 days; between 4 and 10 days; between 5 and 9 days; or for an administration period of between 6 and 8 days.

In some embodiments, the administration of said insulin comprises or consists of steps (a) to (d) and the following step: (e) repeating steps (a) to (d).

In some embodiments, steps (a) to (c) are performed on the same day, wherein, in step (d), said insulin is administered for an administration period of between 1 and 15 days, preferably between 5 and 9 days, between 6 and 8 days, or most preferably of 7 days, and starting on the same day as steps (a) to (c), and wherein said steps (a) to (d) are repeated continuously as long as needed by the said individual.

In some embodiments, the long-acting or ultra-long-acting insulin, preferably ultra-long-acting insulin, has a side chain attached to the α-amino group of the N-terminal amino acid residue of the B chain or to the ε-amino group of the Lys residue present in the B chain of the parent insulin, the side chain being of the general formula:

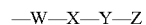

—W—X—Y—Z wherein W is: (i) an α-amino acid residue having a carboxylic acid group in the side chain which residue forms, with one of its carboxylic acid groups, an amide group together with the α-amino group of the N-terminal amino acid residue of the B chain or together with the ε-amino group of a Lys residue present in the B chain of the parent insulin; (ii) a chain composed of two, three or four α-amino acid residues linked together via amide bonds, which chain—via an amide bond—is linked to the α-amino group of the N-terminal amino acid residue of the B chain or to the ε-amino group of a Lys residue present in the B chain of the parent insulin, the amino acid residues of W being selected from the group of amino acid residues having a neutral side chain and amino acid residues having a carboxylic acid group in the side chain so that W has at least one amino acid residue which has a carboxylic acid group in the side chain; or (iii) a covalent bond from X to the α-amino group of the N-terminal amino acid residue of the B chain or to the ε-amino group of a Lys residue present in the B chain of the parent insulin; wherein X is: (i) —CO—; (ii) —COCH(COOH)CO—; (iii) —CON(CH$_2$COOH)CH$_2$CO—; (iv) CON(CH$_2$COOH)CH$_2$CON(CH$_2$COOH)CH$_2$CO—; (v) —CON(CH$_2$CH$_2$COOH)CH$_2$CH$_2$CO—; (vi) —CON(CH$_2$CH$_2$COOH)CH$_2$CH$_2$CON(CH$_2$CH$_2$COOH)CH$_2$CH$_2$CO—; (vii) —CONHCH(COOH)(CH$_2$)$_4$NHCO—; (viii) —CON(CH$_2$CH$_2$COOH)CH$_2$CO—; or (ix) —CON(CH$_2$COOH)CH$_2$CH$_2$CO—; provided that: (a) when W is an amino acid residue or a chain of amino acid residues, via a bond from the underscored carbonyl carbon forms an amide bond with an amino group in W; or (b) when W is a covalent bond, via a bond from the underscored carbonyl carbon forms an amide bond with the N-terminal α-amino group in the B chain or with the ε-amino group of a Lys residue present in the B chain of the parent insulin; wherein Y is: (i) a —(CH$_2$)$_m$— where m is an integer in the range of 6 to 32; (ii) a divalent hydrocarbon chain comprising 1, 2 or 3 —CH=CH— groups and a number of —CH$_2$— groups sufficient to give a total number of carbon atoms in the chain in the range of 10 to 32; or (iii) a divalent hydrocarbon chain of the formula —(CH$_2$)$_v$C$_6$H(CH$_2$)$_w$— wherein v and w are integers or one of them is zero so that the sum of v and w is in the range of 6 to 3 0; wherein Z is: (i) —COOH; (ii) —CO-Asp; (iii) —CO-Glu; (iv) —CO-Gly; (v) —CO-Sar; (vi) —CH(COOH)$_2$; (vii) —N(CH$_2$COOH)$_2$; (viii) —SO$_3$H; or (ix) —PO$_3$H; and any Zn$^{2+}$ complexes thereof, provided that when W is a covalent bond and X is —CO—, then Z is different from —COOH.

In some embodiments, said insulin is LysB29(Nε-hexadecandioyl-γ-Glu) des(B30) human insulin (insulin degludec, Tresiba®).

In some embodiments, the long-acting insulin or ultra-long-acting insulin is selected from the group consisting of: a) neutral protamine hagedorn insulin (NHP insulin) (Humulin® N, Novolin® ge NPH); b) Lente Insulin (Humulin® L, Novolin® ge Lente); c) Ultralente Insulin (Humulin® U, Novolin1M ge Ultralente); d) Glargine Insulin (Lantus®); e) Detemir Insulin (Levemir®); f) Hypurin Bovine Lente; and g) Hypurin Bovine PZI.

In some embodiments, the long-acting or ultra-long-acting insulin for use is administered, either concurrently or consecutively, together with one or more additional drugs used in the treatment of diabetes.

In some embodiments, the one or more additional drug used in the treatment of diabetes is, or includes, a drug selected from the group consisting of: insulins, sensitizers (such as biguanides and thiazolidinediones), secretagogues (such as sulfonylureas and nonsulfonylurea secretagogues), alpha-glucosidase inhibitors and peptide analogs (such as injectable incretin mimetics, gastric inhibitory peptide analogs, dipeptidyl peptidase-4 inhibitors and injectable amylin analogues).

In some embodiments, the long-acting or ultra-long-acting insulin is LysB29(Nε-hexadecandioyl-γ-Glu) des(B30) human insulin (insulin degludec, Tresiba®), and the long-acting or ultra-long-acting insulin is administered, concurrently or consecutively, with liraglutide.

In some embodiments, the diabetes mellitus is type 2 diabetes mellitus.

In some embodiments, the time course comprises a current day and the past four days.

In some embodiments, the time course comprises the current day and between one and ten of the immediately preceding past days.

In some embodiments, the device further comprises updating the last injection data refresh within the immediately preceding 30 seconds or less, the immediately preceding 1 minute or less, or the immediately preceding 5 minutes or less.

In some embodiments, the device further comprises updating the dose guidance recommendation for the subject, unless the injection history of the subject comprises one or more injections of the subject that have injection timestamps within the immediately preceding 4 hours or less, the immediately preceding 8 hours or less, the immediately preceding 12 hours or less, or the immediately preceding 16 hours or less.

In some embodiments, the device further comprises updating the dose guidance recommendation for the subject, unless the injection history of the subject comprises one or more injections of the subject that have injection timestamps within the current day.

In some embodiments, the device further comprises updating the dose guidance recommendation for the subject when at least one injection occurred within the current day and no injections occurred in the immediately preceding one day in the injection history time course.

In some embodiments, the device further comprises combining any injections in the injection history that have timestamps within a five-minute period in the time course into one inj ecti on.

In some embodiments, the device further comprises calculating a reconstructed blood glucose history of the subject when the blood glucose history time course contains a gap, and wherein the reconstructed blood glucose history is calculated based on the blood glucose history of each calendar day.

In some embodiments, the device further comprises performing a quality check of the reconstructed blood glucose history data, and wherein when the data quality check fails, the dose guidance recommendation is not updated.

In some embodiments, the device further comprises providing a re-recommendation of the dose guidance recommendation until: (i) one or more injections with an injection amount equivalent to the dose guidance baseline have occurred, (ii) one or more injections have occurred since the dose guidance baseline and when one or more injections have occurred over the current day and the past two or three or four days, and (iii) one or more does events with an injection amount greater than or equal to the dose guidance baseline have occurred.

In some embodiments, the device further comprises selecting the dose guidance baseline from the set of parameters comprising at least the starting basal dose and the most recent adjustment day dose recommendation, and wherein the selected parameter has the timestamp closest to the current time.

In some embodiments, the device further comprises calculating a daily titration glucose level and an overall titration glucose level, wherein: (i) the daily titration glucose level for each calendar day is calculated by selecting the lowest average of reconstructed blood glucose history data for any predetermined first time period within the blood glucose history time course and excluding any reconstructed blood glucose history data with a timestamp older than the timestamp of the dose guidance baseline: when there are gaps larger than a second predetermined time period in the blood glucose history time course, no daily titration glucose level is calculated, when there are gaps in the blood glucose history time course and these gaps are at least the predetermined second time period in length and less than a predetermined third time period in length within any calendar day in the blood glucose history time course, the daily titration glucose level averaging omits any predetermined first time period containing gaps when averaging the reconstructed blood glucose history data, when any calendar day in the blood glucose history time course contains gaps longer than the predetermined third time period or when more than a predetermined number of blood glucose measurements are absent no daily titration glucose level is calculated; and (ii) the overall titration glucose level is calculated by taking the average of the daily titration glucose levels, and wherein when no overall titration glucose level can be determined the dose guidance recommendation is not updated.

In some embodiments, the predetermined first time period is between 15 minutes and 120 minutes.

In some embodiments, the predetermined second time period is between 10 minutes and 40 minutes.

In some embodiments, the predetermined third time period is between 1 hour and 5 hours or between 1 hour and 15 hours.

In some embodiments, the predetermined number of blood glucose measurements is between 20 and 100.

In some embodiments, the device further comprises: responsive to receiving a request for an updated adjustment day dose recommendation performing a new recommendation procedure to determine the injection amount for the updated adjustment day dose recommendation wherein the updated adjustment day dose recommendation function is based upon at least a titration glucose level and a max basal limit.

In some embodiments, the titration glucose level comprises one of (i), (ii), or (iii): (i) the overall titration glucose level is greater than the upper limit target glucose range, (ii) the overall titration glucose level is greater than or equal to the lower target glucose range and the overall titration glucose level is less than or equal to the upper limit target glucose range, (iii) the daily titration glucose level is less than the lower target glucose range.

In some embodiments, the max basal limit consists of the overbasalisation limit multiplied by the body weight of the subject.

In some embodiments, when the overall titration glucose level is greater than the upper limit target glucose range of the subject and when the most recent adjustment day dose recommendation is less than the max basal limit of the subject, then the updated adjustment day dose recommendation is determined to be the determined dose guidance baseline plus a predetermined number of units of long-acting or ultra-long-acting insulin.

In some embodiments, when the overall titration glucose level is greater than the upper limit target glucose range of the subject and when the most recent adjustment day dose recommendation is greater than or equal to the max basal limit of the subject, then the updated adjustment day dose recommendation is determined to be the determined dose guidance baseline.

In some embodiments, when the overall titration glucose level is between the upper limit target glucose range of the subject and the lower target glucose range of the subject, then the updated adjustment day dose recommendation is determined to be the determined dose guidance baseline.

In some embodiments, wherein when the daily titration glucose level is less than the lower target glucose range of the subject, then the updated adjustment day dose recommendation is determined to be the determined dose guidance baseline minus a predetermined number of units of long-acting or ultra-long-acting insulin.

In some embodiments, the predetermined number of units of long-acting or ultra-long-acting insulin by which to alter the adjustment day dose recommendation is selected from the set of at least 1 unit, 2 units, 4 units, 6 units and 8 units.

In some embodiments, the long-acting or ultra-long-acting insulin dose guidance recommendation is to achieve a specific glucose target.

In some embodiments, the device further comprises a wireless receiver, and wherein the first data set is obtained wirelessly from a glucose sensor affixed to the subject and/or the second data set is obtained wirelessly from the one or more insulin pens.

In some embodiments, the device further comprises storing the updated blood glucose history in the first data structure, and wherein the method is repeated on a recurring basis.

In some embodiments, the upper limit target glucose range used to determine the updated adjustment day dose recommendation is within 80-180 mg/dL, 90-180 mg/dL, 100-180 mg/dL, 90-200 mg/dL, 90-250 mg/dL or 90-300 mg/dL.

In some embodiments, the lower target glucose range used to determine the updated adjustment day dose recommendation is within 50-70 mg/dL, 71-90 mg/dL, 71-100 mg/dL, or 61-90 mg/dL.

In some embodiments, the device further comprises updating the starting basal dosage at least within the immediately preceding 1 day, the immediately preceding 4 days, the immediately preceding 7 days, or the immediately preceding 10 days.

In some embodiments, the device further comprises providing the updated adjustment day dose recommendation at least within the immediately preceding 1 day, the immediately preceding 4 days, the immediately preceding 7 days, or the immediately preceding 10 days.

In some embodiments, the overbasilisation limit is at least within 1.0-0.5 units/kg, 1.5-1.0 units/kg, 0.75-0.25 units/kg, 0.5-0 units/kg, or 2.0-0.75 units/kg.

EXAMPLES

Example 1—Insulin Degludec Once-Daily in Type 2 Diabetes: Simple or Step-Wise Titration (BEGIN™: ONCE SIMPLE USE)

Abstract

Introduction

Insulin degludec (IDeg) is a new basal insulin in development with a flat, ultra-long action profile that may permit dosing using a simplified titration algorithm with less frequent self-measured blood glucose (SMBG) measurements and more simplified titration steps than currently available basal insulins.

Methods:

This 26-week, multi-center, open-label, randomized, treat-to-target study compared the efficacy and safety of IDeg administered once daily in combination with metformin in insulin-naïve subjects with type 2 diabetes using two different patient-driven titration algorithms: a "Simple" algorithm (IDeg$_{Simple}$), with dose adjustments based on one pre-breakfast SMBG measurement (N=111) versus a "Step-wise" algorithm (IDeg$_{Step-wise}$), with adjustments based on three consecutive pre-breakfast SMBG values (N=111). IDeg was administered using the FlexTouch® insulin pen (Novo Nordisk A/S, Bagsværd, Denmark), with once-weekly dose titration in both groups.

Results:

Glycosylated hemoglobin decreased from baseline to Week 26 in both groups (−1.09%, IDeg$_{Simple}$; −0.93%, IDeg$_{Step-wise}$). IDeg$_{Simple}$ was non-inferior to IDeg$_{Step-wise}$ in lowering HbA$_{1c}$ (estimated treatment difference [IDeg$_{Simple}$−IDeg$_{Step-wise}$]: −0.16%-points [−0.39; 0.07]$_{95\% \, CI}$). Fasting plasma glucose was reduced (−3.27 mmol/L, IDeg$_{Simple}$; −2.68 mmol/L, IDeg$_{Step-wise}$) with no significant difference between groups. Rates of confirmed hypoglycemia (1.60, IDeg$_{Simple}$; 1.17, IDeg$_{Step-wise}$ events/patient year of exposure [PYE]) and nocturnal confirmed hypoglycemia (0.21, IDeg$_{Simple}$; 0.10, IDeg$_{Step-wise}$ events/PYE) were low, with no significant differences between groups. Daily insulin dose after 26 weeks was 0.61 U/kg (IDeg$_{Simple}$) and 0.50 U/kg (IDeg$_{Step-wise}$). No significant difference in weight change was seen between groups by Week 26 (+1.6 kg, IDeg$_{Simple}$; +1.1 kg, IDeg$_{Step-wise}$), and there were no clinically relevant differences in adverse event profiles.

Conclusion

IDeg was effective and well tolerated using either the Simple or Step-wise titration algorithm. While selection of an algorithm must be based on individual patient characteristics and goals, the ability to attain good glycemic control using a simplified titration algorithm may enable patient empowerment through self-titration, improved convenience, and reduced costs.

INTRODUCTION

Numerous studies investigating the cost of self-measured blood glucose (SMBG) testing have found that it comprises a substantial portion of diabetes-related expenditures [15-18]. In a retrospective database analysis in the US that included more than 45,000 patients, testing accounted for 27% of diabetes care costs: total combined blood glucose testing and insulin-related costs were $2,850 USD/patient/year, with $772 USD/patient/year attributed to blood glucose testing alone [18]. In other countries, testing comprises an even higher percentage of diabetes care costs, (e.g., 40% in Canada [16, 17] and 42% in Germany [15]).

Insulin degludec (IDeg) is a new basal insulin (currently approved in Europe, Japan, Mexico and several other countries) with a flat, ultra-long action profile that may enable subjects to achieve glycosylated hemoglobin (HbA$_{1c}$) levels closer to glycemic target with fewer hypoglycemic episodes [19-21]. It was thus hypothesized that IDeg could be titrated once weekly based on a single pre-breakfast SMBG value, offering a simple, patient-focused titration algorithm that would encourage self-titration, enhancing patient empowerment as well as substantially reducing treatment costs by reducing the frequency of blood glucose measurements required for dose adjustments. In this study, after 26 weeks of treatment, we compared the efficacy and safety of two different self-titration algorithms for IDeg administered once daily (OD) plus metformin, in insulin-naïve subjects with type 2 diabetes: a "Simple" algorithm, in which 4 unit [U] dose adjustments were made based on a single pre-breakfast SMBG measurement was compared with a "Step-wise" algorithm, in which dose adjustments were made in increments of 2 U (Table 2) based on the lowest of three consecutive pre-breakfast SMBG readings. In both groups, IDeg was adjusted once weekly. The objective of this trial was to provide additional guidance on the use of IDeg in clinical practice by investigating whether good glycemic control could be attained with a more simplified titration schedule, involving fewer SMBG tests, than that previously employed during the IDeg Phase 3a development program.

Methods

The study was conducted according to the Declaration of Helsinki (2008) [22] and ICH Good Clinical Practice (1996) guidelines [23], with prior approval by appropriate ethics committees and patient consent obtained in writing prior to the start of any study-related activities. Eligible participants included insulin-naïve men or women ≥18 years of age, with type 2 diabetes, HbA$_{1c}$ 7.0-10.0% (inclusive), and body mass index (BMI) ≤45.0 kg/m$^2$, who were treated with ≥1000 mg/day metformin alone or in combination with one or two other oral antidiabetic medications (OADs) (including a sulfonylurea [SU] or glinide, dipeptidyl peptidase-4 [DPP-4] inhibitors, α-glucosidase inhibitors or thiazolidinediones [TZDs]), with unchanged dosing for ≥12 weeks prior to randomization. Participants were ineligible if they had used a glucagon-like-peptide-1 (GLP-1) receptor agonist within 12 weeks prior to randomization; had initiated or significantly changed treatment that could interfere with glucose metabolism; had significant disease other than type 2 diabetes; were pregnant or breastfeeding; or had recurrent severe hypoglycemia/hypoglycemia unawareness. Subjects could be withdrawn from the trial due to withdrawal of consent, not fulfilling inclusion/exclusion criteria (randomized in error), non-compliance, or at the discretion of the investigator due to a safety concern. Subjects who were withdrawn after randomization were not to be replaced. This trial is registered at clinicaltrials.gov: NCT01326026.

Study Design and Treatment

This was a multinational (conducted in the US, Spain, Finland, and Germany), Phase 3b, multi-center, two-armed, parallel group, open-label, randomized, treat-to-target study that compared the efficacy and safety of IDeg OD [IDeg 100 U/mL, FlexTouch® pen, Novo Nordisk A/S, Bagsværd, Denmark], adjusted using two different titration algorithms in combination with metformin. The trial consisted of a 26-week period; total study duration was approximately 28 weeks (including 1 week for screening and a 7-day follow-up period). After discontinuing all OADs other than metformin, subjects were randomized 1:1 by an interactive voice/web response system (IV/WRS) to IDeg$_{Simple}$ or IDeg$_{Step-wise}$ insulin self-titration algorithms, as defined below. Subjects were instructed to self-titrate in accordance with their respective algorithms and continue with their pre-trial metformin dose. At randomization, Week 4 and Week 12, subjects in both treatment arms received diet and exercise counselling by an HCP. The importance of maintaining a healthy diet and exercise plan was reinforced at each visit.

A Novo Nordisk A/S safety committee blinded to treatment performed on-going safety surveillance, but could request unblinding of the data to be performed by an independent ad hoc group, if needed. Blinded insulin titration surveillance was performed by Novo Nordisk A/S.

IDeg was administered OD at a starting dose of 10 U in both groups. Variation of injection time from day to day was permitted, as long as subjects maintained a minimum of 8 and a maximum of 40 hours between injections. Self-adjustment of IDeg dose was to be performed once weekly in both groups according to the algorithms outlined in Table 2. In the IDeg$_{Simple}$ arm, dose adjustment was based on a single pre-breakfast SMBG measurement. In the IDeg$_{Step-wise}$ arm, dose adjustment was based on the lowest of 3 consecutive days' pre-breakfast SMBG measure.

Efficacy and Safety Assessments

HbA$_{1c}$ was analyzed using a Bio-Rad high-performance liquid chromatography method at Visits 1 (screening), 2 (randomization), 14 (Week 12) and 28 (Week 26). Fasting plasma glucose (FPG) blood samples were assayed using a hexokinase-UV method at Visits 2, 14 and 28. At the first visit, subjects were provided with a glucose meter for SMBG measurement and instructions for use; blood glucose was measured with test strips calibrated to plasma glucose to obtain PG-equivalent values presented in this report. Subjects performed SMBG measurements before breakfast weekly after randomization and also performed an 8-point SMBG profile prior to Visits 2, 14 and 28.

Adverse events (AEs) and hypoglycemic episodes were documented throughout the study, with confirmed hypoglycemia defined as episodes of severe hypoglycemia (requiring assistance from another person) and episodes with PG value <3.1 mmol/L (56 mg/dL). Nocturnal confirmed hypoglycemic episodes were those occurring between 00:01 h and 05:59 h (inclusive). Laboratory safety variables, insulin dose and body weight were recorded at pre-specified intervals. Two patient-reported outcome (PRO) questionnaires (Device-Specific questionnaires I and II) were self-completed at Visits 14 and 28 to assess subject satisfaction with the FlexTouch® pen as an additional trial endpoint. The PRO questionnaire utilized here to assess patient satisfaction with FlexTouch® had previously been used in other trials to assess satisfaction with the FlexPen® device (Novo Nordisk A/S, Bagsværd, Denmark) [24, 25].

Statistical Methods

With 218 subjects, there was 85% power to demonstrate non-inferiority at 0.4% in evaluation of the per-protocol (PP) analysis set (defined as all subjects without major protocol violations who were exposed to treatment for >12 weeks and who had a valid assessment necessary for deriving the primary endpoint), accounting for an anticipated total of 15% that would not be included in the PP analysis set. Sample size was determined using a t-statistic under the assumption of a one-sided test of size 2.5% and a zero mean treatment difference. Data were reported using a 95% confidence interval (CI) and P-values for 1-sided testing for non-inferiority at alpha=0.025 for the primary analysis, and 2-sided testing with alpha=0.050 for all other analyses. Statistical analyses of all efficacy and patient-reported outcome endpoints were based on the full analysis set (FAS), defined as all randomized subjects, and followed the intention-to-treat (ITT) principle unless otherwise noted. The robustness of the results for change in $HbA_{1c}$ was explored by an additional analysis of the PP analysis set. Further, robustness was explored by an additional analysis of the set of all subjects who completed the trial and by using a simple model based on the FAS with only treatment and baseline $HbA_{1c}$ as covariates. Safety endpoints were summarized based on the safety analysis set (SAS), defined as all subjects who received at least one dose of IDeg, and analyzed based on the FAS.

Change from baseline in $HbA_{1c}$ after 26 weeks was analyzed using an analysis of variance (ANOVA) method with treatment, region, sex and antidiabetic therapy at screening as fixed factors, and age and baseline $HbA_{1c}$ as covariates. Non-inferiority was considered confirmed if the upper bound of the two-sided 95% CI for the treatment difference ($IDeg_{Simple}$–$IDeg_{Step-wise}$) for the mean change in $HbA_{1c}$ was ≤0.4%. Change in FPG and change in body weight were analyzed using an ANOVA model similar to that used for the primary analysis, but with the relevant baseline value as covariate for each measure. Responder endpoints (proportion of subjects who achieved target $HbA_{1c}$ and proportion who achieved target without hypoglycemia) were analyzed using a logistic regression model with the same factors and covariates as those used for the primary analysis. An 8-point SMBG profile included measurements before and 90 minutes after the start of breakfast, lunch and main evening meal, prior to bedtime, and before breakfast the following day. A mixed effect model including treatment, time, interaction between treatment and time, antidiabetic therapy at screening, sex and region as fixed factors, age as covariate and subject as random effect was fitted to the 8-point SMBG profile data. From this model, mean profile by treatment and relevant treatment differences were estimated and explored. Treatment-emergent AEs, hypoglycaemic episodes, laboratory parameters, physical examination, electrocardiogram (ECG), fundoscopy/fundus-photography, vital signs, PRO (Device-Specific questionnaires I and II) and insulin dose were summarized with descriptive statistics. The numbers of treatment-emergent confirmed and nocturnal confirmed hypoglycaemic episodes were analyzed using a negative binomial regression model with a log-link function and the logarithm of the time period for which a hypoglycaemic episode was considered treatment emergent as offset; the model included treatment, sex, region and antidiabetic treatment at screening as fixed factors and age as covariate.

Results

Demographics and Baseline

Participants were allocated 1:1 to the $IDeg_{Simple}$ (N=111) and $IDeg_{Step-wise}$ (N=111) arms (Table 3). Of 222 randomized participants, 221 (99.5%) received trial drug. Treatment arms were well matched at baseline, with the exception of a slightly higher mean body weight and more female subjects in the $IDeg_{Simple}$ arm. Subjects in the $IDeg_{Step-wise}$ arm had a slightly longer mean duration of diabetes. The majority of participants in both groups were taking two OADs at baseline (61/111 subjects, 55%); ~21% in each group were taking >2 OADs, and ~24% in each group were taking 1 OAD. The most common pre-trial OAD other than metformin was a SU. Most (89.2% [99/111], $IDeg_{Simple}$; 88.3% [98/111], $IDeg_{Step-wise}$) subjects completed the trial. Four $IDeg_{Simple}$ and three $IDeg_{Step-wise}$ subjects were withdrawn due to AEs; five $IDeg_{Simple}$ and seven $IDeg_{Step-wise}$ subjects were withdrawn due to meeting withdrawal criteria; and three subjects in each group were withdrawn due to reasons classified as "other" (FIG. 1).

$HbA_{1c}$ decreased from baseline to Week 26 in both groups; −1.09% with $IDeg_{Simple}$, to 7.0%, and −0.93% with $IDeg_{Step-wise}$, to 7.2% (FIG. 2a). $IDeg_{Simple}$ was non-inferior to $IDeg_{Step-wise}$ in lowering $HbA_{1c}$, as the upper limit of the 95% CI for the estimated treatment difference (ETD) was <0.4%: ETD ($IDeg_{Simple}$–$IDeg_{Step-wise}$)−0.16%-points [−0.39; 0.07]$_{95\%\ CI}$. Analyses to measure robustness of results were consistent with FAS results. Significantly more $IDeg_{Simple}$ (56.8% [63/111]) than $IDeg_{Step-wise}$ (41.4% [46/111]) subjects achieved $HbA_{1c}$<7.0% at end-of-trial; estimated odds ratio ($IDeg_{Simple}$/$IDeg_{Step-wise}$): 1.93 [1.04; 3.55] $_{95\%\ CI}$ (P=0.0356). There was no significant difference in the proportion of patients achieving $HbA_{1c}$<7% without confirmed hypoglycemia (40.6% [43/106] $IDeg_{Simple}$; 34.6% [36/104] $IDeg_{Step-wise}$); estimated odds ratio ($IDeg_{Simple}$/$IDeg_{Step-wise}$): 1.26 [0.69; 2.29]$_{95\%\ CI}$.

FPG decreased from baseline to Week 26 by 3.27 mmol/L with $IDeg_{Simple}$, to 6.1 mmol/L, and by 2.68 mmol/L with $IDeg_{Step-wise}$, to 6.8 mmol/L (FIG. 2b). No significant difference was seen between groups: ETD ($IDeg_{Simple}$–$IDeg_{Step-wise}$): −0.57 mmol/l [−1.30; 0.17]$_{95\%\ CI}$. The most pronounced decline in FPG occurred during the first 12 weeks. No difference between groups in 8-point SMBG profiles was seen at any of the eight measured time points at baseline or at end-of-trial (FIG. 2c).

Rates of confirmed hypoglycemia were low, at 1.60 and 1.17 events per patient year of exposure (PYE) with IDeg$_{Simple}$ and IDeg$_{Step\text{-}wise}$, respectively (FIG. 3a), with no significant difference between groups (P=0.4273). One severe hypoglycemic episode occurred in the IDeg$_{Simple}$ arm 5 days after the last treatment with IDeg. Observed rates of nocturnal confirmed hypoglycemia were very low at 0.21 (IDeg$_{Simple}$) and 0.10 (IDeg$_{Step\text{-}wise}$) events per PYE (FIG. 3b), with no significant difference between groups (P=0.2047).

The observed daily insulin dose after 26 weeks was 62 U (0.61 U/kg) in the IDeg$_{Simple}$ arm and 48 U (0.50 U/kg) in the IDeg$_{Step\text{-}wise}$ arm. Up to Week 4, mean doses were similar, after which the mean dose in the Simple arm was higher. The increase in IDeg dose per week began to level off in the IDeg$_{Step\text{-}wise}$ arm at Week 14. Although subjects were permitted to adjust their dose by increments larger than 4 U in the IDeg$_{Step\text{-}wise}$ arm, the mean weekly incremental increase was ≤3 U.

Mean baseline body weight was higher in the IDeg$_{Simple}$ arm (95.7 kg) than in the IDeg$_{Step\text{-}wise}$ arm (91.3 kg). Modest increases in weight were observed from baseline to Week 26 in both groups: IDeg$_{Simple}$: (+1.6 kg, to mean weight 97.3 kg at Week 26), IDeg$_{Step\text{-}wise}$ (+1.1 kg, to mean weight 92.4 kg at Week 26), with no statistically significant difference in weight change: ETD (IDeg$_{Simple}$–IDeg$_{Step\text{-}wise}$) 0.46 kg [−0.35; 1.26]$_{95\%\ CI}$. There were no clinically relevant differences from baseline to end-of-trial or between treatment arms for vital signs, ECG, fundoscopy, physical examination or laboratory parameters (data not shown).

No safety concerns were raised during this trial. Refer to Table 4 for an overview of the rates of AEs and serious AEs (SAEs) reported. AEs and SAEs were distributed similarly between groups. Most AEs were of mild or moderate severity and the rates of AEs classified as possibly or probably related to trial product by the investigator were low (10.0% [IDeg$_{Simple}$]; 7.2% [IDeg$_{Step\text{-}wise}$]). Injection-site reactions (ISRs) were reported by 2.7% (3 subjects with 3 events) of IDeg$_{Simple}$ and 4.5% (5 subjects with 16 events) of IDeg$_{Step\text{-}wise}$ subjects; one subject reported 9 of the 16 total events in the IDeg$_{Step\text{-}wise}$ arm, and reported "pain" as the ninth ISR. No SAEs were reported in ≥5% of subjects and none were considered by the investigator to be related to trial product. One death occurred in this study 154 days after starting trial drug in an IDeg$_{Step\text{-}wise}$-treated participant, due to liver metastasis (the primary cancer was reported as probable small cell lung carcinoma). The event was considered by the investigator to be unlikely related to treatment. One other SAE neoplasm event (astrocytoma [IDeg$_{Simple}$]), and three events adjudicated as major adverse cardiovascular events (coronary artery stenosis [IDeg$_{Simple}$], acute myocardial infarction [IDeg$_{Simple}$] and coronary artery occlusion [IDeg$_{Step\text{-}wise}$]) occurred, all of which were considered by the investigator to be unlikely related to treatment. No IDeg-related medication errors were reported.

In the Device-Specific questionnaires, more than 90% of subjects at Week 12 and Week 26 indicated the highest levels of satisfaction (response category 1 or 2) with the Flex-Touch® device. At 26 weeks, 98% of subjects reported no problems using FlexTouch® and 100% of subjects indicated that they would recommend the pen. Refer to Table 5 for additional details on the results of the questionnaires (Table 5 contains a subset of the total questions surveyed in this trial).

DISCUSSION

Both the Simple and Step-wise titration algorithms were effective, well-tolerated methods of achieving glycemic targets with IDeg, thereby demonstrating that titration based on either a single weekly SMBG measurement with the Simple algorithm, or three measurements with the Step-wise algorithm, provide suitable options for patients with type 2 diabetes. Titration using the Simple algorithm was shown to be non-inferior to titration using the Step-wise algorithm in terms of improving HbA$_{1c}$ and both methods resulted in a similar FPG reduction. End-of-trial HbA$_{1c}$ and change from baseline in HbA$_{1c}$ in both treatment arms were similar to values seen with IDeg in similar previous Phase 3a (BE-GIN™) trials in people with type 2 diabetes. These previous trials all demonstrated similar efficacy between IDeg and insulin glargine as demonstrated by non-inferiority in terms of change in HbA$_{1c}$, were 26 or 52 weeks in duration, enrolled insulin-naïve subjects (except for the BEGIN™ Basal-Bolus T2 study in which insulin aspart was dosed with meals [26]) and employed a titration algorithm similar to the Step-wise algorithm, but with weekly titration based on the mean of 3 consecutive days' pre-breakfast SMBG measurements [26-29].

IDeg dose was increased more quickly in the IDeg Simple arm, whereas insulin dose escalation was reduced earlier in the IDeg$_{Step\text{-}wise}$ arm, reflecting a point of differentiation between the algorithms: as pre-breakfast SMBG values approached target, the Step-wise algorithm permitted a smaller dose increase of 2 U versus the recommended 4 U increase in the IDeg$_{Simple}$ arm. Insulin dose was higher at end-of-trial in the IDeg$_{Simple}$ arm than in the IDeg$_{Step\text{-}wise}$ arm, which may account for the non-significant differences seen between groups in FPG and hypoglycemia. FPG values were numerically lower over longer periods of time in the IDeg Simple arm; this may have influenced the observed rates of hypoglycemia, as these rates represented the entire treatment period. The small and non-significant difference in FPG between the IDeg$_{Simple}$ and IDeg$_{Step\text{-}wise}$ arms likely also contributed to the difference between groups in achieving the HbA$_{1c}$ target of <7%. It is important to note that there was no significant difference between groups in the achievement of the HbA$_{1c}$ target without confirmed hypoglycemia.

The Simple algorithm offers an easy and patient-friendly way to titrate IDeg; additionally, the capacity to adjust IDeg doses with a 4 U increase or decrease, based on a single weekly SMBG value, may substantially reduce the financial and time burden and inconvenience of titration measurements. Incidence rates of hypoglycemic episodes were very low, with no significant difference between the Simple and Step-wise arms. As shown in FIG. 3a and FIG. 3b, respectively, end-of-trial confirmed and nocturnal confirmed hypoglycemia rates seen here were comparable to or lower than rates with IDeg administered OD in the BEGIN™ trials in people with type 2 diabetes; rates that, in turn, were lower than or similar to those seen with comparator insulin glargine in other studies of the insulin degludec development program. [26-29]

Subjects in both treatment arms adhered closely to their respective algorithms. The ability and willingness of patients to adhere to a given treatment regimen is an important component in the success of insulin therapy. Surveys of physicians and patients have identified "too busy" and "complicated regimen" as prominent reasons why patients miss or omit insulin injections; 17% of patients report difficulty in adjusting insulin doses, and 60% of patients feel that their insulin regimens can be restrictive [10-11]. There is evidence to support the premise that if patients are more comfortable with, and accepting of, their dosing regimen, they may be more willing to continue treatment in the long-term [12-14]. Furthermore, patient empowerment may be enhanced by a titration algorithm that facilitates self-adjustment of basal insulin and better adherence to treatment regimens, potentially leading to improved health outcomes. In the Predictable Results and Experience in Diabetes through Intensification and Control to Target: An International Variability Evaluation (PREDICTIVE™) 303 study with insulin detemir, a simplified self-adjusted dosing algorithm in which patients tested SMBG daily and adjusted their dose every 3 days based on the mean of the previous 3 days' values was shown to significantly lower $HbA_{1c}$ versus standard-of-care, physician-driven adjustments over a period of 6 months [4], thus, providing further evidence that a simple self-titration method can help subjects achieve glycemic targets. Additionally, patient acceptance of the insulin delivery device used to administer doses is a factor that appears to influence adherence and persistence with a given treatment regimen [30-33]. It has been reported that positive perceptions of convenience also play an important role in the persistence of pen use [34]. In this trial, high levels of satisfaction with the FlexTouch® insulin pen device were reported in both treatment arms and all subjects indicated that they would recommend the pen to others. This reflects the experiences of patients in other IDeg trials using the same device, in which the majority of patients reported ease in using the pen and a high degree of satisfaction with FlexTouch® [35-39].

CONCLUSION

Achieving good glycemic control in patients with type 2 diabetes is an important way to prevent or limit diabetes complications, and control the costs of intensified healthcare utilization stemming from these complications. SMBG is an integral part of effective diabetes management; however, glucose meters, test strips, lancets, and alcohol wipes are consumable items that comprise on-going expenses, with test strips identified as a major driver of these costs [15-18]. New medications and treatment regimens that permit a reduction in the number of SMBG measurements without compromising clinical outcomes would likely benefit all basal insulin-treated patients who may find current algorithms confusing or cumbersome. These patients may be more likely to adhere to a simpler regimen that ultimately results in improved health outcomes and lower healthcare costs. This trial demonstrates that IDeg, titrated using either the Simple or Step-wise algorithm, leads to good glycemic control and is well tolerated, offering individualized titration regimens that best meet patient needs.

TABLE 2

Comparison of BEGIN™ Once Simple titration algorithms

| Pre-breakfast SMBG | | Dose adjustment IDeg Simple[a] | Dose adjustment IDeg Step-wise[b] |
|---|---|---|---|
| mmol/L | mg/dL | U | U |
| <3.1 | <56 | -4 | -4 |
| 3.1-3.9 | 56-70 | | -2 |
| 4.0-5.0 | 71-90 | 0 | 0 |
| 5.1-7.0 | 91-126 | +4 | +2 |
| 7.1-8.0 | 127-144 | | +4 |
| 8.1-9.0 | 145-162 | | +6 |
| >9.0 | >162 | | +8 |

[a] Based on a single measurement on the day of titration;
[b] Based on the lowest of 3 consecutive days' measurements.
IDeg insulin degludec;
SMBG self-measured blood glucose

TABLE 3

Demographics and baseline characteristics BEGIN™ Once Simple

| Characteristic | IDeg Simple | IDeg Step-wise |
|---|---|---|
| Participants in the full analysis set, n | 111 | 111 |
| Participants in the safety analysis set, n | 110 | 111 |
| Female/Male, n (%) | 43 (38.7)/68 (61.3) | 36 (32.4)/75 (67.6) |
| Ethnic Group: White/Black/Asian, American Indian or Alaska Native/Other, n (%) | 99 (89.2)/8 (7.2)/3 (2.7)/1 (0.9) | 97 (87.4)/9 (8.1)/2 (1.8)/3 (2.7) |
| Age (years) | 59.4 (±9.5) | 58.5 (±11.1) |
| Body weight (kg) | 95.7 (±18.9) | 91.3 (±18.2) |
| Body mass index (kg/m$^2$) | 33.4 (±5.8) | 31.5 (±5.2) |
| Duration of diabetes (years) | 8.9 (±5.5) | 9.6 (±7.2) |
| $HbA_{1c}$, (%) | 8.1 (±0.9) | 8.2 (±0.9) |
| FPG (mmol/L) | 9.3 (±2.6) | 9.4 (±2.8) |
| (mg/dL) | 167.4 (±46.8) | 169.2 (±50.4) |
| OAD treatment at screening, n (%) | | |
| 1 OAD | 27 (24.3%) | 26 (23.4%) |
| Met | 27 (24.3%) | 26 (23.4%) |
| 2 OADs | 61 (55.0%) | 61 (55.0%) |
| Met + DPP-4I | 16 (14.4%) | 13 (11.7%) |
| Met + Glinide | 1 (0.9%) | 2 (1.8%) |
| Met + SU | 40 (36.0%) | 42 (37.8%) |
| Met + TZD | 4 (3.6%) | 4 (3.6%) |
| 3 OADs | 23 (20.7%) | 24 (21.6%) |
| α-glu inhib + Met + DPP-4I | 1 (0.9%) | — |
| Met + DPP-4I + Glinide | 1 (0.9%) | 3 (2.7%) |
| Met + DPP-4I + SU | 13 (11.7%) | 8 (7.2%) |
| Met + DPP-4I + TZD | — | 2 (1.8%) |
| Met + SU + TZD | 8 (7.2%) | 11 (9.9%) |

Data are presented as number (%) or mean (SD).

OAD oral antidiabetic drug, Met metformin, SU sulfonylurea, TZD thiazolidinedione, DPP-4I dipeptidyl peptidase 4 inhibitor, a-glu inhib, alpha-glucosidase inhibitor, FPG fasting plasma glucose, IDeg insulin degludec, SD standard deviation, $HbA_{1c}$ glycosylated hemoglobin.

TABLE 4

Summary of adverse events BEGIN™ Once Simple

| | IDeg Simple N = 110 | | | | IDeg Step-wise N = 111 | | | |
|---|---|---|---|---|---|---|---|---|
| | N | % | E | R | N | % | E | R |
| AEs | 66 | 60.0 | 181 | 346 | 69 | 62.2 | 197 | 379 |
| AEs occurring with a frequency ≥ 5% | 17 | 15.5 | 18 | 34 | 14 | 12.6 | 22 | 42 |

TABLE 4-continued

Summary of adverse events BEGIN ™ Once Simple

| | IDeg Simple N = 110 | | | | IDeg Step-wise N = 111 | | | |
|---|---|---|---|---|---|---|---|---|
| | N | % | E | R | N | % | E | R |
| Headache | 8 | 7.3 | 8 | 15 | 8 | 7.2 | 14 | 27 |
| Nasopharyngitis | 10 | 9.1 | 10 | 19 | 7 | 6.3 | 8 | 15 |
| SAEs | 5 | 4.5 | 8 | 15 | 7 | 6.3 | 8 | 15 |

Treatment-emergent events occurring after first exposure and no later than 7 days after last exposure. Safety analysis set. n number of patients with events, % proportion of patients with events, E number of events, R number of events per 100 patient-years.

TABLE 5

Device-specific questionnaire responses BEGIN ™ Once Simple

| | Positive response (Category 1 or 2) N (%) | Neutral or Negative response (Category 3, 4 or 5) N (%) |
|---|---|---|
| 1. How easy or difficult do you find it to hold the pen stable when injecting? | | |
| Wk 12 | 195 (94.7) | 11 (5.3) |
| Wk 26 | 202 (98.5) | 3 (1.5) |
| 2. How easy or difficult is it to push down the injection button? | | |
| Wk 12 | 197 (95.2) | 9 (4.8) |
| Wk 26 | 202 (98.0) | 4 (2.0) |
| 3. How easy or difficult is it to turn the dose selector when choosing the right dose? | | |
| Wk 12 | 199 (97.5) | 5 (2.5) |
| Wk 26 | 196 (96.1) | 8 (3.9) |
| 4. How easy or difficult is it to know if the push button has been pushed down completely? | | |
| Wk 12 | 192 (93.2) | 14 (6.8) |
| Wk 26 | 195 (95.2) | 9 (4.8) |
| 5. How easy or difficult is it to see the dose scale when injecting? | | |
| Wk 12 | 176 (85.5) | 30 (14.5) |
| Wk 26 | 174 (85.2) | 30 (14.8) |
| 6. How easy or difficult was it to learn how to use this pen? | | |
| Wk 12 | 200 (98.0) | 4 (2.0) |
| Wk 26 | 199 (98.5) | 3 (1.5) |
| 7. How easy or difficult is it to inject your usual insulin dose? | | |
| Wk 12 | 193 (94.6) | 11 (5.4) |
| Wk 26 | 196 (97.0) | 6 (3.0) |
| 8. How easy or difficult is it to reach the dose button when injecting your insulin dose? | | |
| Wk 12 | 193 (94.6) | 11 (5.4) |
| Wk 26 | 195 (96.5) | 7 (3.5) |
| 9. Overall, how confident are you in your management of daily insulin injection using this pen? | | |
| Wk 12 | 191 (93.1) | 14 (6.9) |
| Wk 26 | 196 (96.1) | 8 (3.9) |
| 10. Overall, how confident are you in controlling your blood sugar level using this pen? | | |
| Wk 12 | 167 (81.8) | 37 (18.2) |
| Wk 26 | 178 (88.6) | 23 (11.4) |

Data is based on FAS and summarized independent of treatment arm. % Percentage based on ITT population who answered the questionnaire. Categories for questions 1-8: 1=Very easy, 2=Somewhat easy, 3=Neither easy nor difficult, 4=Somewhat difficult, 5=Very difficultategories for questions 9-10: 1=Very, 2=Quite, 3=Somewhat, 4=Not very, 5=Not at all (confident). N Number, Wk Week, ITT intention to treat.

| | Positive response N (%) | Negative response N (%) |
|---|---|---|
| 1. Did you have any problems using the pen? | | |
| Wk 12 | 205 (100.0) | N/A |
| Wk 26 | 201 (100.0) | N/A |
| 2. Would you recommend the pen? | | |
| Wk 12 | 202 (100.0) | N/A |
| Wk 26 | 200 (100.0) | N/A |

Data is based on FAS and summarized independent of treatment arm. Categories for questions 1-2: 1=No, 2=Yes. N Number, Wk Week, NA not applicable, ITT intention to treat.

Example 2: Use of Glucose Measurements to Determine Whether a Fasting Event is Insulin Regimen Adherent In some embodiments, the first data set 224 comprising a plurality of glucose measurements is obtained. In some embodiments the glucose measurements are obtain autonomously, for instance by a continuous glucose monitor 102. In this example, in addition to the autonomous glucose measurements, insulin administration events are obtained in the form of insulin medicament records 232 from one or more insulin pens 104 used by the subject to apply the prescribed insulin regimen 212. These insulin medicament records 232 may be in any format, and in fact may be spread across multiple files or data structures. As such, in some embodiments, the instant disclosure leverages the recent advances of insulin administration pens, which have become "smart" in the sense that they can remember the timing and the amount of insulin medicament administered in the past. One example of such an insulin pen 104 is the NovoPen 5. Such pens assist patients in logging doses and prevent double dosing. It is contemplated that insulin pens will be able to send and receive insulin medicament dose volume and timing, thus allowing the integration of continuous glucose monitors 102, insulin pens 104 and the algorithms of the present disclosure. As such, insulin medicament records 232 from one or more insulin pens 104 is contemplated, including the wireless acquisition of such data from the one or more insulin pens 104.

In some embodiments, each insulin medicament record 232 comprises: (i) a respective insulin medicament injection event 234 including an amount of insulin medicament injected into the subject using a respective insulin pen in the one or more insulin pens and (ii) a corresponding electronic timestamp 236 that is automatically generated by the respective insulin pen 104 upon occurrence of the respective insulin medicament injection event.

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

The present invention can be implemented as a computer program product that comprises a computer program mechanism embedded in a non-transitory computer readable storage medium. For instance, the computer program product could contain the program modules shown in any combination of FIGS. 1 and 2 and/or described in FIG. 5. These program modules can be stored on a CD-ROM, DVD, magnetic disk storage product, USB key, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended embodiments, along with the full scope of equivalents to which such embodiments are entitled.

The invention claimed is:

1. A system for providing a long-acting or ultra-long-acting insulin dose guidance recommendation for a subject to treat diabetes mellitus, wherein the system comprises one or more processors and a memory, the memory comprising:
instructions that, when executed by the one or more processors, perform a method responsive to receiving a dose guidance request (DGR) comprising determining whether or not to autonomously adjust a dosage recommendation based on the DGR, said instructions comprising:
(A) obtaining a first data structure that comprises at least:
(i) an upper limit target glucose range (UTR) of the subject, and (ii) a lower limit target glucose range (LTR) of the subject;
(B) obtaining a second data structure, comprising:
(i) a current dose guidance baseline (DGB), and (ii) a corresponding DGB timestamp representing when the DGB was made,
wherein the current DGB corresponds to:
(a) a most recent adjustment day dose recommendation (ADDR), and/or
(b) a starting basal dose (SBD);
(C) obtaining a first data set, comprising a plurality of glucose measurements of the subject taken over a time course and thereby establishing a blood glucose history (BGH), each respective glucose measurement in the plurality of glucose measurements comprising:
(i) a blood glucose (BG) level, and
(ii) a corresponding glucose timestamp (BGT) representing when in the time course the respective glucose measurement was made;
(D) obtaining a second data set, comprising a basal insulin injection history (IH) of the subject, wherein the injection history comprises a plurality of injections during all or a portion of the time course and, for each respective injection in the plurality of injections comprising:
(i) a corresponding injection amount (IA),
(ii) an injection timestamp (IT) representing when in the time course the respective injection occurred;
(E) obtaining a third data structure, comprising:
an injection data refresh timestamp (IDR) of the subject,;
(F) evaluating at least the first data structure, the second data structure, the third data structure, the first data set, and the second data set and thereby determining whether they collectively contain a set of evaluation information comprising at least:
(i) the glucose upper and lower target range levels of the subject,
(ii) the current dose guidance baseline and the corresponding timestamp,
(iii) the injection history refresh timestamp for the subject,
(iv) the plurality of glucose measurements of the subject taken over the time course, and
(v) the injection history of the subject;
wherein:
when a determination is made that the at least first data structure, second data structure, third data structure, first data set, and second data set collectively do contain the set of evaluation information, and when the dose guidance request was received within a given time limit from the injection data refresh timestamp, then the method further comprises providing the long-acting or ultra-long-acting insulin ADDR, the recommendation being calculated based on data from the first data structure, the second data structure, the first data set, and second data set, and further comprises autonomously adjusting a dosage recommendation configured to be provided to a patient based on the ADDR;
when a determination is made that the first data structure, the second data structure, the third data structure, the first data set, and the second data set fail to collectively contain the set of evaluation information, or when the dose guidance request was received after the given time limit from the injection history refresh timestamp, then no long-acting or ultra-long-acting insulin ADDR is provided and the dosage recommendation configured to be provided to the patient is not autonomously adjusted.

2. The system of claim 1, wherein the long-acting or ultra-long-acting insulin, has a side chain attached to the α-amino group of the N-terminal amino acid residue of the B chain or to the ε-amino group of the Lys residue present in the B chain of the parent insulin, the side chain being of the general formula:

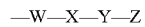

—W—X—Y—Z wherein W is:
(i) an α-amino acid residue having a carboxylic acid group in the side chain which residue forms, with one of its carboxylic acid groups, an amide group together with the α-amino group of the N-terminal amino acid residue of the B chain or together with the ε-amino group of a Lys residue present in the B chain of the parent insulin;
(ii) a chain composed of two, three or four a-amino acid residues linked together via amide bonds, which chain—via an amide bond—is linked to the a-amino group of the N-terminal amino acid residue of the B chain or to the ε-amino group of a Lys residue present in the B chain of the parent insulin, the amino acid residues of W being selected from the group of amino acid residues having a neutral side chain and amino acid residues having a carboxylic acid group in the side chain so that W has at least one amino acid residue which has a carboxylic acid group in the side chain; or
(iii) a covalent bond from X to the a-amino group of the N-terminal amino acid residue of the B chain or to the ε-amino group of a Lys residue present in the B chain of the parent insulin;
wherein X is:

—CO—; (i)

—COCH(COOH)CO—; (ii)

—CON(CH$_2$COOH)CH$_2$CO—; (iii)

—CON(CH$_2$COOH)CH$_2$CON(CH$_2$COOH)CH—CO—; (iv)

—CON(CH$_2$CH$_2$COOH)CH$_2$CH$_2$CO—; (v)

—CON(CH$_2$CH$_2$COOH)CH$_2$CH$_2$CON(CH$_2$CH$_2$COOH)CH$_2$CH$_2$CO—; (vi)

—CONHCH(COOH)(CH$_2$)$_4$NHCO—; (vii)

—CON(CH$_2$CH$_2$COOH)CH$_2$CO—; or (viii)

—CON(CH$_2$COOH)CH$_2$CH$_2$CO; (ix)

provided that:
(a) when W is an amino acid residue or a chain of amino acid residues, via a bond from the underscored carbonyl carbon forms an amide bond with an amino group in W; or
(b) when W is a covalent bond, via a bond from the underscored carbonyl carbon forms an amide bond with the N-terminal a-amino group in the B chain or with the ε-amino group of a Lys residue present in the B chain of the parent insulin;
wherein Y is:
(i) a—(CH2)m- where m is an integer in the range of 6 to 32;
(ii) a divalent hydrocarbon chain comprising 1, 2 or 3 —CH=CH— groups and a number of —CH2- groups sufficient to give a total number of carbon atoms in the chain in the range of 10 to 32; or
(iii) a divalent hydrocarbon chain of the formula —(CH2)vC6H(CH2)w- wherein v and w are integers or one of them is zero so that the sum of v and w is in the range of 6 to 30;
wherein Z is:

—COOH; (i)

—CO-Asp; (ii)

—CO-Glu; (iii)

—CO-Gly; (iv)

—CO-Sar; (v)

—CH(COOH)2; (vi)

—N(CH2COOH)2; (vii)

—SO3H; or (viii)

—PO3H; (ix)

and any Zn2+ complexes thereof, provided that when W is a covalent bond and X is —CO—, then Z is different from —COOH.

3. The system of claim 1, wherein the long-acting or ultra-long-acting insulin is LysB29(Nε-hexadecandioyl-γ-Glu) des (B30) human insulin, which is insulin degludec.

4. The system of claim 1, wherein the long-acting insulin or ultra-long-acting insulin is selected from the group consisting of:
a) neutral protamine hagedorn insulin which is NPH insulin;
b) Lente Insulin;
c) Ultralente Insulin;
d) Glargine Insulin;
e) Detemir Insulin;
f) Hypurin Bovine Lente; and
g) Hypurin Bovine PZI.

5. The system of claim 1, wherein the long-acting or ultra-long-acting insulin is insulin degludec, and the long-acting or ultra-long-acting insulin is administered, concurrently or consecutively, with liraglutide.

6. The system of claim 1, wherein the time course comprises a current day and the past four days.

7. The system of claim 1, wherein the time course comprises the current day and between one and ten of the immediately preceding past days.

8. The system of claim 1, wherein the method further comprises updating the last injection data refresh within the immediately preceding 30 seconds or less, the immediately preceding 1 minute or less, or the immediately preceding 5 minutes or less.

9. The system of claim 1, wherein the method further comprises updating the dose guidance recommendation for the subject, unless the injection history of the subject comprises one or more injections of the subject that have injection timestamps within the current day.

10. The system of claim 1, wherein the method further comprises updating the dose guidance recommendation for the subject when at least one injection occurred within the current day and no injections occurred in the immediately preceding one day in the injection history time course.

11. The system of claim 1, wherein the method further comprises combining any injections in the injection history that have timestamps within a five-minute period in the time course into one injection.

12. The system of claim 1, wherein the method further comprises calculating a reconstructed blood glucose history of the subject when the blood glucose history time course contains a gap, and wherein the reconstructed blood glucose history is calculated based on the blood glucose history of each calendar day.

13. The system of claim 12, wherein the method further comprises performing a quality check of the reconstructed blood glucose history data, and wherein when the data quality check fails, then the dose guidance recommendation is not updated.

14. The system of claim 1, wherein the method further comprises providing a re-recommendation of the dose guidance recommendation until:
  (i) one or more injections with an injection amount equivalent to the dose guidance baseline have occurred,
  (ii) one or more injections have occurred since the dose guidance baseline and when one or more injections have occurred over the current day and the past two or three or four days, and
  (iii) one or more does events with an injection amount greater than or equal to the dose guidance baseline have occurred.

15. The system of claim 12, wherein the method further comprises selecting the dose guidance baseline from the set of parameters comprising at least the starting basal dose and the most recent adjustment day dose recommendation, and wherein the selected parameter has the timestamp closest to the current time.

16. The system of claim 15, wherein the method further comprises calculating a daily titration glucose level and an overall titration glucose level, wherein:
  (i) the daily titration glucose level for each calendar day is calculated by selecting the lowest average of reconstructed blood glucose history data for any predetermined first time period within the blood glucose history time course and excluding any reconstructed blood glucose history data with a timestamp older than the timestamp of the dose guidance baseline:
    when there are gaps larger than a predetermined second time period in the blood glucose history time course, then no daily titration glucose level is calculated,
    when there are gaps in the blood glucose history time course and these gaps are at least the predetermined second time period in length and less than a predetermined third time period in length within any calendar day in the blood glucose history time course, then the daily titration glucose level averaging omits any predetermined first time period containing gaps when averaging the reconstructed blood glucose history data, and
    when any calendar day in the blood glucose history time course contains gaps longer than the predetermined third time period or when more than a predetermined number of blood glucose measurements are absent, then no daily titration glucose level is calculated; and
  (ii) the overall titration glucose level is calculated by taking the average of the daily titration glucose levels, and wherein when no overall titration glucose level can be determined, then the dose guidance recommendation is not updated.

17. The system of claim 16, wherein the predetermined first time period is between 15 minutes and 120 minutes.

18. The system of claim 16, wherein the predetermined second time period is between 10 minutes and 40 minutes.

19. The system of claim 16, wherein the predetermined third time period is between 1 hour and 15 hours.

20. The system of claim 16, wherein the predetermined number of blood glucose measurements is between 20 and 100.

21. The system of claim 16, wherein the method further comprises:
  responsive to receiving a request for an updated adjustment day dose recommendation, performing a new recommendation procedure to determine the injection amount for the updated adjustment day dose recommendation, wherein the updated adjustment day dose recommendation function is based upon at least a titration glucose level and a max basal limit.

22. The system of claim 21, wherein the titration glucose level comprises one of (i), (ii), or (iii):
  (i) the overall titration glucose level is greater than the upper limit target glucose range,
  (ii) the overall titration glucose level is greater than or equal to the lower target glucose range and the overall titration glucose level is less than or equal to the upper limit target glucose range, and
  (iii) the daily titration glucose level is less than the lower target glucose range.

23. The system of claim 22, wherein the max basal limit consists of the overbasalisation limit multiplied by the body weight of the subject.

24. The system of claim 22, wherein when the overall titration glucose level is greater than the upper limit target glucose range of the subject and when the most recent adjustment day dose recommendation is less than the max basal limit of the subject, then the updated adjustment day dose recommendation is determined to be the determined dose guidance baseline plus a predetermined number of units of long-acting or ultra-long-acting insulin.

25. The system of claim 22, wherein when the overall titration glucose level is greater than the upper limit target glucose range of the subject and when the most recent adjustment day dose recommendation is greater than or equal to the max basal limit of the subject, then the updated adjustment day dose recommendation is determined to be the determined dose guidance baseline.

26. The system of claim 22, wherein when the overall titration glucose level is between the upper limit target glucose range of the subject and the lower target glucose range of the subject, then the updated adjustment day dose recommendation is determined to be the determined dose guidance baseline.

27. The system of claim 22, wherein when the daily titration glucose level is less than the lower target glucose range of the subject, then the updated adjustment day dose recommendation is determined to be the determined dose guidance baseline minus a predetermined number of units of long-acting or ultra-long-acting insulin.

28. The system according to claim 27, wherein the predetermined number of units of long-acting or ultra-long-acting insulin by which to alter the adjustment day dose recommendation is selected from the set of at least 1 unit, 2 units, 4 units, 6 units and 8 units.

29. The system of claim 1, wherein the method further comprises updating the dose guidance recommendation for the subject, unless the injection history of the subject comprises one or more injections of the subject that have injection timestamps within the immediately preceding 4 hours or less, the immediately preceding 8 hours or less, the immediately preceding 12 hours or less, or the immediately preceding 16 hours or less.

* * * * *

UNITED STATES PATENT AND TRADEMARK OFFICE
CERTIFICATE OF CORRECTION

PATENT NO. : 12,226,458 B2
APPLICATION NO. : 16/417032
DATED : February 18, 2025
INVENTOR(S) : Alan John Michelich et al.

Page 1 of 1

It is certified that error appears in the above-identified patent and that said Letters Patent is hereby corrected as shown below:

In the Claims

At Column 56, Claim number 1, Line number 15, Please delete "subject,;" and insert "subject;"

At Column 57, Claim number 2, Line number 4, Please delete "a-amino" and insert "α-amino"

At Column 57, Claim number 2, Line number 6, Please delete "a-amino" and insert "α-amino"

At Column 57, Claim number 2, Line number 15, Please delete "a-amino" and insert "α-amino"

At Column 57, Claim number 2, Line number 46, Please delete "a-amino" and insert "α-amino"

At Column 59, Claim number 16, Line number 38, Please delete "course, then" and insert "course then,"

Signed and Sealed this
Twenty-third Day of September, 2025

John A. Squires
*Director of the United States Patent and Trademark Office*